United States Patent
Tu et al.

(10) Patent No.: US 11,103,495 B2
(45) Date of Patent: *Aug. 31, 2021

(54) METHYLPHENIDATE EXTENDED RELEASE CHEWABLE TABLET

(71) Applicant: Tris Pharma, Inc., Monmouth Junction, NJ (US)

(72) Inventors: Yu-Hsing Tu, West Windsor, NJ (US); Ashok Perumal, Monmouth Junction, NJ (US); Kalyan Kathala, Monmouth Junction, NJ (US)

(73) Assignee: TRIS PHARMA, INC, Monmouth Junction, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/213,744

(22) Filed: Mar. 26, 2021

(65) Prior Publication Data

US 2021/0213007 A1    Jul. 15, 2021

Related U.S. Application Data

(63) Continuation of application No. 17/113,856, filed on Dec. 7, 2020, which is a continuation of application No. 17/070,824, filed on Oct. 14, 2020, which is a continuation of application No. 16/700,517, filed on Dec. 2, 2019, now Pat. No. 10,857,143, which is a continuation of application No. 16/033,352, filed on Jul. 12, 2018, now Pat. No. 10,507,203, which is a continuation of application No. 15/660,046, filed on Jul. 26, 2017, now abandoned, which is a continuation of application No. 15/491,547, filed on Apr. 19, 2017, now Pat. No. 9,844,545, which is a continuation of application No. 15/009,480, filed on Jan. 28, 2016, now Pat. No. 9,844,544, which is a continuation of application No. 14/872,226, filed on Oct. 1, 2015, now Pat. No. 9,295,642, which is a continuation of application No. 14/624,998, filed on Feb. 18, 2015, now Pat. No. 9,180,100, which is a continuation of application No. 14/300,580, filed on Jun. 10, 2014, now Pat. No. 8,999,386, which is a continuation of application No. PCT/US2013/054930, filed on Aug. 14, 2013.

(60) Provisional application No. 61/774,783, filed on Mar. 8, 2013, provisional application No. 61/683,513, filed on Aug. 15, 2012.

(51) Int. Cl.
| | | |
|---|---|---|
| A61K 9/20 | (2006.01) | |
| A61K 31/4458 | (2006.01) | |
| A61K 9/00 | (2006.01) | |
| A61K 9/28 | (2006.01) | |
| A61K 9/24 | (2006.01) | |
| A61K 47/58 | (2017.01) | |
| A61K 9/50 | (2006.01) | |

(52) U.S. Cl.
CPC ........ *A61K 31/4458* (2013.01); *A61K 9/0056* (2013.01); *A61K 9/20* (2013.01); *A61K 9/209* (2013.01); *A61K 9/2013* (2013.01); *A61K 9/2027* (2013.01); *A61K 9/2054* (2013.01); *A61K 9/2072* (2013.01); *A61K 9/2077* (2013.01); *A61K 9/2081* (2013.01); *A61K 9/2086* (2013.01); *A61K 9/28* (2013.01); *A61K 9/284* (2013.01); *A61K 9/2846* (2013.01); *A61K 47/585* (2017.08); *A61K 9/5026* (2013.01)

(58) Field of Classification Search
CPC .. A61K 9/2077; A61K 9/2027; A61K 9/2086; A61K 9/2081; A61K 9/0056
See application file for complete search history.

(56) References Cited

U.S. PATENT DOCUMENTS

| | | | |
|---|---|---|---|
| 2,990,332 A | 6/1961 | Keating et al. | |
| 3,138,525 A | 6/1964 | Koff | |
| 3,499,960 A | 3/1970 | Macek | |
| 3,594,470 A | 7/1971 | Borodkin | |
| 3,979,349 A | 9/1976 | Fink | |

(Continued)

FOREIGN PATENT DOCUMENTS

| | | |
|---|---|---|
| BE | 729827 | 9/1969 |
| CA | 2742680 A1 | 5/2010 |

(Continued)

OTHER PUBLICATIONS

Defendant Teva Pharmaceuticals USA, Inc.'s Initial Invalidity Contentions, dated Oct. 6, 2020, *Tris Pharma, Inc, v. Teva Pharmaceuticals USA, Inc*, In the United States District Court for the District of New Jersey, C.A. No. 20-cv-05212-KM-JBC, pp. 1-238.

(Continued)

*Primary Examiner* — Micah Paul Young
(74) *Attorney, Agent, or Firm* — Howson & Howson LLP; Cathy Kodroff; Egon Berg

(57) ABSTRACT

An oral methylphenidate extended release tablet is described, which can be scored and still retain its extended release profile. The tablet contains a combination of an uncoated methylphenidate—ion exchange resin complex, a barrier coated methylphenidate—ion exchange resin complex—matrix, and an uncomplexed methylphenidate active component. Following administration of a single dose of the extended release methylphenidate chewable tablet, a therapeutically effective amount of methylphenidate is reached in less than about 20 minutes and the composition provides a twelve-hour extended release profile.

30 Claims, 1 Drawing Sheet

(56) References Cited

U.S. PATENT DOCUMENTS

| | | |
|---|---|---|
| 4,221,778 A | 9/1980 | Raghunathan |
| 4,510,128 A | 4/1985 | Khanna |
| 4,600,645 A | 7/1986 | Ghebre-Sallasie |
| 4,762,709 A | 8/1988 | Sheumake |
| 4,765,989 A | 8/1988 | Wong |
| 4,794,001 A | 12/1988 | Mehta |
| 4,871,549 A | 10/1989 | Veda |
| 4,876,094 A | 10/1989 | Benton |
| 4,891,549 A | 1/1990 | Geoghegan |
| 4,894,239 A | 1/1990 | Nonomura et al. |
| 4,910,214 A | 3/1990 | Karjalainen |
| 4,952,402 A | 8/1990 | Sparks |
| 4,910,932 A | 10/1990 | Theeuwes |
| 4,996,047 A | 2/1991 | Kelleher |
| 4,999,189 A | 3/1991 | Kogan |
| 5,032,393 A | 7/1991 | Douglas |
| 5,093,200 A | 3/1992 | Watanabe |
| 5,156,850 A | 10/1992 | Wong et al. |
| 5,186,930 A | 2/1993 | Kogan |
| 5,219,563 A | 6/1993 | Douglas |
| 5,260,068 A | 11/1993 | Chen |
| 5,275,819 A | 1/1994 | Amer |
| 5,275,820 A | 1/1994 | Chang |
| 5,368,852 A | 11/1994 | Umemoto |
| 5,411,745 A | 5/1995 | Oshlack |
| 5,422,121 A | 6/1995 | Lehmann |
| 5,496,561 A | 3/1996 | Okada |
| 5,837,284 A | 11/1998 | Mehta |
| 5,874,090 A | 2/1999 | Baker |
| 5,980,088 A | 11/1999 | Iwasaki |
| 5,980,882 A | 11/1999 | Eichman |
| 6,001,392 A | 12/1999 | Wen |
| 6,057,289 A | 5/2000 | Mulye |
| 6,217,904 B1 | 4/2001 | Midha |
| 6,228,398 B1 | 5/2001 | Devane et al. |
| 6,231,936 B1 | 5/2001 | Kozimor |
| 6,322,011 B1 | 11/2001 | Burnside |
| 6,344,215 B1 | 2/2002 | Bettman |
| 6,384,020 B1 | 5/2002 | Flanner |
| 6,419,960 B1 | 7/2002 | Krishnamurthy et al. |
| 6,431,440 B1 | 8/2002 | Tsuchino |
| 6,432,440 B1 | 8/2002 | Watts |
| 6,436,430 B1 | 8/2002 | Mulye |
| 6,551,620 B2 | 4/2003 | Otterbeck |
| 6,555,127 B2 | 4/2003 | Steiner |
| 6,555,136 B2 | 4/2003 | Midha |
| 6,569,463 B2 | 5/2003 | Patel |
| 6,919,373 B1 | 7/2005 | Lam et al. |
| 6,923,988 B2 | 8/2005 | Patel |
| 6,974,591 B2 | 12/2005 | Kendrup |
| 7,083,808 B2 | 8/2006 | Goldenheim |
| RE41,148 E | 2/2010 | Burnside |
| 7,691,880 B2 | 4/2010 | Herman |
| RE42,096 E | 1/2011 | Burnside |
| 7,906,145 B2 | 3/2011 | Castan |
| 8,062,667 B2 | 11/2011 | Mehta |
| 8,202,537 B2 | 6/2012 | Mehta |
| 8,202,542 B1 | 6/2012 | Mehta |
| 8,287,848 B2 | 10/2012 | Mehta |
| 8,287,903 B2 | 10/2012 | Mehta |
| 8,318,210 B2 | 11/2012 | Tengler |
| 8,337,890 B2 | 12/2012 | Mehta |
| 8,465,765 B2 | 6/2013 | Mehta |
| 8,465,768 B2 | 6/2013 | Park et al. |
| 8,470,375 B1 | 6/2013 | McMahen |
| 8,491,935 B2 | 7/2013 | Mehta |
| 8,512,688 B2 | 8/2013 | Mehta |
| 8,563,033 B1 | 10/2013 | Mehta |
| 8,597,684 B2 | 12/2013 | Mehta |
| 8,623,409 B1 | 1/2014 | Mehta |
| 8,709,491 B2 | 4/2014 | Tengler |
| 8,747,902 B2 | 6/2014 | Mehta et al. |
| 8,778,390 B2 | 7/2014 | Mehta |
| 8,790,700 B2 | 7/2014 | Mehta et al. |
| 8,840,924 B2 | 9/2014 | Tengler |
| 8,883,217 B2 | 11/2014 | Mehta et al. |
| 8,956,649 B2 | 2/2015 | Mehta et al. |
| 8,999,386 B2 * | 4/2015 | Tu ................. A61K 9/2072 424/464 |
| 9,017,731 B2 | 4/2015 | Tengler |
| 9,040,083 B2 | 5/2015 | Mehta et al. |
| 9,057,675 B2 | 6/2015 | Tengler |
| 9,072,680 B2 | 7/2015 | Tengler |
| 9,089,496 B2 | 7/2015 | Tengler |
| 9,180,100 B2 | 11/2015 | Tu |
| 9,180,104 B2 | 11/2015 | Nelson et al. |
| 9,181,100 B2 * | 11/2015 | Tzeng ................. C01B 32/194 |
| 9,198,864 B2 | 12/2015 | Mehta |
| 9,265,737 B2 | 2/2016 | Tengler |
| 9,295,642 B2 * | 3/2016 | Tu ................. A61K 9/2081 |
| 9,296,642 B2 | 3/2016 | Lee et al. |
| 9,545,399 B2 * | 1/2017 | Tu ................. A61K 9/2081 |
| 9,675,703 B2 | 6/2017 | Mehta |
| 9,675,704 B2 | 6/2017 | Mehta |
| 9,844,544 B2 * | 12/2017 | Tu ................. A61K 9/2077 |
| 9,844,545 B2 * | 12/2017 | Tu ................. A61K 9/2072 |
| 10,507,203 B2 * | 12/2019 | Tu ................. A61K 9/2072 |
| 10,857,143 B2 * | 12/2020 | Tu ................. A61K 9/28 |
| 2001/0038853 A1 | 11/2001 | Kendrup |
| 2001/0046472 A1 | 11/2001 | Steiner |
| 2002/0058061 A1 | 5/2002 | Midha |
| 2002/0156133 A1 | 10/2002 | Bartholomaeus |
| 2003/0099711 A1 | 1/2003 | Kao |
| 2003/0185873 A1 | 10/2003 | Chasin |
| 2004/0059002 A1 | 3/2004 | Couch |
| 2004/0096501 A1 | 5/2004 | Vaya |
| 2004/0131680 A1 | 7/2004 | Goldenheim et al. |
| 2004/0228830 A1 | 11/2004 | Hirsh |
| 2005/0019292 A1 | 1/2005 | Acher et al. |
| 2005/0019393 A1 | 1/2005 | Augsburger |
| 2005/0181050 A1 * | 8/2005 | Hirsh ................. A61K 47/585 424/469 |
| 2005/0220881 A1 | 10/2005 | Mehta |
| 2005/0265955 A1 | 12/2005 | Raman |
| 2006/0115529 A1 | 6/2006 | Jeong |
| 2006/0134148 A1 | 6/2006 | Hollenbeck |
| 2006/0240105 A1 | 10/2006 | Devane |
| 2006/0240128 A1 | 10/2006 | Schlagheck |
| 2006/0286174 A1 | 12/2006 | Raman |
| 2007/0042955 A1 | 2/2007 | Mickle |
| 2007/0160675 A1 | 7/2007 | Devane |
| 2007/0215511 A1 | 9/2007 | Mehta |
| 2007/0218140 A1 | 9/2007 | Tanabe |
| 2008/0064694 A1 | 3/2008 | Heil |
| 2008/0075769 A1 | 3/2008 | Poestges |
| 2008/0118570 A1 | 5/2008 | Liu |
| 2008/0118571 A1 | 5/2008 | Lee |
| 2009/0011027 A1 | 1/2009 | Pathak |
| 2009/0220611 A1 | 9/2009 | Dargelas |
| 2009/0221552 A1 | 9/2009 | Teicher |
| 2010/0087501 A1 | 4/2010 | Mehta |
| 2010/0260844 A1 | 10/2010 | Scicinski |
| 2010/0278901 A1 | 11/2010 | Tengler et al. |
| 2011/0262539 A1 | 10/2011 | Bosse |
| 2012/0148672 A1 | 6/2012 | Mehta |
| 2013/0079415 A1 | 3/2013 | Vergnault |
| 2013/0236554 A1 | 9/2013 | Tengler |
| 2013/0243689 A1 | 9/2013 | Tengler |
| 2013/0243869 A1 | 9/2013 | Tengler |
| 2013/0243871 A1 | 9/2013 | Tengler |
| 2014/0004160 A1 | 1/2014 | Mehta |
| 2014/0023705 A1 | 1/2014 | Tengler |
| 2014/0030348 A1 | 1/2014 | Tengler |
| 2014/0037728 A1 | 2/2014 | Tengler |
| 2014/0050796 A1 | 2/2014 | Tengler |
| 2014/0056984 A1 | 2/2014 | Mehta |
| 2014/0072645 A1 | 3/2014 | Tengler |
| 2014/0093578 A1 | 4/2014 | Mehta |
| 2014/0112996 A1 | 4/2014 | Tengler |
| 2014/0127306 A1 | 5/2014 | Mehta |
| 2014/0212493 A1 | 7/2014 | Mehta et al. |
| 2014/0287041 A1 | 9/2014 | Tu |
| 2014/0294916 A1 | 10/2014 | Tu |
| 2015/0024059 A1 | 1/2015 | Mehta et al. |

(56) References Cited

U.S. PATENT DOCUMENTS

| | | |
|---|---|---|
| 2015/0157574 A1 | 6/2015 | Tu et al. |
| 2015/0182469 A1 | 7/2015 | Mehta et al. |
| 2016/0008312 A1 | 1/2016 | Nelson et al. |
| 2016/0143846 A1 | 5/2016 | Tu |
| 2016/0143854 A1 | 5/2016 | Tu et al. |
| 2016/0158373 A1 | 6/2016 | Mehta |

FOREIGN PATENT DOCUMENTS

| | | |
|---|---|---|
| CA | 2758556 A1 | 5/2013 |
| CN | 1179450 | 4/1998 |
| DE | 2246037 | 4/1974 |
| EP | 0294103 | 12/1988 |
| EP | 0367746 | 5/1990 |
| EP | 0565301 | 10/1993 |
| EP | 09434341 | 9/1999 |
| EP | 1186293 | 3/2002 |
| EP | 1240897 | 9/2002 |
| GB | 1358001 | 2/1974 |
| JP | H02-172912 | 7/1990 |
| JP | H05-279247 | 10/1993 |
| JP | 2005-528910 | 9/2003 |
| JP | 2005-306778 | 11/2005 |
| WO | WO87/00044 | 1/1987 |
| WO | WO-1998-014168 | 4/1988 |
| WO | WO90/09168 | 8/1990 |
| WO | WO-1998/027961 | 7/1998 |
| WO | WO-2000/40224 | 7/2000 |
| WO | WO-2002/034234 | 5/2002 |
| WO | WO-2003/020242 | 3/2003 |
| WO | WO-2004/060357 | 7/2004 |
| WO | WO-2005/102269 | 11/2005 |
| WO | WO-2005/120468 | 12/2005 |
| WO | WO-2006/021426 | 3/2006 |
| WO | WO-2006/101536 | 9/2006 |
| WO | WO-2007/109104 | 9/2007 |
| WO | WO-2007/109104 A2 | 9/2007 |
| WO | WO-2008/064163 | 5/2008 |
| WO | WO-2012/112140 | 8/2012 |
| WO | WO2012/112140 A1 | 8/2012 |
| WO | WO-2013/003622 | 1/2013 |

OTHER PUBLICATIONS

Joint Claim Construction and Prehearing Statement, Document 45, filed Feb. 19, 2021, *Tris Pharma, Inc, v. Teva Pharmaceuticals USA, Inc*, In the United States District Court for the District of New Jersey, C.A. No. 20-cv-05212-KM-JBC, pp. 1-79.

*Tris Pharma, Inc. v. Actavis Laboratories FL, Inc.*, Opening Brief for the Defendant—Appellant, C.A. No. 14-1309-CFC, Feb. 7, 2021.

Ahmann, Placebo-Controlled Evaluation of Amphetamine Mixture-Dextroamphetamine Salts and amphetamine Salts (Adderall): Efficacy Rate and Side Effects, Pediatrics, 107(1): 1, Jan. 1, 2001.

BASF Product Catalog, BASF Fine Chemicals, Switzerland, Aug. 2008.

Chourasia, "Pharmaceutical Approaches to Colon Targeted Drug Delivery Systems", J. Pharm. Pharmaceutic. Sci. 6(1):33-66, Jan.-Apr. 2003.

Conners, "Chemical Stability of Pharmaceuticals. A Handbook for Pharmacists", 2nd Ed., New York, NY, pp. 587-589 (John Wiley & Sons, Jan. 1, 1986).

Focalin® XR NDA Approval Letter from the Department of Health and Human Services dated May 26, 2005.

Focalin® XR, Highlights of Prescribing Information, Label Revised Jan. 2012.

H.C. Ansel et al, Pharmaceutical Dosage Forms and Drug Delivery Systems, 6th Ed., 213-221 (Williams & Watkins, Jan. 1, 1995).

J.M. Swanson, et al, "Comparison of Once-Daily Extended-Release Methylphenidate Formulations in Children with Attention-Deficit/Hyperactivity Disorder in the Laboratory School (The Comacs Study)," Pediatrics, 113(3): 206-16 (Mar. 3, 2004).

Kimko, "Pharmacokinetics and clinical effectiveness of methylphenidate", Clinical Pharmacokinetics, 37:457-470, Dec. 1999.

L.L. Greenhill, et al, "Double-Blind, Placebo-Controlled Study of Modified-Release Methylphenidate in Children with Attention-Deficit/Hyperactivity Disorder", Pediatrics, 109(3): 107 (Mar. 3, 2002).

Metadate CD® NDA Approval Letter from the Department of Health and Human Services dated Feb. 2, 2001.

Metadate CD®, Product Label, 2013.

Methylin® ER NDA Approval Letter from the Department of Health and Human Services dated May 9, 2000.

Meyer, FDA's ACPS Meeting accessed at http://www.fda.gov/ohrms/dockets/ac/05/briefing/2005-4187B1_01_08-Alcohol-Induced.pdf, Oct. 2005.

Padmanabhan, "Methylphenidate hydrochloride", Analytical Profiles of Drug Substances, 10:473-497, 1981.

Pearnchob, Coating with Extended Release, Excipients and Actives for Pharma, Kollidon, 12:2-5, Jun. 2004.

Quadir, Development of High Functionality Excipients for Immediate and Sustained Release Dosage Forms, FDA Excipient Workshop, Sep. 20, 2004.

Quillivant® XR NDA Approval Letter from the Department of Health and Human Services dated Sep. 27, 2012.

Quillivant® XR, Highlights of Prescribing Information, Label Revised Dec. 2013.

Ritalin-LA® NDA Approval Letter from the Department of Health and Human Services dated Jun. 5, 2002.

Ritalin-LA®, Product Label, Dec. 13, 2013.

Ritalin-SR® NDA Approval Letter from the Department of Health and Human Services dated May 21, 2004.

Ritalin-SR®, Product Label, Dec. 13, 2013.

Shao, Drug Release from Kollicoat SR 30D-CAotedd Nonpareil Beads: Evaluation of Coating Level, Plasticizer Type, and Curing Condition, AAPS PharmSciTech 3(2):1015 (2002).

Shao, Effects of Formulation Variables and Post-compression Curing on Drug Release from a New Sustained-Release Matrix Material: Polyvinylacetate-Povidone, Pharmaceutical Development and Technology, 6(2):247-254, 2001.

Teter, "Illicit methylphenidate use in an undergraduate student sample: prevalence and risk factors", Pharmacotherapy, 23:609-617, May 2003.

W.E. Pelham et al, "Once-a-Day Concerta Methylphenidate Versus Three-Times-Daily Methylphenidate in Laboratory and Natural Settings", Pediatrics, 107(6): 1-15 (Jun. 6, 2001).

pdr.net, "Metadate CD", Physician's Desk Reference, retrieved from http://www.pdr.net/drug-summary/metadate-cd?druglabelid=578&id=1032 on Oct. 9, 2015. Aug. 2010, pp. 1-5.

pdr.net, "Daytrana", Physician's Desk Reference, retrieved from http://www.pdr.net/drug-summary/daytrana?druglabelid=2102&id=4165 on Oct. 9, 2015. Aug. 2010, pp. 1-7.

pdr.net, "Concerta", Physician's Desk Reference, retrieved from http://www.pdr.net/drug-summary/concerta?druglabelid=267&id=3593on Oct. 9, 2015. Aug. 2010, pp. 108.

concerta.net, "Concerta: Highlights of Prescribing Information", retrieved from http://www.concerta.net/children/prescribing-information.html on Oct. 9, 2015. Dec. 2013, pp. 1-11.

Medsafe.gov, "Data Sheet: Rubifen, Rubifen SR", retrieved from http://www.medsafe.govt.nz/profs/datasheet/r/rubifentabsrtab.pdf on Oct. 9, 2015.

Adjei et al., Single-dose pharmacokinetics of methylphenidate extended-release multiple layer beads administered as intact capsule or sprinkles versus methylphenidate immediate-release tablets (Ritalin(®)) in healthy adult volunteers, J Child Adolesc Psychopharmacol, vol. 24(10), Dec. 2014, pp. 570-578.

Biederman, J., New-Generation Long-Acting Stimulants for the Treatment of Attention-Deficit/Hyperactivity Disorder, Medscape Psychiatry, vol. 8(2), Nov. 2003, pp. 1-10.

Bright et al., ADHD Perspectives: Current Trends and the Rationale For Transdermal Therapy, Supplement to Pediatric News, Oct. 2013, pp. 1-12.

(56) References Cited

OTHER PUBLICATIONS

Cascade et al., Short-acting versus Long-acting Medications for the Treatment of ADHD, Psychiatry(Edgemont), vol. 5(8), Aug. 2008, pp. 24-27.

Childress et al., The use of methylphenidate hydrochloride extended-release oral suspension for the treatment of ADHD, Expert Rev Neurother, vol. 13(9), Sep. 2013, pp. 979-988.

Dahl, T.C., Handbook of Pharmaceutical Excipients (6$^{th}$ Ed.): Ethylcellulose, Pharmaceutical Press, London, Feb. 2009, pp. 262-267.

Daytrana® NDA Approval Letter from the Department of Health and Human Services dated Apr. 4, 2006, pp. 1-9.

Ebert et al., The Effects of Increasing Plasma Concentrations of Dexmedetomidine in Humans, Anesthesiology, vol. 93, Aug. 2000, pp. 382-394.

Faraone et al., The worldwide prevalence of ADHD: is it an American condition?, World Psychiatry, vol. 2(2), Jun. 2003, pp. 104-113.

fda.gov, Clinical Pharmacology and Biopharmaceutics Reviews: Concerta, retrieved from http://www.accessdata.fda.gov/drugsatfda_docs/nda/2000/21-121_Concerta_biopharmr.pdf on Jul. 15, 2016. Jun. 2000, pp. 1-112.

fda.gov, Clinical Pharmacology and Biopharmaceutics Reviews: Methylin, retrieved from http://www.accessdata.fda.gov/drugsatfda_docs/nda/2002/21-419_Methylin_BioPharmr.pdf on Jul. 14, 2016. Jul. 2001, pp. 1-54.

fda.gov, Drugs@FDA Frequently Asked Questions, retrieved at http://www.fda.gov/Drugs/InformationOnDrugs/ucm075234.htm on Jul. 18, 2016. Last updated Mar. 2015, pp. 1-7.

fda.gov, Methylin® Oral Solution—NDA Approval Letter, retrieved from http://www.accessdata.fda.gov/drugsatfda_docs/appletter/2002/21419ltr.pdf on Jul. 15, 2016, Dec. 19, 2002, pp. 1-4.

fda.gov, Orange Book Listing: Metadate CD, retrieved from http://www.accessdata.fda.gov/scripts/cder/ob/docs/obdetail.cfm?Appl_No=021259&TABLE1=OB Rx on Jul. 14, 2016. Apr. 2001, pp. 1-3.

fda.gov, Quillichew—NDA Approval Letter, retrieved from http://www.accessdata.fda.gov/drugsatfda_docs/appletter/2015/207960Orig1s000ltr.pdf on Jul. 8, 2016, Dec. 4, 2015, pp. 1-5.

Greenhill et al., Practice Parameter for the Use of Stimulant Medications in the Treatment of Children, Adolescents, and Adults, Child Adolesc. Psychiatry, vol. 41(2), Feb. 2002, pp. 26S-49S.

Kessler et al., The prevalence and correlates of adult ADHD in the United States: Results from the National Comorbidity Survey Replication, Am J Psychiatry, vol. 163(4), Apr. 2006, pp. 716-723.

Kooij et al., European consensus statement on diagnosis and treatment of adult ADHD: The European Network Adult ADHD, BMC Psychiatry, vol. 10(67), Sep. 2010, pp. 1-24.

Mallinckrodt Inc., Methylin® Oral Solution (product label), retrieved from http://www.accessdata.fda.gov/drugsatfda_docs/label/2013/021419s007lbl.pdf on Jul. 14, 2016. Dec. 2013, pp. 1-16.

Markowitz et al., Advances in the pharmacotherapy of attention-deficit-hyperactivity disorder: focus on methylphenidate formulations, Pharmacotherapy, vol. 23(10), Oct. 2003, pp. 1281-1299.

Nextwave Pharmaceuticals, Inc., "QuilliChew ER—Methylphenidate HCl: Highlights of Prescribing Information", retrieved from http://labeling.pfizer.com/ShowLabeling.aspx?id=2577 on Jul. 8, 2016, Dec. 2015, pp. 1-14.

Patrick et al., Evolution of stimulants to treat ADHD: transdermal methylphenidate, vol. 24(1), Hum Psychopharmacol, Jan. 2009, pp. 1-17.

Patrick et al., Influence of ethanol and gender on methylphenidate pharmacokinetics and pharmacodynamics, Clin Pharmacol Ther, vol. 81(3), Mar. 2007, pp. 346-353.

pdr.net, "Focalin® XR", Physician's Desk Reference, retrieved from http://www.pdr.net/drug-summary/Focalin-XR-dexcphenidate-hydrochloride-431.3616 on Jul. 14, 2016. Aug. 2010, pp. 2472-2477.

pdr.net, Ritalin LA, retrieved from http://www.pdr.net/drug-summary/Ritalin-LA-methylphenidate-hydrochloride-1003 on Jul. 14, 2016. Jan. 2006, pp. 1-3.

pdr.net, Tussionex, retrieved from http://www.pdr.net/drug-summary/Tussionex-chlorpheniramine-polistirex-hydrocodone-polistirex-579.2803 on Jul. 14, 2016. Jan. 2010, pp. 1-2.

Pliszka, Practice Parameter for the Assessment and Treatment of Children and Adolescents With Attention-Deficit/Hyperactivity Disorder, The AACAP Work Group on Quality Issues, J. Am. Acad. Child Adolesc. Psychiatry, vol. 46(7), Jul. 2007, pp. 894-921.

Rodriguez-Torres et al., Effect of ribavirin on intracellular and plasma pharmacokinetics of nucleoside reverse transcriptase inhibitors in patients with human immunodeficiency virus-hepatitis C virus coinfection: results of a randomized clinical study, Antimicrob Agents Chemother, vol. 49(10), Oct. 2005, pp. 3997-4008.

Rohm and Haas, Amberlite™ IRP69, Feb. 2006, pp. 1-5.

Schapperer et al., Bioequivalence of Sandoz methylphenidate osmotic-controlled release tablet with Concerta® (Janssen-Cilag), Pharmacol Res Perspect, vol. 3(1), Feb. 2015, pp. e00072.

Stearns et al., Active tamoxifen metabolite plasma concentrations after coadministration of tamoxifen and the selective serotonin reuptake inhibitor paroxetine, J Natl Cancer Inst, vol. 95(23), Dec. 2003, pp. 1758-1764.

Stier et al., Use of partial area under the curve metrics to assess bioequivalence of methylphenidate multiphasic modified release formulations, AAPS J, vol. 14(4), Dec. 2012, pp. 925-926.

Swanson et al., Development of a new once-a-day formulation of methylphenidate for the treatment of attention-deficit/hyperactivity disorder: proof-of-concept and proof-of-product studies, Arch Gen Psychiatry, vol. 60(2), Feb. 2003, pp. 204-211.

The Dow Chemical Company, Ethocel: Ethylcellulose Polymers Technical Handbook, Sep. 2005, pp. 1-28.

Tris Phamra, Inc., Tris Pharma Announces US Patent Grant Covering Platform Technology (OralXR Press Release), retrieved from http://www.trispharma.com/news_New-US-Patent-Grant_Jan2012.php on Jul. 14, 2016. Jan. 2012, p. 1.

Lasser et al, Comparative Efficacy and Safety of Lisdexamfetamine Dimesylate and Mixed Amphetamine Salts Extended Release in Adults with Attention-Deficit/Hyperactivity Disorder, Primary Psychiatry (http://primarypsychiartry.com/authhor/primaryp/), May 21, 2013.

Wigal et al., "Selection of the Optimal Dose Ratio for a Controlled-Delivery Formulation of Methylphenidate", J. Appl. Research., vol. 3:46-63, Oct. 2003.

"DrugFacts: Stimulant ADHD Medications—methyphenidate and Amphetamine", https://www.drugabuse.gov/publications/drugfacts/stimulant-adhd-medications-methylphenidate-amphetamines, revised Jan. 2014, accessed Sep. 1, 2016.

S M Outram, "The Use of methylphenidate among students: the future of enhancement?" J Med Ethics, 2010: 36: 198-2020, downloaded by http://jme.bmj.com on Sep. 1, 2016.

Amberlite IRP and Duolite AP Ion Exchange Resins, Ion Exchange Resins—Healthcare, Rohm Haas, pp. 1, www.F:/Heathcare_Website/formulations_products.htm (Feb. 9, 2006).

T Spencer et al, "Effiacy of a Mixed Amphetamine Salts of Compound in Adults with Attention-Deficit/Hyperactivity Disorder", Arch Gen Psychiatry, 2001, 58: 775-782.

AS Gehris et al, "Controlled Release of an Opiate Drug Using Ion Exchange Resin", AAPS 2014 Poster Submission downloaded from http:/abstracts.aaps.org/Verify/AAPS2014/PosterSubmssions/W4037.pdf, Sep. 30, 2015.

JS Markowitz et al, "Ethylphenidate Formation in Human Subjects After Administration of a Single Dose of Methylphenidate and Ethanol", Drug Metabolism and Disposiiton, 28: 620-624 (2000).

JS Markowitz et al, "Pharmacokinetics of Methylphenidate After Oral Administration of Two Modified-Release Formulations in Healthy Adults", Clin Pharmacol., 42(4): 393-401 (2003).

NDA20100, Clinical Pharmacology and Biopharmaceutics Review(s), Applicatoin No. 20100Orig1s000, Center for Drug Evaluation and Research, revised Mar. 21, 2011, http://www.accessdata.fda.gov/drugsatfda_docs/nda/2012/202100Orig1s000ClinPharmR.pdf.

Dyanavel™ XR product literature, revised Nov. 2015, (accessed at http://www.accessdata.fda.gov/drugsatfda_docs/label/2015/208147s000lbl.pdf) on Sep. 1, 2016.

The Pharmacopeia of the United States (25$^{th}$ revision), "Pharmaceutical Dosage Forms", pp. 2213-2225, Nov. 2001.

(56) References Cited

OTHER PUBLICATIONS

The Physicians' Desk Reference for Non-Prescription Drugs, Dietary Supplements, and Herbs (29$^{th}$ Ed.), "Delsym®", pp. 602-603, Jan. 2008.
Chavez et al., An Update on Central Nervous System Stimulant Formulations in Children and Adolescents with Attention-Deficit/Hyperactivity Disorder, The Annals of Pharmacotherapy, vol. 43, Jun. 2009, pp. 1084-1095.
Childress et al., The single-dose pharmacokinetics of NWP06, a novel extended-release methylphenidate oral suspension, Postgrad Med, vol. 122(5), Sep. 2010, pp. 35-41.
Flynn, Buffers—pH Control within Pharmaceutical Systems, Parental Fundamentals, vol. 34(2), Mar. 1980, pp. 139-162.
Voskoboinikova, Drug Synthesis Methods and Manufacturing Technology, Modern Auxiliary Substances in Tablet Production: Use of High-Molecular-Weight Compounds for the Development of New Medicinal Forms and Optimization of Technological Processes, Pharmaceutical Chemistry Journal, 39(1):22-28 (Jan. 2005).
Active Ingredients, Ion Exchange Resins—Healthcare, Rohm Haas, pp. 1, www.F:/Heathcare_Website/deliquescence.htm (Feb. 9, 2006).
Adderall® Product Insert, revised Mar. 2007 and Adderall XR® Product Insert (revised Dec. 2013.).
Angrist, Comparative Psychotomimetic Effects of Stereoisomers of Amphetamine, Nature, 234:152-153 (Nov. 19, 1971).
Aoyama, Pharmacodynamic Modeling for Change of Locomotor Activity by Methylphenidate in Rats, Pharmaceutical Research, 14(11):1601-1606 (Nov. 1997).
Arnold, Levoamphetamine and Dextroamphetamine: Comparative Efficacy in the Hyperkinetic Syndrome, Archives of General Psychiatry, 27:816-822 (Dec. 1972).
BASF Aktiengesellschaft, Contents, Introduction, pp. 1-13, 2004.
Bordawekar, Evaluation of Polyvinyl Acetate Dispersion as a Sustained Release Polymer for Tablets, Drug Delivery, 13(2):121-131 (Mar. and Apr. 2006).
Borodkin, Polycarboxylic Avid Ion-Exchange Resin Adsorbates for Taste Coverage in Chewable Tablets, Journal of Pharmaceutical Science 60(10):1523-1527 (Oct. 1971).
Center of Drug Evaluation and Research, Guidance for Industry: Statistical Approaches to Establishing Bioequivalence, pp. 1-45 (Jan. 2001).
Codeprex®, Product Label, marketed by UCB, Inc., Jun. 21, 2004.
Concerta®, Medical Reviews, App. No. 21-121, Center for Drug Evaluation and Research, Jul. 1999 (completed Mar. 2000).
Dashevsky, Compression of Pellets Coated with Various Aqueous Polymer Dispersions, International Journal of Pharmaceutics, 279(1-2):19-26 (Jul. 26, 2004).
Dashevsky, Physicochemical and Release Properties of Pellets Coated with Kollicoat SR 30 D, a New Aqueous Polyvinyl Acetate Dispersion for Extended Release, International Journal of Pharmaceutics, 290(1-2):15-23 (Feb. 16, 2005; E-publication: Jan. 6, 2005).
Daughton et al., "Review of ADHD Pharmacotherapies: Advantages, Disadvantages, and Clinical Pearls", J. Am. Acad. Child and Adolescent Psychiatry, vol. 48(3):240-248, Mar. 2009.
Daytrana®, Clinical Pharamacology and Biopharmaceutics Reviews, App. No. 21-514, Center for Drug Evaluation and Research, Jun. 2005.
Daytrana®, Medical Reviews, App. No. 21-514, Center for Drug Evaluation and Research, Feb. 2006.
BASF, A New Sustained Release Excipient, ExAct, 3: 2 (Nov. 1999).
Bordawekar, Evaluation of Kollicoat® SR 30D as a Sustained Release Polymer Dispersion, BASF Corporation, University of Rhode Island, p. 25, AAPS Poster (2002).
Degussa, Creating Essentials, Specifications and Test Methods for Eudragit® NE 30 D, p. 1-4 (Sep. 2004).
Deliquescent Drugs, Ion Exchange Resins—Healthcare, Rohm Haas, pp. 1, www.F:/Heathcare_Website/deliquescence.htm (Feb. 9, 2006).
Dissolution Enhancement of Poorly Soluble Drugs, Rohm Haas Ion Exchange Resins—Healthcare, pp. 1, www.rohmhaas.com (Dec. 1, 2004).
Draganoiu, Evaluation of the New Polyvinylacetate/Povidone Excipient for Matrix Sustained Release Dosage Forms, Pharm. Ind., 63:624-629 (2001).
Generic Drug Formulations with Kollicoat® SR 30 D and Kollidon® SR, pp. 1-51, BASF (1999).
Eliminating Polymorphism, Ion Exchange Resins—Healthcare, Rohm Haas, www.F:/Heathcare_Website/polymorph.htm (Feb. 9, 2006).
El-Samaligy, Formulation and Evaluation of Sustained-Release Dextromethorphan Resinate Syrup, Egyptian Journal of Pharmaceutical Sciences, 37(1-6):509-519 (1996).
Erdmann, Coating of Different Drugs with Optimized Kollicoat EMM 30 D Coatings, BASF Aktiengesellschaft, Proceedings of the 26$^{th}$ CRS symposium (Jun. 1999), 6313.
Ermer et al., "Pharmacokinetic Variability of Long-Acting Stimulants in the Treatment of Children and Adults with Attention-Deficit/Hyperactivity Disorder", CNS Drugs, vol. 24(12):1009-1025, Dec. 2010.
Extended Release, RohmHaas Ion Exchange Resins—Healthcare, pp. 1, Rohm and Haas website, www.rohmhaas.com (Feb. 9, 2005).
FDA Guidance for Industry, Supac-MR: Modified Release Solid Oral Dosage Forms. Scale-Up and Postapproval Changes: Chemistry, Manufacturing, and Controls; In Vitro Dissolution Testing and In Vitro Bioequivalence Documentation, pp. 1-36 (Sep. 1997).
FDA Guidance for Industry: Specifications: Test Procedures and Acceptance Criteria for New Veterinary Drug Substances and New Medicinal Products: Chemical Substances, pp. 1-35 (Jun. 14, 2006).
IndustrialSpec.com, Mesh & Micron Sizes: Mesh to Micron Conversion Chart, p. 1, Aug. 27, 2015.
Focalin® XR, Clinical Pharamacology and Biopharmaceutics Reviews, App. No. 21-802, Center for Drug Evaluation and Research, Jul. 2004.
Focalin® XR, Medical Review, App. No. 21-802, Center for Drug Evaluation and Research, Jul. 2004.
Ghuman et al., "Psychopharmacological and Other Treatments in Preschool Children with Attention Deficit/Hyperactivity Disorder: Current Evidence and Practice", J. Child and Adolescent Psychopharmacology, vol. 18(5):413-447, Oct. 2008.
Gonzales et al., "Methylphenidate Bioavailability from Two Extended-Release Formulations", Int'l J. Clinical Pharmacology and Thereapeutics, vol. 40(4):175-184, Apr. 2002.
Haddish-Berhane, Modeling Film-Coat Non-Uniformity in Polymer Coated Pellets: A Stochastic Approach, International Journal of Pharmaceutics, 12; 323(1-2):64-71 (Oct. 2006; E-publication Jun. 6, 2006).
Hinsvark, The oral bioavailability and pharmacokinetics of soluble and resin-bound forms of amphetamine and phentermine in man, Journal of Pharma and BioPharma, 1(4):319-328 (Aug. 1973).
Ichikawa, Use of Ion-Exchange Resins to Prepare 100 μm-Sized Microcapsules with Prolonged Drug-Release by the Wurster Process, International Journal of Pharmaceutics 216:67-76 (Mar. 2001).
Improved Dissolution of Poorly Soluble Drugs References, pp. 1, www.F:/Heathcare_Website/Poor_Solubility_refl.htm (Feb. 9, 2006).
Ion Exchange Resins—Healthcare, Rohm Haas, Frequently Asked Questions, pp. 1-3, www:F/Heathcare_Website/gaq_print.htm (Feb. 9, 2006).
Jeong, Development of Sustained Release Fast-melting Tablets Using Ion Exchange Resin Complexes (accepted Nov. 29, 2005), Dissertations Submitted to Purdue University, W. Lafayette, Indiana, UMI #3210729.
Jeong, Drug Release Properties of Polymer Coated Ion-Exchange Resin Complexes: Experimental and Theoretical Evaluation, Journal of Pharmaceutical Sciences, pp. 1-15 (Apr. 2006).
Jeong, Evaluation of Drug Release Properties from Polymer Coated Drug/Ion-Exchange Resin Complexes Using Mathematical Simulation and Their Application into Sustained Oral Drug Delivery, Department of Pharmaceutical Chemistry, University of Kansas, Abstract (Jun. 16-18, 2005), pp. 92-105, 114, 141, 169 (Dec. 2005).
Kollicoat SR30D, Technical Information (Jan. 2004, Supercedes Jun. 1999) BASF, MEF/EP 073.
Kollicoat SR30D, Technical Information, Bulletin, MEV96 (Jun. 1999).
Kollicoat SR30D, Technical Information, ME36(e), pp. 1-14 (Jun. 1999).

(56) References Cited

OTHER PUBLICATIONS

Kolter, BASF, ExAct, 5:1-5 (Oct. 2000).
Kolter, Coated Drug Delivery Systems Based on Kollicoat® SR 30D, BASF, MEF/EP073 (Spring/Summer 2004).
Kolter, Kollicoat® SR 30 D A New Sustained Release Excipient, BASF AG, p. 1 (Nov. 1999).
Kolter, Kollicoat® SR 30 D, Coated Drug Delivery Systems, ExAct, 11:3 (Oct. 2003).
Kulshreshtha et al. (Eds.), Pharmaceutical Suspensions: From Formulation Development to Manufacturing, Springer Science & Business Media, Jan. 2009.
Metadate CD®, Clinical Pharmacology and Biopharmaceutics Reviews, App. No. 21-259, Center for Drug Evaluation and Research, Mar. 2001.
Metadate CD®, Medical Reviews, App. No. 21-259, Center for Drug Evaluation and Research, Mar. 2000.
Methylin® ER, Product Label, marketed by Mallinckrodt Inc., Oct. 2013.
Methylin® Oral Solution, Chemistry Reviews, App. No. 21-419, Center for Drug Evaluation Research, May 2002.
Methylin® Oral Solution, Clinical Pharmacology and Biopharmaceutics Reviews, App. No. 21-419, Center for Drug Evaluation and Research, Jul. 2001.
Methylin® Oral Solution, Medical Reviews, App. No. 21-419, Center for Drug Evaluation and Research, May 2002.
Mies, BASF, Pharmasolutions, MEMPD 130, Correlation of Drug Permeation Through Isolated Films and Coated Dosage Forms Based on Kollicoat 30SR D/IR, 2004 AAPS Annual Meeting and Exposition (Nov. 7-11, 2004).
Nicotine, Ion Exchange Resins—Healthcare, Rohm Haas, www.F:/HeathcareWebsite/nicotin.htm (Feb. 9, 2006).
Nisar-Ur-Rahman, Differential Scanning Calorimetry and Surface Morphology Studies on Coated Pellets using Aqueous Dispersions, Pakistan Journal of Pharmaceutical Sciences, 18(2):19-23 (Apr. 2005).
Novartis Consumer Health in Canada, Delsym, www.Novartisconsumerhealth.ca/en/products/delsym.shtml (2003).
Physician's Desk Reference: Adderall, 51st Ed. (1997).
Polymorphism References, pp. 1, www.F:/Heathcare_Website/polymorph_references.htm (Feb. 9, 2006).
Prabhu, Comparison of Dissolution Profiles for Sustained Release Resinates of BCS Class 1 Drugs Using USP Apparatus 2 and 4: A Technical Note, AAPS PharmSciTech, 9(3):769-773 (Sep. 2008).
Prince, "Pharmacotherapy of Attention-Deficit/Hyperactivity Disorder in Children and Adolescents: Update on New Stimulant Preparations, Atomoxetine, and Novel Treatments", Child and Adolescent Psychiatric Clin N. Am., vol. 15:13-50, Jan. 2006.
Product Literature, Daytrana™ (methylphenidate transdermal system) (revised Dec. 2009).
Product Literature, Focalin™ XR (dexmethylphenidate hydrochloride) extended-release capsules, Novartis Consumer Health, 2004.
Product Literature, Once Daily Metadate CD™ (methylphenidate HCl, USP) Extended-Release Capsules (Feb. 2007).
Product Literature, Ritalin® hydrochloride methylphenidate hydrochloride tablets USP and Ritalin-SR® methylphenidate hydrochloride USP sustained-release tablets (revised Dec. 2010).
Quadir, Release Characteristics . . . of selected drugs with a newly developed polyvinyl acetate dispersion, ExAct, 13:4 (Dec. 2004).
Raghunathan, Sustained-release Drug Delivery System 1: Coated ion-exchange Resin System for Phenylpropanolamine and Other Drugs, Journal of Pharmaceutical Science, 70:379-384 (Apr. 1981).
Remington, "The Science and Practice of Pharmacy ($20^{th}$ Ed)", pp. 986-994, Jan. 2000.
Remington: Pharmaceutical Science, 15th Ed., pp. 1618, 1625-1626 (1975).
Ritalin LA®, Clinical Pharmacology and Biopharmaceutics Reviews, App. No. 21-284, Center for Drug Evaluation and Research, Dec. 2001.
Ritalin LA®, Medical Review(s), App. No. 21-284, Center for Drug Evaluation and Research, Nov. 2000.
Robinson, Sustained and Controlled Release Drug Delivery Systems, Drugs and the Pharmaceutical Sciences, A Series of Textbooks and Monographs, vols. 1-6, pp. 130-210, by Marcel Dekker, Inc., New York and Basel (1978).
Rowe, Materials Used in the Film Coating of Oral Dosage Forms, Critical Reports in Applied Chemistry, 6:1-16 (1984).
Sawicki, Compressibility of Floating Pellets with Verapamil Hydrochloride Coated with Dispersion Kollicoat SR 30 D, European Journal of Pharmaceutics and Biopharmaceutics, 60(1):153-8 (May 2005; E-publication: Jan. 8, 2005).
Strübing, Mechanistic Analysis of Drug Release From Tablets with Membrane Controlled Drug Delivery, European Journal of Pharmaceutics and Biopharmaceuticals, 66(1):113-9 (Apr. 2007; E-publication: Sep. 28, 2006).
Swarbrick, Suspensions in Remington: The Science and Practice of Pharmacy, $20^{th}$ Edition, ed. Gennaro, Lippincott, 2000, pp. 316-323.
Tris Pharma, Inc., LiquiXR™, retrieved from http://www.trispharma.com/technologies liquiXR.php on Jul. 14, 2016, p. 1.
Tris Pharma, Inc., NextWave Pharmaceuticals Announces Launch of Nexiclon™ XR—First Extended-Release, Once-Daily Clonidine Oral Suspension and Tablet (Press Release), retrieved from http://www.trispharma.com/news_Nexiclon06Jan2011.php on Jul. 14, 2016. Jan. 2011, pp. 1-2.
Mendes et al., Chewable Tablets (8) from Pharmaceutical Dosage Forms ($2^{nd}$ Ed, vol. 1, Lieberman et al. (Eds.)), Marcel Dekker, Inc., New York, pp. 1-57, Jan. 1989.
Patrick et al., The Absorption of Sustained-Release Methylphenidate Formulations Compared to an Immediate-Release Formulation, Biopharmaceutics & Drug Disposition, vol. 10(2): 165-171, Mar. 1989.
FDA, Guidance for Industry Tablet Scoring: Nomenclature, Labeling, and Data for Evaluation (Draft Guidance), pp. 1-8, Aug. 2011.
BASF, Soluble Kollidon Grades (Technical Information), pp. 1-14, Jan. 2004.
BASF, Kollidon SR: A new excipient for sustained release matrices, ExAct (Excipients & Actives for Pharma) No. 4, pp. 5-6, Apr. 2000.
L. Allen et al., Ansel 's Pharmaceutical Dosage Forms and Drug Delivery Systems, 8th ed., 2005, Section II, Drug Dosage Form and Drug Delivery System Design, Chapter 4, pp. 92-141, Chapter 9, "Solid Oral Modified-Release Dosage Forms and Drug Delivery Systems", pp. 260-275, Lippincott Williams & Wilkins.
T. Aoyama, "Kinetic analysis of enantiomers of threo-methylphenidate and its metabolite in two healthy subjects after oral administration as determined by a gas chromatographic-mass spectiometric method", J. of Pharmaceutical Sciences, 79(6):465-469 (Jun. 1990).
J. Biederan, "New Generation Long-Acting Stimulants for the Treatment of Attention-Deficit/Hyperactivity Disorder", Medscape Psychiatry, 8(2) (Nov. 2003).
*FDA Accepts Tris Pharma, Inc 's ANDA with Paragraph IV Certification for a Generic Equivalent to Delsym*, BioSpace (Press Release, Jul. 16, 2009, 8:24AM), http://www.biospace.com/News/fda-accepts-U-is-phaima-inc-s-anda-withparagraph/150247.
B. Birmaher, et al., Sustained Release Methylphenidate: Pharmacokinetic Studies in ADDH Males, J. Am. Acad. Child Adolesc. Psychiatry, 28(5):768-772 (1989).
R. Bodmeier, et al., Compaction of Controlled-Release Pellets, BASF ExAct, 4: 1-4, Apr. 2000.
S. Borodkin, et al., Interaction of Amine Drugs with a Polycarboxylic Acid Iona-Exchange Resin, Journal of Pharmaceutical Sciences, 59(4):481-486 (1970).
S. Borodkin, Ion Exchange Resins and Sustained Release, Encyclopedia of Pharmaceutical Technology 8:203-216 (1993).
Chilukuri, et al., Pharmaceutical Product Development: In Vitro-In Vivo Correlation, vol. 165: 110-115 (2007).
Clinical Pharmacology and Biopharmaceutics Review(s), App. No. 21-121 Pharmacology (Concerta®), Center for Drug Evaluation and Research, pp. 1-112, Approval Date: Aug. 1, 2000; Date created: Jun. 18, 2001; https://www.accessdata.fda.gov/drugsatfda_docs/nda/2000/21-121_Concerta_biopharmr.pdf.

(56) References Cited

OTHER PUBLICATIONS

Concerta®, Drug Approval Package, Drugs@FDA, App. No. 21-121, Approval Date: Aug. 1, 2000; Date created: Jun. 18, 2001; https://www.accessdata.fda.gov/-drugsatfda_docs/nda/2000/21-121_Concerta.cfm, pp. 1-5.
D. F. Connor, et al., New Formulations of Stimulants for ADAH, CNS Drugs, 18(14) :1011-1030 (2004).
K. A. Connors et al., Chemical Stability of Pharmaceuticals: A Handbook for Pharmacists, John Wiley & Sons, 2nd ed., 586-591 (1986).
J. Daruwala, Chewable Tablets, in Pharmaceutical Dosage Forms: Tablets, edited by H. Lieberman and L. Lachman, Marcel Dekker, Inc., New York (1980).
N. G. Das and S. K. Das, Controlled-Release of Oral Dosage Forms, Formulation, Fill & Finish (2003).
C. Davis, "Effects of Liquid Methylphenidate on Academic Achievement in ADHD Elementary School Children," Kalamazoo College Thesis (Fall 2009).
K. Dorfner, Ion Exchangers: Properties and Applications, edited by A. F. Coers, Ann Arbor Science Publishers Inc., 1972.
NextWave Pharmaceuticals and Tris Pharma Enter into CNS: focused Development and Commercialization Agreement, FierceBiotech (Aug. 18, 2010) http ://www.fiercebiotech.com/biotech/nextwave-pharmaceuticals-and-tris-pharma-enter-into-cns-focused-development-and.
Guidance for Industry: Extended Release Oral Dosage Forms: Development, Evaluation, and Application of In Vitro/In Vivo Correlations, FDA, 1-24 (1997).
Gibaldi & Penier, Pharmacokinetics, Appx. 4, 15th ed., (1975).
Goodman & Gillman's, The Pharmacological Basis of Therapeutics, 11th ed., edited by L. Brunton et al. (2006).
G. Green et al., Pharmacopeial Standards for the Subdivision Characteristics of Scored Tablets, Pharmacopeial Forum, 35(6):1598-1612[Nov.-Dec. 2009].
X. Guo et al., Ion-Exchange Resins as Drug Delivery Carriers, J. Pharm. Sci. 98(11):3886-3902 (2009).
N. H. G. Holford et al., Understanding the Dose-Effect Relationship: Clinical Application of Pharmacokinetic-Pharmacodynamic Models, Clinical Pharmacokinetics, 6:429-453 (1981).
S. H. Jeong, et al., Drug loading and release properties in ion-exchange resin complexes as a drug delivery matrix, International Journal of Pharmaceutics, 361:26-32 (2008).
L. Lachman et al, "Kinetic Principles and Stability Testing," in The Theory and Practice of Industrial Pharmacy, 3rd ed., Ch. 26 (1986).
FDA accepts Tris Pharma's two NDAs for OralXR platform-based drugs, Clinical Pharmacology and Biopharmaceutics Review(s), App. No. 21-259 (Metadate CD®), Center for Drug Evaluation and Research.
Rondec® Syrup, Last Reviewed Apr. 9, 2009, http://www.rxlist.com/rondec-drug.htmm accessed May 31, 2017.
Metadate CD, Center for Drug Evaluation and Research, Application No. 21-259, Drug Approval Package, Drugs@FDA, Approval date: Apr. 30, 2001, Date Created: Apr. 4, 2002, https://www.accessdata.fda.gov/-drugsatfda_docs/nda/2001/21-259_Metadate.cfm.
Approval letter, App. No. 21-259 (Metadate CD®), Center for Drug Evaluation and Research, Drugs@FDA. Approval date: Apr. 30, 2001, Date Created: Apr. 4, 2002, https://www.accessdata.fda.gov/-drugsatfda_docs/nda/2001/21-259_Metadate.cfm.
Medical Review(s), App. No. 21-259 (Metadate CD®), Center for Drug Evaluation and Research, Drugs @FDA, Approval date: Apr. 30, 2001, Date Created: Apr. 4, 2002, https://www.accessdata.fda.gov/-drugsatfda_docs/nda/2001/21-259_Metadate.cfm.
Approval Letter, App. No. 21475 (Methylin® Chewable Tablets), Center for Drug Evaluation and Research, Drugs@FDA, Approval Date: Apr. 15, 2003, Date created: Jul. 25, 2006, https://www.accessdata.fda.gov/-drugsatfda_docs/nda/2003/021475s000_MethylinTOC.cfm.
Methylin® Chewable Tablets Label, marketed by Mallinckrodt Inc. (rev. Apr. 2003), https://www.accessdata.fda.gov/drugsatfda_docs/label/2003/21475_methylin_lbl.pdf, Approval Date: Apr. 15, 2004; date created Jul. 25, 2006.
Methylin® Oral Solution label, marketed by Mallinckrodt Inc. (rev. May 2006), https://www.accessdata.fda.gov/drugsatfda_docs/label/2006/021475s002,021419s003lbl.pdf.
Focalin XR Drug Approval Package, Drugs@FDA, Approval Date: May 26, 2005; date created: Jul. 2, 2007, https://www.accessdata.fda.gov/drugsatfda docs/-nda/2005/021802s000TOC.cfm.
Methylin Oral Solution Drug Approval Package, Drugs@FDA, Application No. 021419, Approval date: Dec. 19, 2002; Date Created: Oct. 26, 2004; https://www.accessdata.fda.gov/drugsatfda docs/nda/2002/21-419 Methylin.cfm.
Press Release, Alliant Pharmaceuticals , Inc., Making ADHD Meds Easier to Swallow (Sep. 7, 2004).
K. S. Patrick et al., New Methylphenidate Formulations for the Treatment of Attention Deficit/Hyperactivity Disorder, Exp. Opin. Drug. Deliv., 2:121-143 (2005).
The Physicians' Desk Reference, (61st ed. 2007) Ritalin® LA, 2271-74.
The Physicians' Desk Reference, (61st ed. 2007) Ritalin® SR, 2269-71.
The Physicians' Desk Reference, (65th ed. 2011) Concerta®, 2678-84.
The Physicians' Desk Reference, (65th ed. 2011) Focalin® XR, 2530-36.
The Physicians' Desk Reference, (65th ed. 2011) Metadate CD®, 3260-64.
The Physicians' Desk Reference, (64th ed. 2010) Tussionex®, 3443-3444.
Tris Pharma Announces Approval of First-Ever Generic of Tussionex Extended Release Suspension, Pipeline Review (Oct. 7, 2010) http://www.pipelinereview.com/-index.php/2010100737478/Mo_re-News/Tris-Pharma-Announces-Approval-of-First-Ever-Generic-of-Tussionex-Extended-Release-Suspension.html.
PR Newswire: Tris Pharma Announced Acceptance of Its First Two NDAs (2009).
Clinical Pharmacology and Biopharmaceutics Review(s), App. No. 202100 (Quillivant® XR), Center for Drug Evaluation and Research, Approval date: Sep. 27, 2012; Date created: Jul. 8, 2013, https://www.accessdata.fda.gov/drugsatfda_docs/-nda/2012/202100Orig1s000ClinPharmR.pdf.
Quillivant® XR label, marketed by NextWave Pharmaceuticals, Inc. (rev. Sep. 2012), https://www.accessdata.fda.gov/drugsatfda_docs/label/2012/202100lbl.pdf.
Medical Review(s), App. No. 202100 (Quillivant® XR) Center for Drug Evaluation and Research, Approval date: Sep. 27, 2012; Date created: Jul. 8, 2013, https://www.accessdata.fda.gov/drugsatfda_docs/-nda/2012/202100Orig1s000MedR.pdf.
Ritalin LA Drug Approval Package, Drugs@FDA, Application No. 21-284, Approval Date: Jun. 5, 2002, Date created: May 13, 2005; https://www.accessdata.fda.gov/-drugsatfda_docs/nda/2002/21-284_Ritalin.cfm.
Approval Letter, App. No. 21-284 (Ritalin LA®), Center for Drug Evaluation and Research, Application No. 21-284, Approval Date: Jun. 5, 2002, Date created: May 13, 2005; https://www.accessdata.fda.gov/drugsatfda_docs/nda/2002/21-284_Ritalin%20LA_Approv.pdf.
Ritalin-SR® label, marketed by Novartis (rev. Apr. 2007), https://www.accessdata.fda.gov/-drugsatfda_docs/label/2007/010187s069,018029s040,021284s011lbl.pdf.
Ritalin-SR Drag Approval Package, Drugs@FDA. NDA 018029, rev Apr. 2007, http://www.accessdata.fda.gov/scripts/cder/drugsatfda/index.cfm?fuseaction=Seach.Label . . . , accessed May 3, 2016, pp. 1-48.
M. Rochdi et al., Dose-Proportional Pharmacokinetics of a Methylphenidate Extended-Release Capsule, Int. J.Clin, Phrumacol. and Therapeutics, 42(5):285-292 (2004).
R. Schachar, et al., Cognitive and behavioral effects of multilayer-release methylphenidate in the treatment of children with attention-deficit/hyperactivity disorder, J. Child Adoles. Psychopharmacol., 18:11-24(2008).

(56) References Cited

OTHER PUBLICATIONS

I. Singh, et al, Ion-Exchange Resin Complexation: Masking the Bitter Taste of Cefuroxime Axetil, Revista Cubana de Fannacia, 45(2):171-180 (2011).

N. R. Srinivas, et al., Enantioselective pharmacokinetics and pharmacodynamics of dl-threo-methylphenidate in children with attention deficit hyperactivity disorder, Clin Phalmacol Ther, 52:561-568 (1992).

N. R. Srinivas, et al., Enantiomeric Drug Development: Issues, Considerations, and Regulatory Requirements, Journal of Pharmaceutical Sciences, 9: 1205-12 15 (2001).

J. Swanson, et al., Acute tolerance to methylphenidate in the treatment of attention deficit hyperactivity disorder in children, Clin. Pharm. & Therapeutics, 66(3):295-305 (1999).

Polymers for Controlled Drug Delivery (Peter J. Tarcha, ed., 1991), pp. 223.

The Pharmacopeia of the United States Twenty-fifth Revision {1151} Pharmaceutical Dosage Forms, 2213-25 (2002).

United States Pharmacopeia 32; The National Formulation 27, vol. 1:1-12 (May 1, 2009).

United States Pharmacopeia 32; The National Formulation 27, vol. 3:2949-2950 (May 1, 2009).

FDA approves first 24-hour liquid sustained-release drug, VerusMed (Dec. 7, 2009).

M. Vimala Devi & P. S. S. Krishna Babu, Ion-Exchange Resinates As Controlled Release Drug Delivery Systems, in Advances in Controlled and Novel Drug Delivery, edited by N. K. Jain, CBS Publishers & Distributors, New Delhi (2001).

Handbook of Pharmaceutical Excipients, 2nd ed., edited by A. Wade and P. J. Weller, American Pharmaceutical Association (1994), pp. 84-87, 123-125, 143-148, 215-216, 280-282, 294-298, 519-521, 562-563.

Y. Wang et al., In Vitro Dissolution and In Vivo Oral Absorption of Methylphenidate from a Bimodal Release Formulation in Healthy Volunteers, Biopharm. Drug Dispos. 25:91-98 (2004).

WHO Drug Information, 25(2):139-147 (Jun. 2011), pp. 99, 138-147.

T. Agnese, et al, Comparing Various plasticisers regarding their effect on methacrylic acid/ethyl acrylate copolymer, BASF, $9^{th}$ Central European Symposium on Pharmaceutical Technology, Sep. 20-23, 2012, Dubrovnik, Croatia.

T. A. Khan et al, Mechanical, Bioadhesive Strength and Biological Evaluations of Chitosan films for Wound Dressing, J Pharm Pharmaceut Sci, 3(3); 202-311 (2000).

ExAct, Excipients & Actives for Pharma, No. 12, Jun. 2004, pp. 1-12, published by BASF Aktiengesellschaft, multiple authors.

Quillichew, Center for Drug Evaluation and Research, Approval Parkage for Application No. 207960Origls000, approval date Dec. 4, 2015, Date created: Jul. 19, 2016; pp. 1-8, https://www.accessdata.fda.gov/drugsatfda docs/-nda/2015/207960Orig1s000Approv.pdf.

Quillichew, Center for Drug Evaluation and Research, Chemistry Review(s) for Application No. 207960Orig1s000, pp. 1-54, approval date Dec. 4, 2015, Date created: Jul. 19, 2016; https://www.accessdata.fda.gov/drugsatfda_docs/nda/2015/207960Orig1s000ChemR.pdf.

Quillichew, Center for Drug Evaluation and Research, Labeling for Application No. 207960Orig1s000, pp. 1-19, approval date Dec. 4, 2015, Date created: Jul. 19, 2016; https://www.accessdata.fda.gov/drugsatfda_docs/nda/2015/207960Orig1s000lbl.pdf.

Quillichew, NDA Approval, NDA 207960, pp. 1-5, approval date Dec. 4, 2015, Date created: Jul. 19, 2016; https://www.accessdata.fda.gov/drugsatfda_docs/nda/2015/207960Orig1s000TOC.cfm.

Quillichew, Center for Drug Evaluation and Research, Medical Review for Application No. 207960Orig1s000, pp. 1-78, approval date Dec. 4, 2015, Date created: Jul. 19, 2016; https://www.accessdata.fda.gov/-drugsatfda_docs/nda/2015/207960Orig1s000MedR.pdf.

Quillichew, Center for Drug Evaluation and Research, Summary Review for Application No. 207960Orig1s000, pp. 1-6, approval date Dec. 4, 2015, Date created: Jul. 19, 2016; https://www.accessdata.fda.gov/-drugsatfda docs/nda/2015/207960Orig1s000SumR.pdf.

Quillichew, Label, pp. 1-14, approval date Dec. 4, 2015, Date created: Jul. 19, 2016; https://www.accessdata.fda.gov/-drugsatfda_docs/nda/2015/207960Orig1s000TOC.cfm.

Quillichew, Center for Drug Evaluation and Research, Medical Review for Application Number, approval date Dec. 4, 2015, Date created: Jul. 19, 2016; pp. 1-10, https://www.accessdata.fda.gov/drugsatfda_docs/nda/2015/207960Orig1s000PharmR.pdf.

ASTM & ISO Test Methods for Measuring Properties, DuPont$T^M$ Tyvek®, Dupont USA, http://www.dupont.com/product-and-services/packaging-materials-solutions/pharmaceutical-packaging/branks/tyvek-steril-packaging/articles/measuring-pro..., pp. 1-4, accessed May 31, 2017.

T. Agnese et al, Benefiting from the additional Sustained Release Functionality of Polyvinyl Acetate Dispersion applied as Binder in Wet Granulation, $2^{nd}$ Conference in Innovation in Drug Delivery, Oct. 3-6, 2010; Aiz-enProvence, France; T-GEMP/MD307.

J Yuan et al, "Characterization of Cellulose Acetate Films: Formulation Effects on the Thermomechanical Properties and Permeability of Free Films and Coating Films", Pharmaceutical Technology, vol. 33, N 3, pp. 88-100 (2009).

L. Martin, et al., "Investigation of Cellulose Acetate Polymer Viscosity and Coating Solution Concentration on Performance of Push-Pull Osmotic Pump (PPOP) Tablets", Poster Reprint CRS 2012, CRS_2012_Missaghi_PPOP_visc_OYCA, Colorcon, http://www.colorcon.com/literature/-marketing/mr/Extended%20Release/POLYOX/English/CRS_Investigation-Cellulose-Acetate-Polymer.pdf.

Badawy et al., Microenvironmental pH Modulation in Solid Dosage Forms, Journal of Pharmaceutical Sciences, vol. 96(5):948-959, May 2007.

Bolourchian et al., pH-independent release of propranolol hydrochloride from HPMC-based matrices using organic acids, DARU, vol. 16(3):136-142, Dec. 2008.

fda.gov, Approval Letter and Reviews: App. No. 75-629 (Methylin® ER), Center for Drug Evaluation and Research, pp. 1-84, May 2000.

fda.gov, Briefing Information, FDA Center for Drug Evaluation and Research Advisory Committee for Pharmaceutical Science and Clinical Pharmacology, pp. 1-20, Apr. 2010.

fda.gov., Clinical Pharamacology and Biopharmaceutics Review(s), App. No. 202100 (Quillivant® XR), Center for Drug Evaluation and Research, pp. 1-40, Sep. 2012.

Pifferi et al., The cost benefit of enantiomeric drugs, Eur. J. of Drug Metab. Pharmacokinet., vol. 20(1):15-25, Jan. 1995.

World Health Organization (WHO), Quality Assurance Highlights, WHO Drug Information, vol. 25(3):221-230, Jan. 2011.

Zhu et al., Two CES1 Gene Mutations Lead to Dysfunctional Carboxylesterase 1 Activity in Man: Clinical Significance and Molecular Basis, The American Journal of Huan Genetics, vol. 82:1241-1248, Jun. 2008.

European Search Report dated Jan. 20, 2012 and issued in European Patent Application No. 11192711.7, pp. 1-4.

Examination Report dated Feb. 1, 2012 issued in European Patent Application No. 11192711.7, pp. 1-5.

Applicant's Response to Feb. 1, 2012 Examination Report filed for European Patent Application No. 11192711.7, dated Mar. 29, 2012, pp. 1-6.

Intention to Grant dated May 23, 2012 issued in European Patent Application No. 11192711.7, pp. 1-78.

Examination Report dated Nov. 26, 2008 issued in European Patent Application No. 07753217.4, pp. 1-2.

Applicant's Response to Nov. 26, 2008 Examination Report (Rules 161 and 162) filed for European Patent Application No. 07753217.4, dated Dec. 17, 2008, pp. 1-16.

Examination Report (Rules 161 and 162) dated Nov. 22, 2010 issued in European Patent Application No. 07753217.4, pp. 1-4.

Applicant's Response to Nov. 22, 2010 Examination Report issued in European Patent Application No. 07753217.4, dated Mar. 25, 2011, pp. 1-21.

Intention to Grant dated Jul. 1, 2011 issued in European Patent Application No. 07753217.4, pp. 1-74.

English translation of an Office Action dated Aug. 21, 2012 issued in Japanese Patent Application No. 2009-500494, pp. 1-9.

(56) References Cited

OTHER PUBLICATIONS

English translation of an Office Action dated Oct. 8, 2013 issued in Japanese Patent Application No. 2009-500494, pp. 1-2.
Correspondence from the agent regarding an Office Action dated Oct. 20, 2010 issued in Israeli Patent Application No. 194042, pp. 1-8.
Applicant's Response and English translation thereof to the Oct. 20, 2010 Office Action issued in Israeli Patent Application No. 194042, dated Apr. 5, 2011, pp. 1-7.
Office Action dated Mar. 18, 2013 issued Canadian Patent Application No. 2,645,855, pp. 1-3.
Applicant's Response to Mar. 18, 2013 Office Action filed for Canadian Patent Application No. 2,645,855, dated Sep. 18, 2013, pp. 1-54.
Office Action dated Dec. 9, 2013 issued Canadian Patent Application No. 2,645,855, pp. 1-12.
Response to Dec. 9, 2013 Office Action filed for Canadian Patent Application No. 2,645,855, dated Jun. 9, 2014, pp. 1-41.
Examination Report dated Mar. 11, 2014 issued in Indian Patent Application No. 8703/DELNP/2008, pp. 1-6.
Response to Mar. 11, 2014 Examination Report filed for Indian Patent Application No. 8703/DELNP/2008, dated Dec. 30, 2014, pp. 1-14.
First Examiner's Report dated Nov. 28, 2011 issued in Australian Patent Application No. 2007227569, pp. 1-3.
Applicant's Response to the Nov. 28, 2011 First Examiner's Report filed for Australian Patent Application No. 2007227569, dated Aug. 5, 2013, pp. 1-30.
Office Action and English translation thereof dated Jan. 28, 2011 issued in Russian Federation Patent Application No. 2008140944, pp. 1-9.
English translation of a First Office Action dated Feb. 6, 2013 issued in Chinese Patent Application No. 201110371263.X, pp. 1-9.
English translation of a Second Office Action dated Oct. 24, 2013 issued in Chinese Patent Application No. 201110371263.X, pp. 1-9.
English translation of a First Office Action dated Apr. 30, 2010 issued in Chinese Patent Application No. 200780009208.8, pp. 1-4.
English translation of a Notification of Grounds of Refusal dated Aug. 25, 2013 issued in Korean Patent Application No. 10-2008-7024357, pp. 1-8.
English translation of a Notification of Grounds of Refusal dated Apr. 4, 2014 issued in Korean Patent Application No. 10-2008-7024357, pp. 1-6.
Office Action dated Oct. 22, 2019 issued on Brazilian Patent Application No. PI0709606-2, pp. 1-5.
Office Action dated Nov. 12, 2009 issued in U.S. Appl. No. 11/724,966, pp. 1-24.
Applicant's Response to the Office Action dated Nov. 12, 2009 issued in U.S. Appl. No. 11/724,966, pp. 1-26.
Interview Summary dated Mar. 17, 2010 issued in U.S. Appl. No. 11/724,966, pp. 1-3.
Applicant's Response to Interview Summary dated Mar. 17, 2010 issued in U.S. Appl. No. 11/724,966, pp. 1-9.
Office Action dated Jun. 23, 2010 issued in U.S. Appl. No. 11/724,966, pp. 1-14.
Applicant's Response to the Office Action dated Jun. 23, 2010 issued in U.S. Appl. No. 11/724,966, pp. 1-79.
Office Action dated Nov. 26, 2010 issued in U.S. Appl. No. 11/724,966, pp. 1-15.
Applicant's Response to the Office Action dated Nov. 26, 2010 issued in U.S. Appl. No. 11/724,966, pp. 1-91.
Rule 131 Declaration executed by Drs. Mehta and Tu filed Sep. 23, 2010 in U.S. Appl. No. 11/724,966, pp. 1-54.
Rule 132 Declaration executed by Dr. Tu filed May 25, 2011 in U.S. Appl. No. 11/724,966, pp. 1-35.
Rule 132 Declaration executed by Dr. Kibbe filed May 25, 2011 in U.S. Appl. No. 11/724,966, pp. 1-29.
Notice of Allowance dated Aug. 19, 2011 issued in U.S. Appl. No. 11/724,966, pp. 1-10.
Office Action dated Dec. 9, 2011 issued in U.S. Appl. No. 12/722,857, pp. 1-18.
Applicant's Response to the Office Action dated Dec. 9, 2011 issued in U.S. Appl. No. 12/722,857, pp. 1-19.
Notice of Allowance dated Aug. 30, 2012 issued in U.S. Appl. No. 12/722,857, pp. 1-8.
Office Action dated Dec. 9, 2011 issued in U.S. Appl. No. 13/244,748, pp. 1-65.
Applicant's Response to the Office Action dated Dec. 9, 2011 issued in U.S. Appl. No. 13/244,748, pp. 1-38.
Notice of Allowance dated Apr. 27, 2012 issued in U.S. Appl. No. 13/244,748, pp. 1-16.
Office Action dated Jan. 18, 2013 issued in U.S. Appl. No. 13/666,424, pp. 1-27.
Applicant's Response to the Office Action dated Jan. 18, 2013 issued in U.S. Appl. No. 13/666,424, pp. 1-15.
Notice of Allowance dated May 17, 2013 issued in U.S. Appl. No. 13/666,424, pp. 1-10.
Office Action dated Mar. 21, 2013 issued in U.S. Appl. No. 13/746,654, pp. 1-22.
Applicant's Response to the Office Action dated Mar. 21, 2013 issued in U.S. Appl. No. 13/746,654, pp. 1-139.
Notice of Allowance dated Jul. 31, 2013 issued in U.S. Appl. No. 13/746,654, pp. 1-10.
Office Action dated Nov. 21, 2013 issued in U.S. Appl. No. 14/044,105, pp. 1-15.
Applicant's Response to the Office Action dated Nov. 21, 2013 issued in U.S. Appl. No. 14/044,105, pp. 1-15.
Applicant Initiated Interview Summary dated May 13, 2014 issued in U.S. Appl. No. 14/044,105, p. 1.
Notice of Allowance dated May 13, 2014 issued in U.S. Appl. No. 14/044,105, pp. 1-10.
Office Action dated Dec. 5, 2013 issued in U.S. Appl. No. 14/065,842, pp. 1-18.
Applicant's Response to the Office Action dated Dec. 5, 2013 issued in U.S. Appl. No. 14/065,842, pp. 1-10.
Notice of Allowance dated Apr. 9, 2014 issued in U.S. Appl. No. 14/065,842, pp. 1-10.
Office Action dated Feb. 26, 2014 issued in U.S. Appl. No. 14/155,410, pp. 1-16.
Applicant's Response to the Office Action dated Feb. 26, 2014 issued in U.S. Appl. No. 14/155,410, pp. 1-10.
Notice of Allowance issued on U.S. Appl. No. 14/155,410, dated Jul. 21, 2014, pp. 1-12.
Office Action issued on U.S. Appl. No. 14/508,613, dated Mar. 29, 2016, and Response.
Notice of Allowance issued on U.S. Appl. No. 14/508,613, dated Dec. 23, 2016.
Office Action issued on U.S. Appl. No. 15/383,474, dated Jul. 14, 2017 and Response.
Final Office Action issued on U.S. Appl. No. 15/383,474, dated Feb. 21, 2018 and Response.
Notice of Allowance issued on U.S. Appl. No. 15/383,474, dated Nov. 27, 2018.
Notice of Allowance issued on U.S. Appl. No. 16/241,287, dated Apr. 22, 2020.
Notice of Allowance issued on U.S. Appl. No. 16/241,287, dated Apr. 14, 2020.
Rule 312 Amendment filed on U.S. Appl. No. 16/241,287, dated Mar. 10, 2020 and Response dated Mar. 23, 2020.
Notice of Allowance issued on U.S. Appl. No. 16/241,287, dated Jan. 28, 2020.
Office Action dated Jul. 11, 2019 issued on U.S. Appl. No. 16/241,287, and Response dated Dec. 11, 2019 with Declaration of Dr. Yu-Hsing Tu, dated Jun. 1, 2012.
Office Action issued on U.S. Appl. No. 16/719,121, dated Jun. 1, 2020, and Response dated Sep. 1, 2020.
Notice of Allowance issued on U.S. Appl. No. 16/719,121, dated Oct. 21, 2020.
Office Action issued on U.S. Appl. No. 14/735,526, dated Aug. 27, 2015 and Response.
Notice of Allowance issued on U.S. Appl. No. 14/735,526, dated Oct. 13, 2015.

(56) References Cited

OTHER PUBLICATIONS

Office Action issued on U.S. Appl. No. 14/735,526, dated Apr. 21, 2016 and Response.
Notice of Allowance issued on U.S. Appl. No. 15/047,388, dated Dec. 19, 2016.
Final Office Action issued on U.S. Appl. No. 15/200,617, dated Aug. 21, 2017.
Office Action issued on U.S. Appl. No. 15/200,617, dated Sep. 22, 2016 and Response.
Office Action issued on U.S. Appl. No. 15/200,748, dated Sep. 22, 2016 and Response.
Notice of Allowance issued on U.S. Appl. No. 15/200,748, dated Apr. 11, 2017.
Corrected Notice of Allowance issued on U.S. Appl. No. 15/200,748, dated May 3, 2017.
Office Action issued on U.S. Appl. No. 15/200,786, dated Sep. 22, 2016 and Response.
Notice of Allowance issued on U.S. Appl. No. 15/200,786, dated Apr. 10, 2017.
Corrected Notice of Allowance issued on U.S. Appl. No. 15/200,786, dated May 3, 2017.
Office Action issued on U.S. Appl. No. 15/619,637, dated Jul. 11, 2017.
Final Office Action issued on U.S. Appl. No. 15/619,637, dated Nov. 17, 2017 and Response.
Notice of Allowance issued on U.S. Appl. No. 15/619,637, dated Aug. 15, 2018.
Corrected Notice of Allowance issued on U.S. Appl. No. 15/619,637, dated Sep. 6, 2018.
Final Office Action issued on U.S. Appl. No. 15/706,234, dated May 17, 2018.
Office Action issued on U.S. Appl. No. 15/706,234, dated Oct. 31, 2017 and Response.
Final Office Action issued on U.S. Appl. No. 16/249,415, dated Sep. 19, 2019.
Office Action issued on U.S. Appl. No. 16/249,415, dated Feb. 25, 2019, and Response dated Aug. 21, 2019.
Office Action issued on related Israeli Patent Application No. 227734, dated Nov. 1, 2016.
Examination Report dated Sep. 24, 2013 issued in European Patent Application No. 11705137.5, pp. 1-2.
Applicant's Response to Sep. 24, 2013 Examination Report filed for European Patent Application No. 11705137.5, dated Mar. 10, 2014, pp. 1-17.
Observations by Third Parties dated Sep. 15, 2014 issued in European Patent Application No. 11705137.5, pp. 1-10.
Communication dated Sep. 22, 2014 issued in European Patent Application No. 11705137.5, pp. 1-36.
Applicant's Response to the Sep. 22, 2014 Communication filed for European Patent Application No. 11705137.5, dated Nov. 10, 2014, pp. 1-12.
Examination Report dated Jul. 21, 2015 issued in European Patent Application No. 11705137.5, pp. 1-5.
Applicant's Response to the Jul. 21, 2015 Examination Report filed for European Patent Application No. 11705137.5, dated Oct. 27, 2015, pp. 1-39.
Communication pursuant to Article 94(3) EPC issued on European Patent Application No. 11705137.5, dated Aug. 19, 2016, and Response.
Intent to Grant issued on European Patent Application No. 11705137.5, dated Oct. 12, 2018.
Amendment filed for Australian Patent Application No. 2011359405, dated Nov. 25, 2015, pp. 1-30.
Examination Report dated May 19, 2016 issued on Australian Patent Application No. 2011359405.
Examination Report dated Feb. 12, 2018, issued on Australian Patent Application No. 2017202955.
Examination Report issued on Canadian Patent Application No. 2,825,991, dated Feb. 10, 2017.
Examination Report issued on Canadian Patent Application No. 2,825,991, dated Oct. 2, 2017.
Office Action dated Dec. 23, 2011 issued in U.S. Appl. No. 13/244,706, pp. 1-27.
Applicant's Response Office Action dated Dec. 23, 2011 issued in U.S. Appl. No. 13/244,706, pp. 1-127.
Office Action dated Jun. 15, 2012 issued in U.S. Appl. No. 13/244,706, pp. 1-19.
Applicant's Response to the Office Action dated Jun. 15, 2012 issued in U.S. Appl. No. 13/244,706, pp. 1-18.
Notice of Allowance dated Aug. 13, 2012 issued in U.S. Appl. No. 13/244,706, pp. 1-11.
Office Action dated Nov. 9, 2012 issued in U.S. Appl. No. 13/611,183, pp. 1-10.
Applicant's Response to the Office Action dated Nov. 9, 2012 issued in U.S. Appl. No. 13/611,183, dated Jan. 10, 2013, pp. 1-26.
Rule 132 Declaration executed by Dr. Tu filed Jan. 10, 2013 in U.S. Appl. No. 13/611,183, pp. 1-10.
Notice of Allowance dated May 10, 2013 issued in U.S. Appl. No. 13/611,183, pp. 1-13.
Notice of Allowance dated Aug. 2, 2013 issued in U.S. Appl. No. 13/905,808, pp. 1-16.
Office Action dated Nov. 21, 2013 issued in U.S. Appl. No. 14/016,384, pp. 1-12.
Applicant's Response to the Office Action dated Nov. 21, 2013 issued in U.S. Appl. No. 14/016,384, pp. 1-15.
Notice of Allowance issued on U.S. Appl. No. 14/016,384, dated May 9, 2014, pp. 1-8.
Notice of Allowance issued on U.S. Appl. No. 14/299,421, dated Dec. 19, 2014.
Declaration Pursuant to 37 CFR 1.132 filed for U.S. Appl. No. 14/554,123, dated Mar. 4, 2012.
Applicant-Initiated Interview Summary filed for U.S. Appl. No. 14/554,123, dated Feb. 6, 2015.
Office Action issued on U.S. Appl. No. 14/554,123, dated Jan. 7, 2015 and Response.
Notice of Allowance issued on U.S. Appl. No. 14/554,123, dated Apr. 15, 2015.
Corrected Notice of Allowance issued on U.S. Appl. No. 14/554,123, dated Apr. 20, 2015.
Office Action issued on U.S. Appl. No. 14/657,151, dated Apr. 24, 2015 and Response.
Final Office Action issued on U.S. Appl. No. 14/657,151, dated Sep. 24, 2015 and Response.
Advisory Action and Examiner-Initiated Interview Summary issued on U.S. Appl. No. 14/657,151, dated Dec. 15, 2015.
Office Action issued on U.S. Appl. No. 15/215,276, dated Sep. 25, 2017.
Office Action issued on U.S. Appl. No. 15/244,430, dated Sep. 22, 2017.
Communication Pursuant to Rules 161(1) & 162 EPC, dated Apr. 21, 2015, issued on counterpart European Patent Application No. 13752782.6, pp. 1-6.
Applicant's Response to Apr. 21, 2015 Communication issued on European Patent Application No. 13752782.6, dated Oct. 23, 2015, pp. 1-24.
Examination Report issued on Australian Patent Application No. 2013302657, dated Sep. 8, 2017.
Office Action issued on Brazilian Patent Application No. BR112015003120-0, dated Oct. 13, 2020.
Office Action issued on Canadian Patent Application No. 2,880,456, dated Jul. 9, 2019.
Office Action issued on Canadian Patent Application No. 2,880,456, dated Apr. 9, 2020.
Office Action issued on Israeli Patent Application No. 236847, dated Aug. 10, 2017 and Response.
Non-Final Office Action dated Aug. 1, 2014 issued on U.S. Appl. No. 14/300,580, pp. 1-7.
Response to Aug. 1, 2014 Office Action filed for U.S. Appl. No. 14/300,580, dated Oct. 17, 2014, pp. 1-14.
Notice of Allowance dated Feb. 11, 2015 issued on U.S. Appl. No. 14/300,580, pp. 1-7.
No OAs issued.

(56) References Cited

OTHER PUBLICATIONS

Non-Final Office Action dated Apr. 1, 2015 issued on U.S. Appl. No. 14/624,998, pp. 1-10.
Response to Apr. 1, 2015 Office Action filed for U.S. Appl. No. 14/624,998, dated Jun. 26, 2015, pp. 1-14.
Notice of Allowance dated Sep. 3, 2015 issued on U.S. Appl. No. 14/624,998, pp. 1-8.
Non-Final Office Action dated Nov. 10, 2015 issued on U.S. Appl. No. 14/872,226, pp. 1-6.
Response to Nov. 10, 2015 Office Action filed for U.S. Appl. No. 14/872,226, dated Nov. 24, 2015, pp. 1-8.
Notice of Allowance dated Jan. 12, 2016 issued on U.S. Appl. No. 14/872,226, pp. 1-5.
Non-Final Office Action dated Aug. 10, 2016 issued on U.S. Appl. No. 15/009,468, pp. 1-7.
Response to Aug. 10, 2016 Office Action issued on U.S. Appl. No. 15/009,468, pp. 1-8.
Notice of Allowance dated Mar. 21, 2017 issued on U.S. Appl. No. 15/009,468, pp. 1-5.
Non-Final Office Action dated Sep. 9, 2016 issued on U.S. Appl. No. 15/200,625, pp. 1-8.
Response to Sep. 9, 2016 Office Action issued on U.S. Appl. No. 15/200,625, dated Sep. 14, 2016, pp. 1-11.
Notice of Allowance dated Nov. 18, 2016 issued on U.S. Appl. No. 15/200,625, pp. 1-5.
Non-Final Office Action dated Apr. 6, 2020 issued on U.S. Appl. No. 16/700,517 and Response dated Sep. 8, 2020, pp. 1-24.
Notice of Allowance dated Oct. 7, 2020 issued on U.S. Appl. No. 16/700,517.
No actions as of Mar. 23, 2021 (filed Oct. 2020).
Non-Final Office Action dated Jan. 29, 2021 issued on U.S. Appl. No. 17/113,856 and Response dated Feb. 2, 2021.
Notice of Allowance dated Mar. 4, 2021 issued on U.S. Appl. No. 17/113,856.
Notice of Allowance dated Jan. 9, 2019 issued on U.S. Appl. No. 15/258,695.
Non-Final Office Action dated Jun. 28, 2018 issued on U.S. Appl. No. 15/258,695 and Response dated Nov. 28, 2018.
Applicant-Initiated Interview Summary filed for U.S. Appl. No. 15/258,695, dated May 16, 2018.
Final Office Action dated Dec. 22, 2017 issued on U.S. Appl. No. 5/258,695 and Response dated Feb. 23, 2018.
Non-Final Office Action dated Apr. 21, 2017 issued on U.S. Appl. No. 15/258,695 and Response dated Sep. 19, 2017.
Examiner-Initiated Interview Summary dated Aug. 29, 2017 issued on U.S. Appl. No. 15/258,695.
Notice of Allowance dated Jan. 9, 2020 issued on U.S. Appl. No. 15/258,700.
Advisory Action dated Sep. 13, 2018 issued on U.S. Appl. No. 15/258,700.
Final Office Action dated May 16, 2018 issued on U.S. Appl. No. 15/258,700, and Response dated Aug. 8, 2018.
Applicant-Initiated Interview Summary dated May 10, 2018 issued on U.S. Appl. No. 15/258,700.
Non-Final Office Action dated Aug. 23, 2017 issued on U.S. Appl. No. 15/258,700, and Response dated Feb. 23, 2017.
Non-Final Office Action issued on U.S. Appl. No. 16/376,631, dated Oct. 5 2020.
Complaint by Tris Pharma, Inc. against Actavis Laboratories FL, Inc. et al., C.A. No. 14-1309-GMS, dated Oct. 15, 2014, pp. 1-17.
Defendant Actavis Laboratories FL, Inc.'s Answer, Defenses, and Counterclaims, C.A. No. 14-1309-GMS, dated Dec. 5, 2014, pp. 1-24.
Answer to Actavis Laboratories FL, Inc.'s Counterclaims, C.A. No. 14-1309-GMS, dated Dec. 29, 2014, pp. 1-7.
First Amended Complaint, C.A. No. 14-1309-GMS, dated May 22, 2015, pp. 1-22.
Defendant Actavis Laboratories FL, Inc.'s Initial Invalidity Contentions, C.A. No. 14-1309-GMS, dated May 27, 2015, pp. 1-152.
Defendants Par Pharmaceutical, Inc.'s and Par Pharmaceutical Companies, Inc.'s Initial Invalidity Contentions, C.A. No. 14-1309-GMS, dated Jun. 10, 2015, pp. 1-199.
Defendants Par Pharmaceutical, Inc.'s and Par Pharmaceutical Companies, Inc.'s Answer to First Amended Complaint and Counterclaims, C.A. No. 14-1309-GMS, dated Jun. 12, 2015, pp. 1-49.
Defendant's Par Pharmaceutical, Inc.'s and Par Pharmaceutical Companies, Inc.'s Answer to Second Amended Complaint and Counterclaims, C.A. No. 14-1309-GMS, dated Aug. 24, 2015, pp. 1-57.
Joint Claim Construction Statement and Chart, C.A. No. 14-1309-GMS, dated Sep. 30, 2015, pp. 1-13.
Defendant's Opening Claim Construction Brief, C.A. No. 14-1309-GMS, dated Oct. 30, 2015, pp. 1-15.
Supplemental Joint Claim Construction Brief, C.A. No. 14-1309-GMS, dated Oct. 30, 2015, pp. 1-2.
Tris's Opening Claim Construction Brief, C.A. No. 14-1309-GMS, dated Oct. 30, 2015, pp. 1-21.
Defendant Actavis Laboratories FL, Inc.'s Amended Initial Invalidity Contentions, C.A. No. 14-1309-GMS, dated Jan. 22, 2016, pp. 1-198.
Defendant Actavis Laboratories FL, Inc.'s Final Invalidity Contentions, C.A. No. 14-1309-GMS, dated Feb. 8, 2016, pp. 1-203.
Exhibit C: Materials Considered in Expert Report by Richard Christian Moreton, C.A. No. 14-1309-GMS, dated May 3, 2016, pp. 1-3.
Exhibit B: Materials Considered in Expert Report by Jud Staller, M.D., C.A. No. 14-1309-GMS, dated May 3, 2016, pp. 1-2.
Exhibit B: Materials Considered in Expert Report by Arthur B. Straughn, Pharm.D., C.A. No. 14-1309-GMS, dated May 3, 2016, pp. 1-2.
List of Exhibits in Responding Expert Report by Dr. C. Lindsay DeVane, C.A. No. 14-1309-GMS, dated Jun. 21, 2016, pp. 1-5.
List of Exhibits in Responding Expert Report by James John McGough, M.D., M.S., C.A. No. 14-1309-GMS, dated Jun. 21, 2016, pp. 1-5.
List of Exhibits in Responding Expert Report by Dr. Irwin Jacobs, C.A. No. 14-1309-GMS, dated Jun. 21, 2016, pp. 1-6.
*Tris Pharma, Inc.* v. *Actavis Laboratories FL, Inc.*, Tris's Proposed Post-Trial Findings of Fact and Conclusions of Law, C.A. No. 14-1309-GMS, Mar. 24, 2017.
*Tris Pharma, Inc.* v. *Actavis Laboratories FL, Inc.*, Defendant's Post-Trial Findings of Fact and Conclusions of Law, C.A. No. 14-1309-GMS, Mar. 24, 2017.
*Tris Pharma, Inc.* v. *Actavis Laboratories FL, Inc.*, Memorandum and Opinion, C.A. No. 14-1309-GMS, Sep. 5, 2017.
*Tris Pharma, Inc.* v. *Actavis Laboratories FL, Inc.*, Appeal Brief for Plaintiff-Appellant, C.A. No. 14-1309-GMS, Dec. 4, 2017.
*Tris Pharma, Inc.* vs *Actavis Laboratories FL, Inc.*, C.A. Nos. 14-1309-GMS, 15-969-GMS, and 15-393-GMS, "Response Brief for the Defendant-Appellee", dated Feb. 15, 2018.
*Tris Pharma, Inc.* v. *Actavis Laboratories FL, Inc.*, Reply Brief for Plaintiff-Appellant, C.A. No. 14-1309-GMS, Mar. 15, 2018.
*Tris Pharma, Inc.* v. *Actavis Laboratories FL, Inc.*, Memorandum Opinion, C.A. No. 14-1309-CFC, Nov. 30, 2020.
Complaint by Tris Pharma, Inc. against Par Pharmaceutical, Inc. et al., C.A. No. 15-0068-GMS, dated Jan. 21, 2015, pp. 1-21.
Defendants Par Pharmaceutical, Inc.'s and Par Pharmaceutical Companies, Inc.'s Answer to Complaint and Counterclaims, C.A. No. 15-0068-GMS, dated Feb. 12, 2015, pp. 1-38.
Answer to Par Pharmaceutical, Inc.'s and Par Pharmaceutical Companies, Inc.'s Counterclaims, C.A. No. 15-0068-GMS, dated Feb. 26, 2015, pp. 1-10.
Complaint by Tris Pharma, Inc. against Actavis Laboratories FL, Inc., et al., C.A. No. 15-393-GMS, dated May 15, 2015, pp. 1-10.
Defendant Actavis Laboratories FL, Inc.'s Answer, Affirmative Defenses, and Counterclaims, C.A. No. 15-393-GMS, dated Jun. 12, 2015, pp. 1-15.
Complaint by Tris Pharma, Inc. against Actavis Elizabeth LLC and Actavis, Inc., C.A. No. 16-603-GMS, dated Jul. 12, 2016.
Defendants Actavis Elizabeth LLC and Actavis Inc.'s Answer, Defenses, and Counterclaims, C.A. No. 16-603-GMS, dated Sep. 2, 2016.

(56) References Cited

OTHER PUBLICATIONS

Tris Answer to Defendants Actavis and Actavis Elizabeth LLC's Counterclaims, *Tris Pharma, Inc., v. Actavis Elizabeth LLC,* C.A. No. 16-603-GMS In the United States District Court for the District of Delaware, Document 13, Filed Sep. 26, 2016, pp. 1-15.

First Amended Complaint, *Tris Pharma, Inc., v. Actavis Elizabeth LLC,* C.A. No. 16-603-GMS In the United States District Court for the District of Delaware, Document 32, Filed Apr. 25, 2017, pp. 1-11.

Defendants Actavis and Actavis Elizabeth LLC's Answer and Defenses, and Actavis Elizabeth LLC's Counterclaims to Plaintiff's First Amended Complaint, *Tris Pharma, Inc., v. Actavis Elizabeth LLC,* C.A. No. 16-603-GMS In the United States District Court for the district of Delaware, Document 35, Filed Apr. 25, 2017, pp. 1-15.

Tris' Answer to Defendant Actavis Elizabeth's Counterclaims, *Tris Pharma, Inc., v. Actavis Elizabeth LLC,* C.A. No. 16-603-GMS In the United States District Court for the District of Delaware, Document 39, Filed May 9, 2017, pp. 1-8.

Defendant Actavis Elizabeth LLC's Initial Invalidity Contentions, *Tris Pharma, Inc., v. Actavis Elizabeth LLC,* C.A. No. 16-603-GMS In the United States District Court for the District of Delaware, pp. 1-111, May 17, 2017.

*Tris Pharma, Inc. vs. Actavis Elizabeth LLC,* C.A. No. 16-603-GMS, "Order Construing the terms of U.S. Pat. No. 9,545,399", dated Feb. 20, 2018.

Second Amended Complaint for Patent Infringement against Actavis Elizabeth LLC—filed by Tris Pharma Inc., C.A. No. 16-603-GMS, entered Mar. 20, 2018.

Answer to Amended Complaint, re: 120 Amended Complaint Affirmative Defenses and, Counterclaim against Tris Pharma Inc. by Actavis Elizabeth LLC., C.A. No. 16-603-GMS, entered Mar. 28, 2018.

Complaint by Tris Pharma, Inc. against Teva Pharmaceuticals USA, Inc., C.A. No. 2:20-cv-05212-KM-JBC, dated Apr. 28, 2020.

Defendant Teva Pharmaceuticals USA, Inc.'s Answer, Affirmative Defenses, and Counterclaims to Plaintiff's Complaint, C.A. No. 2:20-cv-05212-KM-JBC, dated Jun. 29, 2020.

Answer to the Defendant Teva's Counterclaims, C.A. No. 2:20-cv-05212-KM-JBC, dated Jul. 20, 2020.

Defendant Teva Pharmaceuticals USA, Inc.'s Initial Invalidity Contentions, dated Oct. 6, 2020, *Tris Pharma, Inc, v. Teva Pharmaceuticals USA, Inc,* In the United States District Court for the District of New Jersey, C.A. No. 20-cv-05212-KM-JBC, pp. 1-239.

Notice of Paragraph IV Certification from Actavis, dated Sep. 3, 2014 and "Detailed Factual and Legal Bases for Actavis's Paragraph IV Certification that U.S. Pat. No. 8,062,667; U.S. Pat. No. 8,287,903; U.S. Pat. No. 8,465,765; U.S. Pat. No. 8,563,033; and U.S. Pat. No. 8,778,390 are Invalid, Unenforceable, and/or Not Infringed", pp. 1-23.

Notice of Paragraph IV Certification from Par Pharmaceuticals, dated Dec. 22, 2014, and "Detailed Statement of the Factual and Legal Bases for Par's Opinion that U.S. Pat. No. 8,062,667; U.S. Pat. No. 8,287,903; U.S. Pat. No. 8,465,765; U.S. Pat. No. 8,563,033; and U.S. Pat. No. 8,778,390 are Invalid, Unenforceable, and/or Not Infringed", pp. 1-69.

Notice of Paragraph IV Certification from Par Pharmaceuticals, dated Apr. 2, 2015, and "Detailed Statement of the Factual and Legal Bases for Par's Opinion that U.S. Pat. No. 8,956,649 is Invalid, Unenforceable, and/or Will Not Be Infringed", pp. 1-28.

Notice of Paragraph IV Certification from Par Pharmaceuticals, dated Jun. 17, 2015, and "Detailed Statement of the Factual and Legal Bases for Par's Opinion that U.S. Pat. No. 9,040,083 is Invalid, Unenforceable, and/or Will Not Be Infringed", pp. 1-24.

Notice of Paragraph IV Certification from Actavis, dated Sep. 9, 2015, and "Detailed Factual and Legal Bases for Actavis's Paragraph IV Certification that U.S. Pat. No. 9,040,083 Is Invalid, Unenforceable and/or Not Infringed", pp. 1-19, dated Sep. 9, 2015.

Notification of Certification for U.S. Pat. No. 8,202,537; U.S. Pat. No. 8,287,903; U.S. Pat. No. 8,999,386; and 9,295,642 Pursuant to § 505(j)(2)(B)(iv) of the Federal Food, Drug, and Cosmetic Act, pp. 1-22, dated Jun. 2, 2016.

Notification of Certification for U.S. Pat. No. 9,545,399 Pursuant to § 505(j)(2)(B)(iv) of the Federal Food, Drug, and Cosmetic Act with Actavis' Detailed Factual and Legal Basis for Its Paragraph IV Certification that U.S. Pat. No. 9,545,399 Is Invalid, Unenforceable and/or Not Infringed by the Methylphenidate Hydrochloride Products Described in Actavis' ANDA No. 209134, dated Mar. 10, 2017.

International Search Report and Written Opinion dated Oct. 21, 2013 and issued in International Patent Application No. PCT/US2013/054930, pp. 1-4.

International Search Report and Written Opinion dated Oct. 1, 2007 and issued in International Patent Application No. PCT/US2007/006572, pp. 1-4.

International Search Report and Written Opinion dated Feb. 22, 2012 and issued in International Patent Application No. PCT/US2011/024873, pp. 1-4.

English abstract for Japanese Patent Publication No. 02-172912 dated Jul. 4, 1990, p. 1.

English abstract for Japanese Patent Publication No. 5-279247 dated Dec. 26, 1993, pp. 1-3.

English abstract for Japanese Patent Publication No. 2005-306778 dated Nov. 4, 2005, pp. 1-3.

English abstract for Japanese Patent Publication No. 2003-528910 dated Sep. 30, 2003, p. 1.

Set of claims filed on Mar. 18, 2014 in U.S. Appl. No. 13/844,555, pp. 1-3.

Set of claims filed on May 2, 2014 in U.S. Appl. No. 13/844,537, pp. 1-5.

Set of claims filed on Mar. 18, 2014 in U.S. Appl. No. 13/844,510, pp. 1-3.

Report on the Filing or Determination of an Action Regarding a Patent or Trademark dated Oct. 15, 2014, p. 1.

Declaration Under 37 C.F.R. Section 1.132 filed in U.S. Pat. No. 8,465,768, dated Jul. 6, 2012.

fda.gov, Chemistry Reviews—Application No. 208147 (Dyanavel®), Center for Drug Evaluation and Research, pp. 1-47, Aug. 18, 2015 (date created: Jun. 30, 2016), retrieved from https://www.accessdata.fda.gov/drugsatfda_docs/nda/2015/208147Orig1DyanavelTOC.cfm.

fda.gov, NDA Approval Letter—Application No. 208147 (Dyanavel®), Center for Drug Evaluation and Research, pp. 1-6, Oct. 19, 2015 (date created: Jun. 30, 2016), retrieved from https://www.accessdata.fda.gov/drugsatfda_docs/nda/2015/208147Orig1DyanavelTOC.cfm.

fda.gov, Medical Reviews—Application No. 208147 (Dyanavel®), Center for Drug Evaluation and Research, pp. 1-18, Oct. 19, 2015 (date created: Jun. 30, 2016), retrieved from https://www.accessdata.fda.gov/drugsatfda_docs/nda/2015/208147Orig1DyanavelTOC.cfm.

fda.gov, Other Review(s)—Application No. 208147 (Dyanavel®), Center for Drug Evaluation and Research, pp. 1-97, Feb. 24, 2015 (date created: Jun. 30, 2016), retrieved from https://www.accessdata.fda.gov/drugsatfda_docs/nda/2015/208147Orig1DyanavelTOC.cfm.

fda.gov, Pharmacology Review(s)—Application No. 208147 (Dyanavel®), Center for Drug Evaluation and Research, pp. 1-9 (date created: Jun. 30, 2016), retrieved from https://www.accessdata.fda.gov/drugsatfda_docs/nda/2015/208147Orig1DyanavelTOC.cfm.

fda.gov, Summary Reivew—Application No. 208147 (Dyanavel®), Center for Drug Evaluation and Research, pp. 1-6, Oct. 19, 2015 (date created: Jun. 30, 2016), retrieved from https://www.accessdata.fda.gov/drugsatfda_docs/nda/2015/208147Orig1DyanavelTOC.cfm.

Certification of Non-Infringement and/or Invalidity of U.S. Pat. No. 8,202,537; U.S. Pat. No. 8,287,903; U.S. Pat. No. 8,999,386; U.S. Pat. No. 9,295,642; U.S. Pat. No. 9,844,544; and U.S. Pat. No. 10,857,143, dated May 10, 2021.

(56) References Cited

OTHER PUBLICATIONS

Opening Brief for the Defendant-Appellant, *Tris Pharma, Inc.* v. *Actavis Laboratories FL, Inc.*, C.A. No. 1:14-cv-1309-CFV, pp. 1-213, Apr. 7, 2021.

Corrected Opening Brief for the Defendant-Appellant, *Tris Pharma, Inc.* v. *Actavis Laboratories FL, Inc.*, C.A. Nos. 14-1309-CFC, 15-393-CFC, 15-969-CFC, pp. 1-213, Apr. 16, 2021.

Tris Pharma Inc.'s Opening Claim Construction Brief, *Tris Pharma, Inc.* v. *Teva Pharmaceuticals USA, Inc.*, C.A. No. 20-cv-05212-KM-ESK, pp. 1-48, Apr. 13, 2021.

Notice of Motion to Seal and Proposed Findings of Fact and Conclusions of Law in Support of Motion to Seal, *Tris Pharma, Inc.* v. *Teva Pharmaceuticals USA, Inc.*, C.A. No. 2:20-cv-05212, pp. 1-25, May 11, 2021.

[Corrected] Defendant's Responsive Claim Construction Brief, *Tris Pharms, Inc.* v. *Teva Pharmaceuticals USA, Inc.*, C.A. No. 2-20-cv-05212-KM-JBC, pp. 1-35, Jun. 7, 2021.

Tris Pharma, Inc.'s Responsive Claim Construction Brief, *Tris Pharma, Inc.* v. *Teva Pharmaceuticals USA, Inc.*, C.A. No. 20-cv-05212-KM-ESK, pp. 1-46, Jun. 4, 2021.

\* cited by examiner

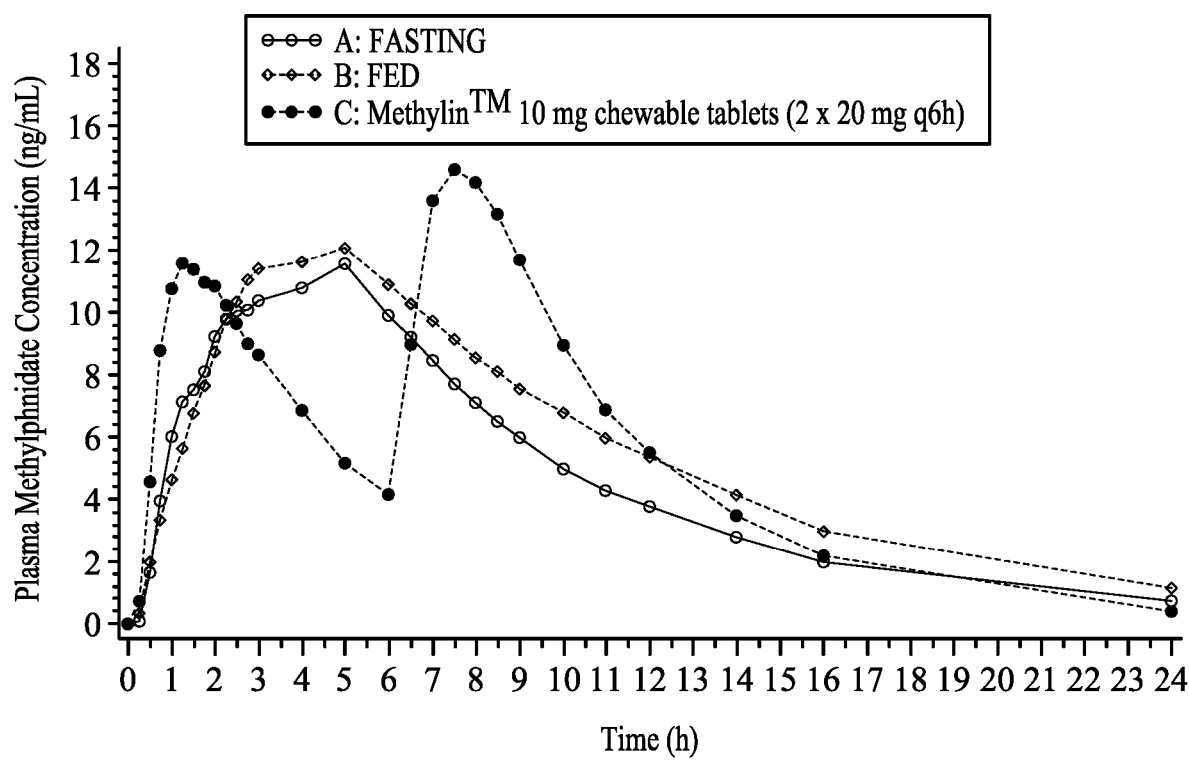

METHYLPHENIDATE EXTENDED RELEASE CHEWABLE TABLET

BACKGROUND OF THE INVENTION

Methylphenidate hydrochloride (HCl) and dexmethylphenidate hydrochloride both have the empirical formula $C_{14}H_{19}NO_2 \cdot HCl$. Methylphenidate HCl is a racemic mixture of d,l-threo-methyl α-phenyl-2-piperidineacetate hydrochloride. Several commercial products, including, e.g., Ritalin®, Daytrana™, and Metadate™ contain methylphenidate HCl as the active drug. Dexmethylphenidate is the d-threo-enantiomer of racemic methylphenidate hydrochloride [Focalin® product literature]. There are several commercial products which contain dexmethylphenidate as the active drug.

The use of the central nervous system stimulants methylphenidate and dexmethylphenidate for the treatment of such conditions as attention deficit disorder (ADD) and attention deficit hyperactivity disorder (ADHD) in adults and children has been described [see, Focalin®, Concerta®, Daytrana™ and Metadate® product literature]. This drug may also be used to treat depression and cognitive impairment following Traumatic Brain Injury [See, product literature for methylphenidate hydrochloride tablet which is commercially available from Lake Erie Medical DBA Quality Care Products LLC, and product literature of the other drug products identified herein].

Solid dose methylphenidate or dexmethylphenidate products are commercially available having an extended release profile of 8 hours according to the product label. These products include, e.g., Ritalin® LA and Methylin® ER tablets have product labels indicating that they must be swallowed whole without crushing or chewing. Liquid methylphenidate dosage forms have also been described which are predominantly designed for children, including children as young as 3 years old who have difficulty swallowing solid dosage forms.

There remains a need for a quick-acting, stable, extended release methylphenidate product which can be conveniently delivered in a form suitable for patients who have difficulty swallowing solid tablets and capsules.

SUMMARY OF THE INVENTION

The present invention provides a methylphenidate extended release chewable tablet which provides a fast onset of MPH and a twelve-hour release profile. The chewable tablet can be divided into portions and these tablet portions retain the fast onset and 12 hour release profile of the intact tablet. In one embodiment, the tablet is scored to facilitate splitting when desired. Methods of treating patients in need thereof with these methylphenidate (MPH) extended release chewable tablets are further provided by the invention.

The MPH extended release chewable tablet comprises (i) two different immediate release methylphenidate components, each of which provides a different immediate release profile, and (ii) about 50% to about 90% w/w of a sustained release barrier coated methylphenidate—ion exchange resin complex—matrix, based on the total weight of the methylphenidate components.

The first immediate release methylphenidate components is an uncoated methylphenidate—ion exchange resin complex, optionally in combination with a matrix forming polymer which is characterized herein as the "slower" onset immediate release component. The second immediate release component is a faster onset immediate release methylphenidate component which is a methylphenidate, pharmaceutically acceptable salt thereof, or hydrate thereof as defined herein, which is not complexed with or bound to an ion exchange resin. The sustained release component has a barrier coating which is a pH-independent release, high tensile strength, water insoluble, water-permeable barrier coating.

In another embodiment, the invention provides a scored chewable tablet, wherein dividing the tablet does not significantly modify the in vitro profile of the tablet portions resulting from split or other division of the intact tablet.

In one embodiment, a methylphenidate extended release chewable tablet comprises methylphenidate components in a combination of (a) about 60% w/w-80% w/w of a sustained release, cured, barrier coated methylphenidate—ion exchange resin complex—matrix, wherein the barrier coating comprises polyvinylacetate and a plasticizer (b) about 10% w/w to about 20% w/w of a combination of an immediate release uncoated methylphenidate—ion exchange resin complex and (c) about 10% w/w to about 20% w/w of an immediate release uncomplexed methylphenidate. Throughout this specification, when weight percentages and/or ratios are provided for methylphenidate in each of the three active components, the weights are based on the amount of methylphenidate base in each component. As used herein the term "uncomplexed methylphenidate" is referred to as the faster onset immediate release component and specifically includes a free base methylphenidate, as well as a pharmacologically active and physiologically compatible salt form thereof, including acid addition salts, and hydrates thereof; specifically excluded from the term "uncomplexed methylphenidate" is a methylphenidate which bound to or complexed with an ion exchange resin.

In a further embodiment, the invention provides a method of treating patients with a disorder for which methylphenidate is regulatory approved by administering a methylphenidate extended release chewable tablet as described herein.

Still other aspects and advantages of the invention will be apparent from the following detailed description of the invention.

BRIEF DESCRIPTION OF THE DRAWINGS

FIG. 1 is a linear plot of mean methylphenidate plasma concentration versus time using non-transformed data. This study provides the pharmacokinetic (pK) profile of a single oral chewable tablet formulation of the invention dosed as described in Example 2 to provide an amount of methylphenidate equivalent to a 40 mg dose of methylphenidate HCl. A commercially available immediate release methylphenidate HCl tablet (Methylin® 10 mg chewable tablet, 2×20 mg delivered six hours apart (q6h)) was used as reference.

DETAILED DESCRIPTION OF THE INVENTION

In one aspect the invention provides a methylphenidate (MPH) extended release chewable tablet. The MPH contains a combination of two different immediate release MPH components and a sustained release MPH component. Suitably, following administration of a single dose of the oral MPH extended release chewable tablet, in some embodiments, a therapeutically effective amount of MPH is reached in less than about thirty minutes, and as soon as about twenty, ten, or fewer minutes, and the formulation provides an extended release profile to at least about 12 hours.

The MPH extended release chewable tablets of the present invention are typically prepared as single uniform solid dispersion compressed into a chewable tablet. Suitably, the chewable tablet of the invention is a uniform solid dispersion which provides extended release properties even when scored such that when divided the separated tablet portions retain the extended release profile described herein. In one embodiment, the chewable tablet has a hardness of about 5 kilopond (kp) to about 25 kp, about 8 to about 20 kp, or 10 to about 16 kp. One (1) kilopond is one kilogram of force (kgf). Newtowns (N) are the SI unit of force and the SI standard for tablet hardness testing. 1 kilopond (kp) is equal to 9.80665 Newtons (N). Presented in Newton rounded to the nearest five, the chewable tablet has a hardness of about 45 N to about 245 N, about 75 N to about 200 N, or about 95 N to about 160 N. Optionally, the hardness may be dose proportional, with lower doses having lower hardness levels. For example, a 20 mg chewable tablet may have a hardness in the range of about 10 to about 12 kp (about 98 N to about 118 N), a 30 mg tablet may have a hardness in the range of about 12 to about 14 kp (about 118 N to about 137 N), and a 40 mg tablet may have a hardness in the range of about 14 kp to about 16 kp (about 137 N to about 156 N). In one embodiment, the hardness is determined following compression and prior to application of any color or other non-functional tablet coating as defined herein. In one embodiment, the tablet portions meet the USP Friability requirement. In one embodiment, the friability of both the intact tablet and the tablet portions are less than about 1.

A chewable tablet of the invention is distinguished from a rapid dissolve tablet or an orally dissolving tablet (ODT) by not dissolving in the mouth in less than 1 minute, and more generally, not breaking apart or dissolving in the oral cavity in less than about 3 to about 5 minutes without being chewed.

As used herein "methylphenidate" includes the free base form of the active ingredient which is either (i) racemic mixture of two optical isomers d-threo-methylphenidate and l-threo-methylphenidate or (ii) the active isomer d-threo-methylphenidate (also known as dexmethylphenidate). For convenience, methylphenidate is abbreviated "MPH" herein. When reference is made herein to methylphenidate or MPH, it will be understood that either the racemic mixture (typically 50/50 d- to l-) or dexmethylphenidate is encompassed by this term. Where only the racemate or dexmethylphenidate is desired, reference will be specifically made to one or the other. Thus, for the formulations described herein, the methylphenidate may be independently selected from racemic methylphenidate (e.g., a 50/50 mixture of D-methylphenidate and L-methylphenidate), and dexmethylphenidate. Whether selected from the racemate or dexmethylphenidate, the active drug may be present in the form of a salt or a hydrate. One suitable salt is the HCl salt form. However, other salts may be selected, e.g., the acetate salt, the maleate salt or any other pharmaceutically acceptable acid addition salt. Methylphenidate may be purchased commercially, e.g., as the hydrochloride salt thereof. Alternatively, the MPH may be prepared using methods known to those of skill in the art. Processes for the synthesis of methylphenidate and its analogs have been described. See, e.g., WO 2010/080787; U.S. Pat. Nos. 2,507,631 and 2,957,880, as have processes for synthesis of threo-methylphenidate and its d-enantiomer have been reported and which are incorporated herein by reference. See, e.g., US Patent Application Publication No. 2006/0135777, which is incorporated herein by reference.

As used herein, the term "free methylphenidate" refers to the weight of the methylphenidate base, i.e., exclusive of any salt or complex form.

In one embodiment, a MPH extended release chewable tablet the invention contains a methylphenidate in three different forms, (a) a sustained release barrier coated MPH—ion exchange resin complex, optionally in a matrix, (b) an slower onset immediate release uncoated MPH—ion exchange resin complex, optionally in a matrix, and (c) a faster onset immediate release uncomplexed MPH. While the source of the MPH in the working examples herein was the same, it will be understood that the MPH can be independently selected for each of component (a), (b) and (c). For example, the complexes of each (a) and (b) may be produced using the same MPH (e.g., racemic MPH) and (c) may be a different MPH (e.g., dexMPH). Alternatively, the complexes of each of (a) and (b) may be produced using different MPH and the MPH of (c) may be independently selected.

As used herein, the term "extended release" ("ER") refers to compositions which are characterized by having at least one of the active components (i.e., MPH or dexMPH) having a release over a period of at least about 12 hours. As with formulations described herein, "extended release" may be achieved by a single formulation containing two "immediate release" components and a "sustained release" (i.e., release for about 12 hours). The release profile may be assessed via in vitro dissolution using techniques known to those of skill in the art [e.g., USP basket method, Paddle Method, channel flow method, or other methods known in the literature]. The release profile can be assessed in vivo (e.g., for bioavailability determinations), using plasma concentrations to assess maximum plasma concentration ($C_{max}$) and area under the curve (AUC). Such assays are well known to those of skill in the art. [see, e.g., W. Wargin, et al., Pharmacokinetics of methylphenidate in man, rat and monkey. *J Pharmacol Exp Ther* August 1983 226:382-386].

The term "immediate release" ("IR") is the release of an active ingredient (e.g., MPH) from a pharmaceutical formulation where the rate of release of the active pharmaceutical ingredient from the pharmaceutical formulation is not retarded by means of a controlled release matrix or other such means and where the components of the pharmaceutical formulation are designed such that, upon ingestion, maximum exposure of said active pharmaceutical ingredient to body tissues occurs in the minimum period of time. As described herein, an "immediate release" MPH component preferably releases in less than 1 hour. The present invention provides for an extended release chewable tablet having two different immediate release MPH components, each of which provides a different release profile.

Suitably, one of the immediate release components provide a faster onset, i.e., release and therapeutic effect in less than 30 minutes, preferably, less than 20 minutes and in as few as ten minutes, or sooner. This immediate release component is an uncomplexed MPH which is defined in the specification. A second, different, immediate release component provides a different immediate release pharmacokinetic profile, which releases in less than about an hour, as soon as about 45 minutes, or as soon as about 30 minutes. Typically, this immediate release component does not release as quickly as the faster onset component. Suitably this slower onset immediate release component is an uncoated MPH—ion exchange resin complex, which is optionally in a matrix with a matrix forming polymer. When present in the immediate release component, the matrix forming polymer is selected so that the resulting uncoated MPH—ion exchange resin complex (optionally in a matrix) retains an immediate release profile. For convenience, the optional matrix is not referenced in every phrase where the uncoated complex is discussed. However, it will be understood that this uncoated complex may contain such a component. The release profiles of the two different immediate release components may overlap.

In one embodiment, the faster onset immediate release component (uncomplexed MPH) releases almost 100% of the MPH within about the first twenty to thirty minutes following administration. In another embodiment, the slower onset immediate release uncoated MPH—ion exchange resin complex releases at least about 50% of the MPH within about the first hour following administration, and at least about 80% of the MPH within about 90 minutes following administration.

In one example, the sustained release barrier coated MPH—ion exchange resin complex, optionally in a matrix is present in an amount of about 50% w/w to about 90% w/w, about 60% w/w to about 80% w/w, or about 68 w/w to about 72% w/w of the MPH components in the chewable tablet. The two immediate release components combine to provide about 10% w/w to about 50% w/w, about 20% w/w to about 40% w/w, or about 25% w/w to about 30% w/w of the MPH components in the chewable tablet. The uncoated MPH—ion exchange resin complex component is designed to be immediate release as defined herein, and as such, does not contain a coating which functions to delay release (e.g., no functional amount of an extended release barrier coating or enteric coat). Suitably, immediate release MPH—ion exchange resin complex is present in an amount of about 5% w/w to about 30% w/w, or about 10% w/w to about 20% w/w, of the MPH components in the chewable tablet. The extended release component and the immediate release MPH—ion exchange resin complex are further in combination with an uncomplexed MPH drug. The other IR component, which is uncomplexed MPH drug, is present in an amount of about 5% w/w to about 30% w/w, or about 10% w/w to about 20% w/w, of the MPH components in the chewable tablet. In one embodiment, the weight percentages of MPH contributed by each of the two immediate release components are the same. However, in other embodiments, it may be desirable to provide MPH in the immediate release components in different weight percentages.

When expressed as a ratio, the ratio of the two immediate release components comprise MPH in a ratio of uncoated MPH-resin complex (optionally in a matrix) to that in uncomplexed methylphenidate in the chewable tablet is generally in the range of about 6:1 (uncoated MPH complex: uncomplexed MPH) to about 1:6 (uncoated MPH complex: uncomplexed MPH), or about 2:1 to about 1:2. In one embodiment, the ratio of extended release coated MPH—resin complex to uncoated MPH complex is in the range of about 18:1 (coated MPH: uncoated MPH complex) to about 5:3 (coated MPH complex: uncoated MPH complex), or about 8:1 to about 3:1.

In one embodiment, the ratio of MPH in coated MPH—resin complex: uncoated MPH—resin complex: uncomplexed MPH is 80:10:10 to about 70:15:15. However, other suitable ratios, including those in which the MPH in the two immediate release components differ from each other, may be selected within the ranges provided herein.

The term "initial administration" is defined for purposes of the present invention as the first single dose of a formulation containing an active ingredient administered to a patient or subject or the first dose administered to a patient or subject after a suitable washout period.

As is often the case with psychoactive drugs, a therapeutic result for MPH is not solely related to plasma levels of the drug. Thus, "a therapeutically effective amount" of MPH includes the minimum amount of the drug required to provide a clinically observable psychological and/or behavioral response. A therapeutically effective amount of MPH can alternatively be defined as being at least the minimum amount of MPH which reduces or eliminates the symptoms associated with a condition for which MPH has been approved for use. Appropriate doses are discussed in more detail later in this specification.

Additionally, because the chewable MPH tablet described herein retains its extended release properties even when scored. Further, even following being divided into other suitable portions, it is convenient for physicians to reduce the dose for patients to introduce the drug in a smaller dose or incremental doses of medication for patients whose needs dictate such. This ability to divide the dose into portions allows physicians to take into consideration individual patient needs, including factors like age, body weight and individual response to the medication without the need for taking multiple doses over a twelve hour period of another product which offers only immediate release.

A "methylphenidate—ion exchange resin complex" refers to the product resulting from loading a methylphenidate salt onto a cation exchange resin. Methods for preparing such complexes have been described, e.g., in WO 2007/109104, incorporated herein by reference. This describes the complexation which occurs when the active and the ion exchange resin are mixed together in an aqueous medium to facilitate the "exchange" between the salt of the MPH and the "cation" of the ion exchange resin and the formation of the complex, which may be referred to as "methylphenidate polistirex".

WO 2007/109104 also describes polyvinylacetate-based barrier coatings which are particularly well suited for use in the formulations described herein to provide a sustained release coat over the MPH—ion exchange resin complex—matrix. However, one skilled in the art can select other barrier coatings to provide the sustained release characteristics to MPH—ion exchange resin complex—matrix.

As used herein, a "precoated" MPH—ion exchange resin complex or a "precoated" MPH—ion exchange resin complex—matrix refers to a particle which is to be subsequently coated with a barrier coating as defined herein. In some embodiments, where the MPH—ion exchange resin or MPH—ion exchange resin complex—matrix is to be used as one of the immediate release components and no barrier coating is to be applied, it is referred to as "uncoated".

As used herein, a barrier coat is a water-permeable, water-insoluble, pH-independent polymer or co-polymer which in the present invention confers sustained release to the coated MPH—ion exchange resin complex—matrix. In one embodiment, the barrier coat is pH-independent, non-ionic and is applied, e.g., as an aqueous suspension, over the precoated MPH—ion exchange resin complex—matrix and forms a separate layer thereon. In another embodiment, the barrier coat is pH-independent, non-ionic and is applied as a solvent-based coating, over the precoated MPH—ion exchange resin complex—matrix and forms a separate layer thereon. In still another embodiment, the barrier coat is pH-independent, ionic and is applied over the precoated MPH—ion exchange resin complex—matrix to form a separate layer thereon. Preferably, the barrier coat is directly over the precoated MPH—ion exchange resin complex—matrix and the barrier coat layer, i.e., there are no intervening layers between the barrier coat and the precoated MPH—ion exchange resin complex—matrix. Depending upon the polymeric material selected, the barrier coat polymer or co-polymer may be cured to maximize their properties depending on the barrier coating selected. These polymers and their curing requirements are discussed in more detail elsewhere in this specification.

A "methylphenidate—ion exchange resin complex—matrix" refers a MPH—ion exchange resin complex which is further combined, e.g., prior to or during granulation, with a polymeric material which forms a matrix with the MPH—ion exchange resin complex.

In one embodiment, a "methylphenidate polistirex" refers to the complex formed by loading a methylphenidate onto or reacting a methylphenidate with an ion exchange resin. This term and the term "MPH—ion exchange resin complex" may be used interchangeably throughout this document.

The term "matrix forming polymer" or "matrix forming polymeric material" refers to both water-insoluble polymers/co-polymers and water-soluble polymers/co-polymers which form a matrix with the MPH—ion exchange resin complex upon being admixed or granulated therewith. Suitably, the matrix forming polymer is non-reactive with the MPH and the ion exchange resin. The matrix forming polymer may be a water-insoluble polymers/co-polymers and polymer systems which have been described as release retardants [see, e.g., polymers discussed in U.S. Pat. No. 8,062,677, incorporated herein by reference], and those hydrophilic polymer systems which have been described in the literature as impregnating or solvating agents [see, e.g., polymers discussed in U.S. Pat. Nos. 8,062,677 and 4,221,778, incorporated herein by reference]. In one embodiment, a MPH—ion exchange resin complex—matrix may include more than one matrix-forming polymer system. For example, an MPH—ion exchange resin complex—matrix may contain both a hydrophilic polymer and a hydrophobic polymer. An immediate release "uncoated methylphenidate—ion exchange resin complex" may optionally be in a matrix. In this instance, the matrix forming polymer does not alter the ability of component to provide an immediate release profile. For example, a polyvinylpyrrolidone may be selected. However, the matrix forming polymer may alter the release rate of this complex while still maintaining an immediate release profile as defined herein.

The following terms are used in the specification and are to be interpreted in accordance with the definitions herein.

"$C_{max}$" is the maximum observed plasma concentration, calculated as the geometric mean of the individual maximum blood plasma concentrations.

The term "mean maximum plasma concentration" (mean $C_{max}$) is defined for the purposes of the present invention as the maximum mean plasma drug concentration.

"Mean plasma concentration" is the geometric mean blood plasma concentration.

The term "$T_{max}$" is the time at which the peak (maximum) observed blood plasma drug concentration for each individual participating in the bioavailability study.

The term "$AUC_{0-\infty}$" or "$AUC_{inf}$" is the mean area under the plasma concentration-time curve extrapolated to infinity It is calculated as the arithmetic mean of the area under the plasma concentration-time curve from time 0 extrapolated to infinity, calculated for each individual participating in the bioavailability study.

AUCpR is the area under the curve to the population median $T_{max}$ of the reference formulation. $AUC_{0-t}$ is the area under the plasma/serum/blood concentration-time curve from time zero to time t, where t is the last time point with measurable concentration for individual formulation.

T/R ratio refers to the test formulation (MPH ER chewable tablet (40 mg) to reference (R) formulation (Methylin® IR 10 mg chewable tablet).

Intra-subject CV % refers to the geometric (CV) coefficient of variation between subjects.

The term "half-life" is the apparent terminal elimination half-life ($T_{1/2}$).

The words "comprise", "comprises", and "comprising" are to be interpreted inclusively rather than exclusively. The works "consist", "consisting", and its variants, are to be interpreted exclusively, rather than inclusively.

As used herein the term "about" means a variability of 10% from the reference given, unless otherwise specified.

Methylphenidate/Dexmethylphenidate—Ion Exchange Resin Complex

A selected MPH can be complexed with, or loaded onto, a cation exchange resin, using methods which are known in the art. See, e.g., WO 2007/109104, and the documents cited therein. Cationic exchange resins are readily selected for use as described herein.

A number of the processing steps described herein, including, e.g., loading, pre-washing, complexing and granulation may be carried out in a multi-purpose apparatus, e.g., such as the PEF 450 processor [Pall SeitzSchenk] or another similar and larger scale multi-purpose apparatus which is available commercially [e.g., by Rosenmund, U.S. Pat. No. 5,609,835]. The vessel is capable of or adapted for pivoting and has a single chamber with the capacity for handling a reaction/crystallization, filtration, resuspension, and drying. Such a vessel is typically provided with a water jacket connected with a thermostatically controlled heating and cooling system. Alternatively, the processing steps described herein may be carried out in another type of apparatus, or other multiple different apparatus, such as are known in the art.

Ion Exchange Resins

Cationic exchange resins vary in strength, i.e., in their ability to exchange cations. In one embodiment, a relatively strong cationic resin, e.g., Amberlite® IRP69, manufactured by Rohm and Haas (a sulfonated copolymer of styrene and divinylbenzene) is selected. Alternatively, one may select a relatively weak cationic exchange resin, e.g., Amberlite® IRP88 [Rohm and Haas, a crosslinked polymer of methacrylic acid and divinylbenzene)], a weakly acidic (potassium ion) cation exchange resin with 4% cross-linked methacrylate (100 to 500 mesh, equivalent to about 150 microns to about 27 microns, ASTM standard) or Amberlite® 64 (a methacrylic acid and divinylbenzene polymer (hydrogen ion) polyacrilex resin, Rohm and Haas, with a particle size ranging from 100 to 400 mesh (equiv to 35 microns to 150 microns, ASTM standard size), capacity ~10 meq/g by dry weight). Further, either regularly or irregularly shaped particles may be used as cation exchange resins according to the present invention. Regularly shaped particles are those particles that substantially conform to geometric shapes such as spherical, elliptical, cylindrical and the like, which are exemplified by Dowex® 50WX8 (The Dow Chemical Company). Irregularly shaped particles are all particles not considered to be regularly shaped, such as particles with amorphous shapes and particles with increased surface areas due to surface channels or distortions. Irregularly shaped ion-exchange resins of this type are exemplified by Amberlite® IRP-69 (manufactured by Rohm & Haas), the use of which is illustrated in the examples below. This cation exchange resin is a sulfonated polymer composed of polystyrene cross-linked with about 8% of divinylbenzene, with an ion-exchange capacity of about 4.5 to 5.5 meq/g of dry resin (H+-form). Another cation exchange resin having similar properties is Dowex® 50WX8 (H+ form, linear formula, $C_{10}H_{12} \cdot C_{10}H_{10} \cdot C_8H_8)_x$, 200-400 mesh particle size, which is equivalent to about 75 microns to about 35 microns, ASTM standard). Amberlite® IRP-69 consists of irregularly shaped particles with a size range of about 100 to about 500 mesh (about 150 microns to about 27 microns, ASTM standard). Dowex® 50WX8 is more regularly shaped. Resins are generally purchased with a size ranging from about 25 microns to about 400 microns. However, other sizes may be selected, or larger sized particles may be milled to provide smaller particle sizes.

The selected ion-exchange resins may be further treated by the manufacturer or the purchaser to maximize the safety for pharmaceutical use or for improved performance of the compositions. Impurities present in the resins may be removed or neutralized by the use of common chelating agents, anti-oxidants, preservatives such as disodium edetate, sodium bisulfite, sodium metabisulfite, and so on by incorporating them at any stage of preparation either before complexation or during complexation or thereafter. These impurities along with their chelating agent to which they become bound may be removed before further use of the ion exchange resin.

The amount of methylphenidate that can be complexed with a resin will typically range from about 5% to about 50% by weight of the MPH—ion exchange resin complex particles. A skilled artisan with limited experimentation can determine the optimum loading for any MPH—ion exchange resin complex. In one embodiment, loading of about 10% to about 40% by weight, more desirably, about 15% to about 30% by weight, or about 25% of the MPH—ion exchange resin complex particles can be employed. In one embodiment, a composition of the invention contains MPH complexed to a sodium polystyrene sulfonate resin in at a ratio of 20 MPH (based on the weight of the MPH salt) to 300 resin to 80 MPH (based on the weight of the MPH salt) to 100 resin. In another embodiment, the MPH (based on the weight of the MPH salt) to resin ratio is 4:10 to 1:10, or about 4:10 to about 2:10. In a further embodiment, the dexMPH permits the use of about half the amount of active required when racemic MPH is the active drug.

In one embodiment, following complexation, a MPH—ion exchange resin complex may be, in no particular order, milled to achieve a desired size range and dried (e.g., to a moisture content below about 10%, e.g., about 3% to about 7%), and then stored for future use. In one embodiment, the complex is milled or passed through a sieve to provide a particle size ranging from about 40 microns to about 410 microns to enhance mouth feel (i.e., texture), or about 50 microns to about 250 microns. These particles may be either regularly or irregularly shaped. In some embodiments, the average particle size of the uncoated MPH—ion exchange resin complex or the average particle size of the coated MPH ion exchange resin complex is milled to a size of about 100 to about 200 microns. These particle sizes maybe determined using sieve analysis through a sieve shaker having USP standard wire mesh sieves conforming to ASTM specifications.

In one embodiment, a matrix forming polymer is combined with the MPH—ion exchange resin complex following only partial complexation, or by reducing the moisture content of the wet MPH—ion exchange resin complex to a range of between about 15 to about 25%, or another suitable amount. Treatment of the MPH—ion exchange resin complex with the matrix forming polymer is as follows.
MPH—Ion Exchange Resin Complex—Matrix Optionally, a matrix-forming polymer is used to assist in processing an uncoated or precoated MPH—ion exchange resin complex. For example, a matrix-forming polymer may be used to facilitate granulation of the immediate release MPH component (e.g., an uncoated MPH—ion exchange resin complex). Alternatively, the matrix-forming polymer may be used for another purpose.

In one embodiment, a polyvinylpyrrolidone polymer [e.g., such as may be purchased commercially as Kollidon® 30] is combined with the methylphenidate—ion exchange resin complex in order to facilitate granulation prior to coating. Other hydrophilic polymeric granulating agents may include water-soluble polymeric materials which have been described in the art as impregnating agents or solvating agents and which function in the present application as granulating agents. In one embodiment, the granulating agent is a polyethylene glycol. Examples of desirable impregnating/solvating agents include those described in U.S. patent application Ser. No. 11/724,966, filed Mar. 15, 2007, Published as US 2007-0215511A, Sep. 20, 2007, and Meadows, US 2003-0099711, which are incorporated herein by reference, or in U.S. Pat. No. 4,221,778 and published US Patent Application Publication No. US 2003/0099711 A1, the disclosures of which are incorporated herein by reference. Specific examples of other impregnating agents include propylene glycol, polyethylene glycol, polyvinyl alcohol, hydroxypropyl methylcellulose, hydroxypropyl cellulose, and sorbitol.

Optionally, the MPH release rate from the compositions of the present invention may be admixed or granulated with a water-soluble or water-insoluble polymer or a combination of a water-insoluble polymers prior to the application of the water-permeable diffusion barrier coating described herein. Upon admixture, these polymers do not form a separate layer on the MPH—ion exchange resin complex, but form a matrix therewith. Examples of suitable matrix forming polymers include, for example, a polyvinyl acetate polymer or a mixture of polymers containing same (e.g., KOLLICOAT® SR 30D), cellulose acetates, ethylcellulose polymers (e.g., AQUACOAT™ ECD-30 or SURELEASE™), acrylic based polymers or copolymers (e.g., represented by the EUDRAGIT family of acrylic resins), cellulose phthalate, or any combination of such water-insoluble polymers or polymer systems. These matrix-forming polymers when used may further prolong or alter the release of the MPH from the ion exchange resin complex/matrix and maximize attaining the desired release profile. One suitable polymer is a polyvinyl acetate polymer as described herein or an acrylic polymer from the EUDRAGIT family. Examples of suitable acrylic polymers from the EUDRAGIT family may include, e.g., a copolymer comprising ethyl acrylate and methyl methacrylate (e.g., EUDRAGIT® NE-30D), or EUDRAGIT® RS30D, RL30D, which are largely pH-independent polymers. EUDRAGIT® RS30D is a 30% aqueous dispersion of poly (ethyl acrylate-co-methyl methacrylate-co-trimethylammonioethyl methacrylate chloride) in a ratio of 1:2:0.1; other aqueous dispersions of this copolymer may be selected. Eudragit® RL30 D is a 30% aqueous dispersion of poly (ethyl acrylate-co-methyl methacrylate-co-trimethylammonioethyl methacrylate chloride) 1:2:0.2; other aqueous dispersions of this copolymer may be selected for use in the invention. Although less desirable, certain pH-dependent (enteric) polymers including, e.g., members of the EUDRAGIT polymer family, e.g., the L, S, and E, polymers and others which are commercially available may be selected.

The quantity of polymer that is added to an uncoated or precoated MPH—ion exchange resin complex as a matrix forming polymer typically ranges from about 1% to about 30%, or about 3 to about 20%, or about 3 to about 10%, about 10% to about 15%, about 15 to 25%, or about 1 to about 5% or more by weight of the uncoated or precoated MPH—ion exchange resin particulates prior to their being coated. However, higher or lower amounts may be selected. In one embodiment, where it is desired for the matrix forming polymer to have little or no effect on release rate, a hydrophilic polymer may be selected and used in a higher amount, whereas a hydrophobic release retardant if selected for use will be used at a lower amount. Following admixing, the uncoated or precoated MPH—ion exchange resin complex particles with the matrix forming polymer, the mixture is dried and the MPH—ion exchange resin complex—matrix granules are milled appropriately to the desired particulate size.

For the precoated MPH—ion exchange resin complex—matrix which will be coated and the uncoated MPH—ion exchange resin complex, the particles are milled though a size below about 410 microns, or generally in the range of about 50 microns to about 410 microns, or about 100 microns to about 410 microns. This can be achieved, e.g., using a CO-MIL device fitted with a 40 mesh screen. In one embodiment, the particles have an average size of about 100 to about 250 microns, or about 100 to about 200 microns. In some cases, the milling may be carried out before the complete drying of the complex or complex matrix and then again further drying followed by milling to obtain the desired complex characteristics. These particle sizes maybe determined using sieve analysis through a sieve shaker having USP standard wire mesh sieves conforming to ASTM specifications.

Barrier Coat for Sustained Release

The sustained release component of a MPH chewable tablet of the invention contains a methylphenidate—ion exchange resin complex—matrix with a barrier coating which modifies the release profile of the methylphenidate—ion exchange resin complex—matrix such that the methylphenidate has about a 12 hour sustained release profile. Suitably, the barrier coating has a pH-independent release (i.e., it is not an enteric coating which has pH-dependent release) and is a water-insoluble, water-permeable coating material. In a preferred embodiment, neither the chewable tablet nor any of its components has an enteric coating.

Suitably the properties of the barrier coating provide sustained release properties to the barrier coated MPH—ion exchange resin complex, which is MPH—ion exchange resin is optionally in matrix. When the matrix is present, the barrier coating is applied over the MPH—ion exchange resin complex—matrix. The barrier coating provides the sustained release component with resistance to grinding forces which enables the portions of a chewable tablet of the invention to provide a sustained release MPH profile even when cut into pieces.

The barrier coating has a characteristic high flexibility or elongation (elasticity) at break measured by the texture analyzer TA-XT2 HiR (Stable Microsystems) and by the method reported by the manufacturer in its literature [i.e., Jan-Peter Mittwollen, Evaluation of the Mechanical Behavior of Different Sustained Release Polymers, Business Briefing: Pharmagenerics, 2003, pp. 1-3, BASF], with a tensile strength in a range of at least about 150% to about 400%. When the polyvinylacetate based barrier coating described herein is selected, this is achieved while not substantially increasing the tackiness of the polymer film greater than about 2 (wherein the film is measured by the Hössel method referenced above independent of any composition on which it has been deposited).

In one embodiment, the barrier coating layer is about 10% to about 70%, by weight, or about 15% to about 65%, by weight, of the precoated methylphenidate—ion exchange resin complex—optional matrix in order to provide the sustained release component. In another embodiment, the barrier coating layer is about 20% to about 50%, about 25% to about 40% by weight, about 25% to about 35% by weight, or about 30%, by weight of the precoated methylphenidate—ion exchange resin complex—optional matrix (i.e., prior to coating). Still other suitable ranges can be determined by one of skill in the art, having been provided with the information herein.

The barrier coating is applied over the uncoated or precoated MPH—ion exchange complex—optional matrix (e.g., as an aqueous dispersion or a solution), dried, and milled or passed through a screen such that the barrier coated MPH—ion exchange complex—optional matrix particles are in the same size range as described in the preceding paragraph, i.e., in the range of about 50 to about 410 microns.

In one embodiment, the barrier coating is applied as an aqueous dispersion which is dried in order to provide the desired sustained release profile. In the case of an aqueous-based polyvinylacetate coating, the coating is cured in order to provide the desired release profile.

In one embodiment, the barrier coating is applied as an aqueous dispersion of a water insoluble polymer comprising a polyvinyl acetate polymer, or a blend of polymers comprising a polyvinyl acetate polymer. In one embodiment, the barrier coating further contains a plasticizer, which can facilitate uniform coating of the MPH—ion exchange resin complex and enhances the tensile strength of the barrier coating layer.

One coating composition useful in the present invention is applied in the form of an aqueous dispersion containing polyvinylacetate (PVA) polymer based aqueous coating dispersion and a plasticizer. The PVA is insoluble in water at room temperature. The PVA may be used in either substantially pure form or as a blend. Where the barrier coating comprises a PVA polymer, the PVA polymer is present in an amount of about 70% to about 90% w/w of the final barrier coating layer, at least about 75%, at least about 80%, about 85% w/w of the final barrier coating layer. Generally, a plasticizer is used in the percent range, or a mixture of plasticizers combine to total about 2 to about 50% by weight of the coating layer, more preferably about 2.5% to about 20% by weight of the coating layer on the coated MPH—ion exchange resin complex. Preferably a plasticizer is in a range of about 2.5 to about 15% by weight of the coating layer based on the coated complex provides the most desirable properties. Suitable plasticizers may be water soluble and water insoluble. Examples of suitable plasticizers include, e.g., dibutyl sebacate, propylene glycol, polyethylene glycol, polyvinyl alcohol, triethyl citrate, acetyl triethyl citrate, acetyl tributyl citrate, tributyl citrate, triacetin, and Soluphor® P (2-pyrrolidone), and mixtures thereof. Other plasticizers are described in US Patent Application Publication US 2003/0099711 A1, May 29, 2003, page 4 (0041) the disclosure of which is incorporated herein by reference.

A commercial polyvinylacetate blend contains primarily a polyvinylacetate polymer, a stabilizer, and minor amounts of a surfactant such as sodium lauryl sulfate. Where the barrier coating comprises PVP as the stabilizer component, the final barrier coating layer generally contains about 5 to about 10% w/w of polyvinyl pyrrolidone. In one desired embodiment, the aqueous based barrier coating solution is KOLLICOAT® SR 30 D (BASF Corporation) and whose composition is about 27% PVA polymer, about 2.7% polyvinylpyrrolidone (PVP), about 0.3% sodium lauryl sulfate (solids content 30% w/w), mixed with a plasticizer. See, also, U.S. Pat. Nos. 6,066,334 and 6,026,277, which is incorporated by reference herein. The PVP and surfactant help stabilize the aqueous dispersion of the PVA. Generally, such stabilizing components are present in an amount totaling less than about 10% w/w, and preferably less than about 5% w/w. Optionally, a selected surfactant is present in an amount of about 1% or less. In one embodiment, the surfactant is a non-ionic surfactant. Optionally, an ionic surfactant may be selected.

In a particularly desirable embodiment, the desired modified release is obtained when the coating layer formed by application of the aqueous dispersion containing the KOLLICOAT® SR-30D—plasticizer is dried and cured. Preferably, the coating is cured for about 1 to about 24 hours. In alternate embodiments, the coating is cured for about 4 to about 16 hours, and preferably about 5 hours at high temperature, e.g., about 50° C. to about 65° C., and preferably about 60° C. Thus, in one embodiment, the coated MPH—cation exchange resin complex—matrix has a cured water-permeable, high tensile strength, water insoluble, barrier coating comprising a non-ionic polymer and a plasticizer and having an elongation factor in the range of about 150% to 400% over the MPH—cation exchange resin complex—matrix. In one embodiment, the barrier coating comprises a polyvinylacetate polymer, a stabilizer, a surfactant and a plasticizer. In one embodiment, a barrier coating comprises about 2.5 to about 15% of plasticizer, about 70 to about 90% polyvinylacetate, about 5 to about 10% polyvinylpyrrolidone, and about 0.1 to about 1% surfactant. See, e.g., Mehta et al, US Published Patent Application No. US 2007-0215511A, published Sep. 20, 2007, and its counterpart application, WO 2007/109104, which are incorporated herein by reference.

It may be possible to select other aqueous or non-aqueous solvent based systems which do not require curing. For example, an aqueous based acrylic polymer (a Eudragit® RL30D and Eudragit® RS30D blend is described herein), but requires the addition of anti-tacking agent such as, e.g., talc or glycerol monostearate (GMS), in order to facilitate processing and even coating.

In one embodiment, the coating may be a EUDRAGIT® brand acrylate based coating materials [including, e.g., a poly (ethyl acrylate-co-methyl methacrylate-co-trimethylammonioethyl methacrylate chloride) polymer system]. For example, Eudragit® RS 30D [a pH-independent, 30% aqueous dispersion of poly (ethyl acrylate-co-methyl methacrylate-co-trimethylammonioethyl methacrylate chloride) 1:2:0.1)], or Eudragit® RL 30D [a 30% aqueous dispersion, pH independent polymer, poly (ethyl acrylate-co-methyl methacrylate-co-trimethylammonioethyl methacrylate chloride) 1:2:0.2)] may be selected as the barrier coating. In one embodiment, a blend of Eudragit® RS 30D and Eudragit® RL 30D may be prepared to optimize the hydrophilicity/hydrophobicity of the film in order to achieve desirable release profiles. Suitably, a plasticizer may be included in the coating composition. In one embodiment, the barrier coating comprises about 2.5 to about 15% of plasticizer. Individual or a combination of hydrophilic or lipophilic plasticizers with a dispersion or suspension containing the barrier coating polymer. Such plasticizers include, e.g., propylene glycol, polyethylene glycol, triacetin, triethyl citrate, dibutyl sebacate, vegetable oil, lipids, etc. Optionally, a suitable anti-tacking agent may be mixed with one of the Eudragit™ products to improve flow during coating and to address issues of tackiness of the product during processing. Suitable anti-tacking agents include, e.g., talc, glycerol monostearate (GMS), and mixtures thereof. Suitably, these agents are present in an amount of about 0.2%-4.5% w/w based on the dry weight of the coating polymer applied to form the coating layer of the sustained release component. Typically, the coating layer resulting from application of the blend described in this paragraph is not subject to any curing.

Optionally, another barrier coating may be selected. In another embodiment, non-aqueous solvent-based ethylcellulose such as in commercially available as the line of ETHOCEL™ products by Dow] may be modified in order to achieve the barrier coating characteristics defined herein, e.g., by addition of a sufficient amount of plasticizer to improve flexibility and/or by curing to a sufficient temperature to achieve the desired release rate. Dow's web site describes three of these products, Std 7 (viscosity of 6-8 mPa-s (CP); Std 10 (9-11 mPa-s (CP); Std 20 (18-22 mPa-S), each of which has a 48.0-49.5% ethoxyl content) as being useful for tablet coating. Further, optionally combining one of these polymers in combination with a water-soluble active and/or water-soluble excipient such as a METHOCEL™ cellulose ether and/or CARBOWAX™ polyethylene glycols is further described. Alternatively, it may be possible to modify an aqueous based ethylcellulose barrier coating in order to achieve the extended release barrier coating characteristics required herein, e.g., by addition of a sufficient amount of plasticizer to improve flexibility and/or by curing to a sufficient temperature to achieve the desired release rate. See, e.g., the barrier coatings described in Kolter et al, U.S. Pat. Nos. 6,066,334 and 6,046,277 and See, also, e.g., Wen, U.S. Pat. Nos. 6,046,277 and 6,001,392; Meadows, US Published Patent Application No. 2003/0099711 and related application WO 03/020242; Sovereign Pharmaceuticals, WO 2006/022996 and related applications US Published Patent Application Nos. US2005/0232986; US2005/0232987; US2005/0232993; US2005/0266032; Bess, et al, U.S. Pat. No. 7,067,116; Goede et al, U.S. Pat. No. 6,667,058, Wen et al, U.S. Pat. No. 6,001,392, among others.

A coating as described herein may be applied using techniques described by the polymer manufacturer and/or techniques which are known to those of skill in the art. Suitable methods and apparatus have been described in the patent and non-patent literature and include, e.g., spraying in a fluid bed processor. The coating solution can be sprayed in a fluid bed processor (e.g., VECTOR™ FLM-1 fluid bed processor) using Wurster process. The Coated MPH Resin Complex is then dried and/or cured. The dried, optionally cured, coated methylphenidate—ion exchange resin complex—optional matrix may be passed through a suitable screen in order to ensure that the particle size is in the desired range, e.g., capable of passing through a standard 40 mesh screen. In one embodiment, the dried, optionally cured, coated MPH ion exchange resin complex (optional matrix) granules have a mean particle size in the range of about 100 microns to about 450 microns, or about 150 to about 300 microns.

Finished Dose Formulations

The invention provides MPH extended release chewable tablets. In order to prepare the finished dose form, the three MPH components are blended with excipients and compressed into a chewable tablet. In one embodiment, the excipients do not provide the extended release properties of the chewable tablet. The sustained release profile is provided by the sustained release barrier coated MPH—ion exchange resin complex—matrix component.

The three MPH components may be pre-blended in the desired ratio to one another prior to being admixed with the excipients, described below. Alternatively, each of the three MPH components are added separately and blended with the excipients.

As described above in this specification, the sustained release barrier coated MPH—ion exchange resin complex, optionally in a matrix is present in an amount of about 50% w/w to about 90% w/w, about 60% w/w to about 80% w/w, or about 65 w/w to about 75% w/w of the MPH components in the chewable tablet. Thus, the two immediate release components combine to provide about 10% w/w to about 50% w/w, about 20% w/w to about 40% w/w, or about 25% w/w to about 35% w/w of the MPH in the chewable tablet. The uncoated MPH—ion exchange resin complex component is designed to be immediate release as defined herein, and as such, does not contain a coating which functions to slow down release (e.g., no functional amount of an extended release barrier coating or enteric coat). Suitably, the slower onset immediate release MPH—ion exchange resin complex supplies about 5% w/w to about 25% w/w, or about 10% w/w to about 20% w/w, of the MPH in the chewable tablet. The extended release component and the immediate release uncoated MPH—ion exchange resin complex are further in combination with an uncomplexed MPH drug. The faster onset immediate release uncomplexed MPH drug is present in an amount of about 5% w/w to about 30% w/w, or about 10% w/w to about 20% w/w, of the MPH in the chewable tablet. When the two immediate release components are expressed as a ratio, the ratio of MPH in the uncoated MPH—resin complex (optional matrix) to uncomplexed MPH in the chewable tablet is generally in the range of about 6:1 (uncoated MPH—ion exchange resin complex: uncomplexed MPH) to about 1:6 (uncoated MPH—ion exchange resin complex: uncomplexed MPH), or about 2:1 to about 1:2. In one embodiment, the ratio of MPH from the extended release coated MPH—ion exchange resin complex to MPH from the uncoated MPH immediate release component is in the range of about 18:1 (coated MPH: uncoated MPH—ion exchange resin complex (optional matrix)) to about 5:3 (coated: uncoated), or about 8:1 to about 3:1.

In one example of a chewable tablet of the invention, a methylphenidate extended release chewable tablet has a pharmacokinetic profile in which $AUG_{0-\infty}$ for methylphenidate has a geometric mean of about 110 ng-hr/mL to about 140 ng-hr/mL, a geometric mean $C_{max}$ of about 10 ng/mL to about 15 ng/mL, $T_{max}$ of about 4 hours to about 5.25 hours and $T_{1/2}$ of about 5 hours to about 7 hours following a single oral administration of an extended release chewable tablet at a dose equivalent to 40 mg racemic MPH HCl in adults.

In another example, the methylphenidate chewable tablet has a pharmacokinetic profile in which $AUC_{0-\infty}$ for methylphenidate has a geometric mean of about 113 ng-hr/mL under fasted conditions and about 138 ng-hr/mL under fed conditions, a geometric mean $C_{max}$ of about 12 ng/mL to about 13 ng/mL under fasted and fed conditions, an arithmetic mean $T_{max}$ of about 4 to about 4.5 hours under fasted and fed conditions and an arithmetic mean $T_{1/2}$ of about 5.2 hours under fasted and fed conditions, following a single oral administration of an extended release chewable tablet at a dose equivalent to 40 mg racemic MPH HCl in adults. For example, the extended release chewable tablet may have the pharmacokinetic profile of FIG. 1 following a single oral administration at a dose equivalent to 40 mg racemic MPH HCl in adults.

The MPH extended release chewable tablets may be prepared using one or more of a filler, one or more disintegrant, one or more binder, one or more a buffering agent, one or more lubricant, one or more glidant, or blends of these components. Suitably, the tablets also include taste and/or mouth feel enhancers including, e.g., one or more of a sweetener, a flavorant, a gum, or blends of these components. Optionally, the tablet may also contain a non-functional coating.

As used herein, a "non-functional coating" refers to a coating which contributes no detectable modified release functions. The non-functional coating may be a polymer may serve as a moisture barrier to preserve the integrity of the tablet during storage or to facilitate application of a color coating layer. Additionally or alternatively, the non-functional coating may provide a color coating layer or improve the "smoothness" or mouth feel of the tablet. In one embodiment, the non-functional coating may increase the hardness of the tablet somewhat without affecting the chewability thereof.

Throughout the specification, where weight percentages of excipients and the three active components are provided, the weight percentages are exclusive of any weight added by a non-functional coating. Weight percentages of these non-functional coatings, where present, are provided as weight added, in an amount of about 1% to about 20%, or about 2% to about 10%, or about 3% to about 5% weight added to the finished chewable tablet.

Typically, a chewable tablet will contain a filler or a mixture of fillers in the range of about 10% w/w to about 90% w/w, about 50% w/w to about 85% w/w, or about 50% w/w to about 70% w/w of the total tablet weight. Suitable fillers may include, e.g., Mannitol, Lactose, Maltose, Fructose, Sucrose, Xylitol, Maltitol, Microcrystalline Cellulose, Dicalcium phosphate, Guargum, Xanthan gum, Tragacanth gum, Pre-gelatinized Starch, Compressible sugar, Calcium carbonate, Magnesium carbonate, Calcium sulfate, Dextrates, Maltodextrin. In one embodiment, a chewable tablet of the invention contains a blend of mannitol, xanthan gum, microcrystalline cellulose, and guargum in an amount of about 60% w/w to about 75% w/w. In one embodiment, a gum or a combination of gums is provided in an amount of about 0.25% w/w to about 5% w/w, or about 0.25% to about 1% w/w. In another embodiment, microcrystalline cellulose is provided in an amount of about 5% w/w to about 25% w/w, or about 10% w/w to about 15% w/w based on the total tablet weight prior to any non-functional coating. A product containing a combination of microcrystalline cellulose and guar gum is commercially available as Avicel®, which contains a ratio of 80 parts by weight microcrystalline cellulose to 20 parts by weight guar gum. This blend of microcrystalline cellulose (MCC) and guar gum may be present in an amount of about 5% w/w to about 25% w/w of the total tablet weight.

A chewable tablet as described herein will also contain a disintegrant or blend of disintegrants in the range of about 1% w/w to about 15% w/w, or about 5% w/w to about 10% w/w, or about 7% w/w to about 8% w/w based on the total tablet weight. Suitable disintegrants include, e.g., Crospovidone, Sodium starch glycolate, Croscarmellose sodium, Carboxymethyl cellulose sodium, Carboxymethylcellulose calcium, Starch. In one embodiment, a tablet as described herein contains crospovidone in a range of about 5% w/w to about 10% w/w. or about 7.5% w/w based on the tablet weight prior to any non-functional coating being applied.

The binder for the chewable tablet may be absent (i.e., 0%), or optionally, present in an amount of about 1% w/w to about 15% w/w of the total tablet weight. Examples of suitable binders include polyvinylpyrrolidone (Povidone), Hydroxypropyl methyl cellulose, Hydroxypropyl cellulose, Hydroxyethyl cellulose, Hydroxyethyl cellulose, Methyl cellulose, Polyvinyl alcohol, Starch, Acacia, Alginic acid, Sodium alginate.

In one embodiment, the chewable tablet of the invention contains a sweetener in an amount of about 0.01% w/w to about 3% w/w, or about 0.5% w/w to about 2% w/w, or about 1% w/w to about 2% w/w or about 1.5% w/w, based on the total tablet weight exclusive of any optional non-functional coating. Suitable sweeteners may include, e.g., Aspartame, Saccharin, Saccharin sodium, Sucralose, Sodium cyclamate, Xylitol, Acesulfame Potassium, and blends thereof. Optionally, in addition to functioning as a sweetener, an excipient may function as a filler. Examples of suitable sweeteners/fillers including, e.g., fructose, sucrose, xylitol, maltitol. Optionally, when performing both functions, the excipient may be present in an amount in excess of about 10% w/w of the tablet. In such an instance, additional sweetener may be omitted (e.g., present in 0% added sweetener). Alternatively, a second sweetener or a combination of sweeteners which differs from the filler is added in the amount provided in this paragraph in order to further enhance taste.

Suitably, the tablet is provided with a buffering agent in an amount of about 0.1% w/w to about 5% w/w, or about 0.5% w/w to about 1.5% w/w based on the total tablet weight. Examples of suitable buffering agents include, e.g., citric acid, tartaric acid, malic acid, lactic acid, and acceptable salts thereof, and mixtures thereof. In one embodiment, the buffering agent adjust the pH of the tablet (if suspended in water) to a range of about 3.5 to about 5, or about 4 to about 4.5. In one embodiment, the buffering agent is citric acid, which also provides desirable taste properties.

When an additional flavoring agent is added, the flavoring agent(s) may be added in an amount of about 0.05% w/w to about 3% w/w, or about 0.1% to about 1% w/w or about 0.5% w/w, based on the total weight of the tablet (exclusive of any optional non-functional coating). Suitable flavoring agents may include, both natural and artificial flavoring agents such as are generally available through several custom manufacturers around the world such as Fona [Illinois, US], Givaudan (Vernier, Switzerland), Ungerer & Company (Lincoln Park, N.J.), and International Flavors & Fragrances (New York, N.Y.) to name a few. Those skilled in the art will recognize that there are several commercial sources available including custom blenders. The flavorings may be blended prior to addition to the pharmaceutical composition or added separately. Still other flavoring agents such as cherry, strawberry, vanilla, grape, banana and other flavors or mixtures thereof may be selected.

Optionally, a colorant may be provided to the tablet to provide a desired visual appeal or trade dress. Such colorants may be added in the range of about 0.001 to about 1% w/w, or about 0.01% w/w to about 0.08% w/w or about 0.05% w/w, based on the total weight of the tablet (exclusive of any non-functional coating). Such colorants are available from a variety of sources including, e.g., Colorcon, Noveon, and Spectra.

In order to facilitate production of the chewable tablet, excipients such as lubricants and glidants may be utilized. A lubricant may be utilized in an amount of about 0.1% w/w to about 5% w/w, about 0.2% w/w to about 4.5% w/w, or about 1.5% w/w to about 3% w/w of the total weight of the tablet. Examples of lubricants may include, e.g., Talc, Magnesium Stearate, sodium stearyl fumarate, Stearic acid, Zinc Stearate, Calcium Stearate, Magnesium trisilicate, Polyethylene glycol, and blends thereof. In one embodiment, talc and magnesium stearate are used in tablet preparation. The resulting tablet may contain about 0.1% w/w to about 3% w/w talc and about 0.5% w/w to about 0.5% w/w magnesium stearate. A glidant may be used in an amount of about 0.01% w/w to about 0.5% w/w, or about 0.1% w/w to about 0.3% w/w, based on the total weight of the tablet. Examples of suitable glidants include, e.g., silicon dioxide and tribasic calcium phosphate. In one embodiment, the glidant is silicon dioxide which is used in an amount of about 0.001% w/w to about 0.1% w/w or about 0.05% w/w.

Optionally, other excipients may be selected from conventional pharmaceutically acceptable carriers or excipients and well established techniques. Without being limited thereto, such conventional carriers or excipients include diluents, binders and adhesives (i.e., cellulose derivatives and acrylic derivatives), lubricants (i.e., magnesium or calcium stearate, or vegetable oils, polyethylene glycols, talc, sodium lauryl sulfate, polyoxy ethylene monostearate), thickeners, solubilizers, humectants, disintegrants, colorants, flavorings, stabilizing agents, sweeteners, and miscellaneous materials such as buffers and adsorbents in order to prepare a particular pharmaceutical composition. The stabilizing agents may include preservatives and anti-oxidants, amongst other components which will be readily apparent to one of ordinary skill in the art.

The following Table provides exemplary formulations of MPH extended release chewable tablets according to the invention, based on the total weight of the tablet.

| Component | Broad Range w/w | Narrower Range |
|---|---|---|
| Coated MPH-ion exchange resin complex (coated MPH polistirex) | 15%-20% | 16%-18% |
| Uncoated MPH polistirex | 1.5%-3.5% | 2%-3% |
| Uncomplexed MPH | 0.5%-0.9% | 0.6%-0.8% |
| Filler(s) | 45%-85% | 50%-70% |
| Mannitol | 40%-60% | 45%-55% |
| Xanthan Gum | 0.1%-1% | 0.25%-0.75% |
| MCC + guar gum | 5%-25% | 10%-20% |
| Disintegrant(s) | 5%-10% | 7%-8% |
| Binder(s) | 0%-8% | 2%-6% |
| Sweetener(s) | 0.5%-3% | 1%-2% |
| Buffering Agent | 0.1%-5% | 0.5%-1.5% |
| Flavoring Agent | 0.1%-3% | 0.1%-1% |
| Lubricant(s) | 0.2%-4.5% | 1.5%-3% |
| Talc | 0.1%-3% | 1%-2% |
| Magnesium stearate | 0.1%-1.5% | 0.5%-1% |
| Glidant | 0.01%-1% | 0.1%-0.3% |
| Colorant | 0.01%-0.5% | 0.02%-0.08% |

Suitably, a chewable tablet of the invention is prepared as a single uniform solid dispersion. A typical manufacturing process for making a chewable tablet generally involves blending of the desired ingredients to form a uniform distribution of the coated MPH—ion exchange resin complex, the uncoated MPH—ion exchange complex, the uncomplexed MPH, and the excipients. If desired, a blend of the three MPH components may be formed prior to blending into the excipient. The blend is then compressed into a single layer using standard methods and tablet presses such as well-known to those skilled in the art (e.g., Kilian, Fette, Kirsch, Elizabeth, Sejong, Kikisui, SMI, Colton, Stok, and Manesty, amongst others.)

The working examples below describe forming a chewable tablet of the invention into a capsule shape, optionally with a single bisect (a single scoring at the mid-line which facilitates splitting the tablet into halves). However, other shapes may be readily selected, including, e.g., a standard round shape, a flat faced shape, oval, bullet, square, triangle, diamond, pentagon, octagon, amongst others. Optionally, one or more of these tablet shapes may be provided with a quadrisect, i.e., two perpendicular scores which facilitate splitting the tablet into quarters.

Optionally, the tablet may have one or more sealant or top coating which does not function to modify or extend release but which provides moisture barrier, of a color coating or other visual appeal. For example, such a coating may provide a "shine" to the tablet, enhance palatability, serve as an identifying color for the tablet, or other purposes. Such coatings are available commercially, e.g., from Colorcon or other suppliers. Typically, such a coating is composed of hydroxypropylmethylcellulose (HPMC) or polyvinylalcohol and is present in an amount of about 1% w/w to about 20% w/w, or about 2% w/w to about 10% w/w of the total tablet weight.

The finished tablets may be stored in glass or high density polyethylene (HDPE) bottles with or without a heat induced sealed (HIS) bottle. The bottle may also contain a dessicant. Alternatively, the tablets may be encapsulated into blister packs using standard methods well-known to those skilled in the art.

An MPH extended release chewable tablet of the invention may be orally administered to a patient having a disorder treatable by MPH. These include disorders for which regulatory approval has been granted in the US or other jurisdiction in which the drug is being administered and which requires regulatory approval. For example, MPH is currently approved for treatment of Attention Deficit Hyperactivity Disorder (ADHD), postural orthostatic tachycardia syndrome, and narcolepsy. MPH has also been described in patent applications and in the literature as being useful for treatment of such disorders including, but are not limited to, behavioral disorders, treatment-resistant cases of lethargy, depression, neural insult, obesity, and rarely other psychiatric disorders such as obsessive-compulsive disorder, Attention Deficit Disorder, specific dyslexias, brain dysfunction, cognitive decline in AIDS and AIDS related conditions, alertness in geriatric, Alzheimer's patients and recovering stroke victims.

Thus, the invention provides a method of treating one or more of the above disorders for a period of at least twelve hours by administering a MPH extended release chewable tablet containing a blend of a barrier coated methylphenidate—ion exchange resin complex—matrix, a first MPH immediate release component (e.g., an uncoated MPH—ion exchange resin complex), and a second MPH immediate release component (uncomplexed MPH).

A composition of the invention is formulated to deliver MPH is, most desirably, in dosages ranging from about 1 mg up to about 100 mg per day, preferably from about 10 to about 75 mg per day, or in about 25 or 60 mg doses [based on equivalence to racemic methylphenidate HCl] although variations will necessarily occur depending upon the weight and condition of the subject being treated and the particular route of administration chosen. Actual dosages of dexmethylphenidate may be at half the amounts of racemic methylphenidate. Variations may nevertheless occur depending upon the weight and condition of the persons being treated and their individual responses to said medicament.

As described herein, the MPH extended release chewable tablets of the invention can be dosed orally twice-a-day at 12-hour intervals. However, depending upon the patient, smaller doses may be delivered at intervals during the day. Other patients may take a single dose in the morning and forego dosage in the evening.

An in vitro dissolution test determines whether chewable tablets disintegrate within a prescribed time when placed in a dissolution media under prescribed experimental conditions. Disintegration is defined as the state in which no residue of the tablet, except fragments of undissolved coating, remains on the screen of the test apparatus or, if any other residue remains, it consists of a soft mass having no palpably firm, unmoistened core.

Suitable methods for in vitro testing of chewable tablet dissolution have been described, e.g., by the World Health Organization (WHO) International Pharmacopoeia, (http://www.who.int/medicines/publications/pharmacopoeia/). An example of a suitable disintegration apparatus is described as follows. The apparatus consists of a circular basket-rack assembly, a suitable vessel for the immersion fluid (such as a 1-litre beaker), a thermostatic arrangement for maintaining the fluid at the required temperature (normally 37±2° C.), and a device for raising and lowering the basket-rack in the immersion fluid at a constant frequency of 28-32 cycles/min through a distance of 50-60 mm The basket-rack assembly consists of six open-ended cylindrical glass tubes and a rack for holding them in a vertical position. The tubes are 75-80 mm long, and have an inside diameter of about 21.5 mm and a wall about 2 mm thick. The tubes are held vertically by two superimposed plates, circular in shape and made of transparent plastic material, each about 90 mm in diameter and 6 mm thick, perforated by six holes of a diameter that allows the tubes to be inserted. The holes are equidistant from the center of the plate and equally spaced one from another. A piece of woven gauze, made of stainless steel wire about 0.635 mm in diameter, with a mesh aperture of 2.0 mm is attached to the underside of the lower plate. The upper plastic plate is covered with a stainless steel plate, about 1 mm thick, of a diameter similar to that of the plastic plates. The steel plate is perforated by six holes about 22 mm in diameter, positioned to coincide with those of the upper plastic plate. It is placed over the tubes and consolidates the whole structure. The plates are held rigidly 75-80 mm apart by vertical stainless steel rods at the periphery. A metal rod is fixed to the center of the upper plate. This enables the assembly to be attached to a suitable mechanical device so that it may be lowered and raised. The volume of the fluid in the immersion vessel should be such that, at the highest point of the upward stroke, the wire mesh that forms the bottom of the basket remains at least 25 mm below the surface of the fluid. At the lowest point of the downward stroke, it should descend to not less than 25 mm from the bottom of the vessel. The time required for the upward stroke should be equal to the time required for the downward stroke, and the change in stroke direction should be a smooth transition rather than an abrupt reversal of motion. Where a disc is prescribed in the monograph, the following configuration and dimensions apply: a cylindrical disc 20.7±0.15 mm in diameter and 9.5±0.15 mm thick, made of transparent plastic with a relative density of 1.18 to 1.20. Each disc is pierced by five holes 2 mm in diameter, one in the center and the other four spaced equally on a circle of radius 6 mm from the center of the disc. On the lateral surface of the disc, four equally spaced grooves are cut so that on the upper surface of the disc they are 9.5 mm wide and 2.55 mm deep and, at the lower surface, 1.6 mm square. Different designs of basket-rack assembly may be used, provided that the specifications for the glass tubes and the stainless steel wire gauze are maintained. In vitro dissolution of the methylphenidate chewable tablet of the invention may be assessed through a variety of methods including, e.g., Food and Drug Administration (FDA)—accepted dissolution tests, including the Basket Method (I) approved for use with a methylphenidate chewable tablet, http://www.accessdata.fda.gov/scripts/cder/dissolution/dsp_SearchResults_Dissolutions.c fm, have been described. The current FDA-approved dissolution test for a prior art methylphenidate chewable tablet utilizes water and a paddle speed of 100 rpm, at 900 mL, with testing at 15, 30, 45 and 60 minutes. Other methylphenidate tablets have different dissolution tests and different media. However, since the barrier coated methylphenidate—ion exchange complex described herein is not readily soluble in water, the previously described tests are dissolution medium is not suitable for testing dissolution of the present tablets at those time frames. Accordingly, a dissolution medium of phosphate buffer is utilized in the working examples below to assess in vitro dissolution of the MPH extended release chewable tablets described herein of the invention rather than water.

Suitably, the MPH extended release tablet of the invention can be scored without affecting the extended release profile. Thus, the oral dose is readily titrated, i.e., split in half, in order to readily and accurately deliver half the dose of the finished tablet.

EXAMPLES

The following examples are illustrative only and are not intended to be a limitation on the present invention.

Example 1

Methylphenidate (MPH) Extended Release (ER) Chewable Tablets (CT) Prepared Using a Blend of Eudragit® RS 30D and Eudragit® RL 30D Polymer as Barrier Coating for Sustained Release Component In the below example the Finished product, MPH ERCT—20 mg contains 70% of the dose as Coated (Eudragit® RS 30D and Eudragit® RL 30D) MPH Polistirex Matrix, 15% of dose as Uncoated MPH Polistirex and 15% of the dose as MPH HCl.

| A. Coated Methylphenidate Polistirex | |
|---|---|
| Ingredients | Quantity |
| Uncoated Methylphenidate-Ion exchange resin complex (Uncoated MPH Polistirex) | |
| Methylphenidate (MPH) HCl (Covidien) | 3100 g |
| Sodium Polystyrene Sulfonate Amberlite ® IRP69 ion exchange resin [Rohm Haas] | 7693 g |
| Purified Water* | Qs* |
| Pre-Coated MPH Polistirex | |
| Uncoated MPH Polistirex | 8500 g |
| Povidone [Kollidon ® K30, BASF] | 657 g |
| Purified water* | 2629 g |
| Purified Water* | Qs* |
| Coated MPH Polistirex | |
| Pre-coated MPH Polistirex-(Povidone) Matrix | 600 g |
| Poly(ethyl acrylate-co-methyl methacrylate- | 75.26 g |

| A. Coated Methylphenidate Polistirex | |
|---|---|
| Ingredients | Quantity |
| co-trimethylammonioethyl methacrylate chloride) 1:2:0.2 [Eudragit ® RL30D dispersion**, Evonik] | |
| Poly(ethyl acrylate-co-methyl methacrylate-co-trimethylammonioethyl methacrylate chloride) 1:2:0.1 [Eudragit ® RS30D dispersion**, Evonik] | 376.3 g |
| Triethyl Citrate | 27.0 g |
| Talc | 33.87 g |
| Purified Water* | 694.56 g |

*Removed during processing
**30% w/w aqueous dispersion

1. Uncoated Methylphenidate Polistirex

The MPH—ion exchange resin complex (MPH polistirex), was prepared by first adding 80 L of Purified Water into a PEF 450 PallSchenk vessel and dissolving methylphenidate HCl by continuous mixing. Sodium Polystyrene Sulfonate ion exchange resin [Amberlite® IRP69, Rohm &Haas] was dispersed with continuous mixing and the mixing was continued for 60 minutes. Water was removed by filtration process followed by rinsing twice using purified water (40L). Wet resin complex was then dried until moisture content was between 3-7%. Dried MPH—ion exchange resin complex was passed through a 40 mesh screen using the CO-MIL® device. This was the Uncoated MPH Polistirex.

In a separate container Povidone (polyvinylpyrrolidone) was dissolved in 2629 gms of Purified Water (Povidone solution). Uncoated MPH Polistirex prepared as described earlier in this example was treated with Povidone solution with continuous mixing to form a uniform mass of uncoated MPH polistirex in a matrix with the povidone. The uncoated MPH polistirex—matrix was dried until the moisture content was between 15-25%. Semi-dried MPH polistirex—matrix was then milled using CO-MIL® brand mill fitted with 40 mesh screen. Milled MPH polistirex—matrix was further dried until moisture content was between 3-7%. Dried MPH polistirex—matrix was passed through a CO-MIL® fitted with 40 mesh screen. This was the Pre-Coated MPH Polistirex—Matrix.

The Coated MPH Polistirex—Matrix was prepared as follows. The coating solution was prepared by mixing Purified water and Triethyl Citrate in a container and later Talc was dispersed using high shear mixer for 10 minutes (Talc dispersion). In a separate container Eudragit® RS 30D and Eudragit® RL 30D were added and mixed with Talc dispersion for 45 minutes. The coating process was performed in a fluid bed processor equipped with Wurster column by applying coating solution on to Pre-coated MPH Polistirex—Matrix that resulted in 30% weight gain. The Coated MPH Polistirex—Matrix was again passed through Sieve No. 40 mesh screen.

| B. Methylphenidate ER Chewable Tablets | |
|---|---|
| Ingredients | qty/batch (g) |
| Coated MPH Polistirex-(Povidone) Matrix from Part A | 60.45 |
| Uncoated MPH Polistirex from Part A | 8.01 |
| MPH HCl | 2.25 |
| Mannitol | 145.44 |
| Xanthan gum | 1.5 |

-continued

B. Methylphenidate ER Chewable Tablets

| Ingredients | qty/batch (g) |
|---|---|
| Crospovidone | 22.5 |
| Microcrystalline Cellulose and Guar gum [Avicel ® FMC Biopolymer, 80:20 weight ratio of MCC to guar gum] | 45 |
| Aspartame | 4.5 |
| Citric acid | 3 |
| Flavor | 1.5 |
| Talc | 3 |
| Silicon dioxide | 0.6 |
| Magnesium stearate | 2.25 |

Mannitol and Microcrystalline Cellulose and Guargum were screened through 20 mesh screen and loaded into the cube blender. Coated MPH Polistirex—Matrix prepared as in the previous section, Uncoated MPH Polistirex, MPH HCl, Xanthan gum, Crospovidone, Aspartame, Citric acid, Flavor, Talc, Silicon dioxide were screened through 40 mesh screen and loaded into the cube blender and mixed for 10 minutes. Magnesium Stearate was screened through 40 mesh screen and loaded into the blender and mixed for additional 5 minutes. The powder blend was compressed on a 10 station rotary tablet press using 0.2625×0.5720 capsule shaped tooling. The final weight of the compressed tablet was 400 mg.

Example 2

Methylphenidate ER Chewable Tablets Prepared Using a Cured Polyvinylacetate—Plasticizer Barrier Coating for Sustained Release Component In the below example the Finished product, MPH ERCT—40 mg contains 70% of the dose as Coated (Kollicoat SR 30D) MPH Polistirex—Matrix, 15% of dose as Uncoated MPH Polistirex and 15% of the dose as MPH HCl.

A. Coated Methylphenidate Polistirex

| Ingredients | Quantity |
|---|---|
| Uncoated Methylphenidate Polistirex | |
| MPH HCl | 15500 g |
| Sodium Polystyrene Sulfonate Amberlite ® IRP69 ion exchange resin | 38450 g |
| Purified Water* | Qs* |
| Pre-Coated MPH Polistirex | |
| Uncoated MPH Polistirex | 4000 g |
| Povidone (Kollidon ® K30; BASF) | 3092 g |
| Purified water* | 12372 g |
| Purified Water* | Qs* |
| Coated MPH Polistirex | |
| Pre-coated MPH Polistirex-(Povidone) Matrix | 34000 g |
| Polyvinyl Acetate Dispersion** (Kollicoat ® SR30D, BASF) | 34300 g |
| Triacetin | 513 g |
| Purified Water* | 19200 g |

*Removed during processing
**30% w/w aqueous dispersion

The MPH—ion exchange resin complex (MPH polistirex) was prepared by first adding 400 L of Purified Water in to a large scale multi-purpose vessel and MPH HCl was dissolved by continuous mixing. Sodium Polystyrene Sulfonate ion exchange resin was dispersed with continuous mixing and the mixing was continued for 60 minutes. Water was removed by filtration process followed by rinsing twice using purified water. Wet MPH polistirex was then dried until the moisture content was between 3-7%. Dried MPH polistirex was passed through a 40 mesh screen using the CO-MIL®. This was the Uncoated MPH Polistirex.

In a separate container Povidone was dissolved in 12372 gms of Purified Water (Povidone solution). Uncoated MPH Polistirex was treated with Povidone solution with continuous mixing to form a uniform mass to provide an uncoated MPH polistirex in a matrix with the povidone. Wet mass was dried until the moisture content was between 15-25%. Semi-dried uncoated MPH polistirex—(povidone) matrix was then milled using CO-MIL® fitted with a 40 mesh screen. Milled material was further dried until moisture content was between 3-7%. Dried uncoated MPH polistirex—(povidone) matrix was passed through a CO-MIL® fitted with 40 mesh screen. This was the Pre-Coated MPH Polistirex—(povidone) matrix.

The Coated MPH Polistirex—Matrix was prepared as follows. The coating solution was prepared by mixing Triacetin, Purified Water and Polyvinyl Acetate dispersion in a separate container. The coating process was performed in a fluid bed processor equipped with Wurster column by applying coating solution on to Pre-coated MPH Polistirex that resulted in 30% weight gain. The Coated MPH Polistirex—Matrix was placed in the hot air oven at 60° C. for 5 hours. The Coated MPH Polistirex—Matrix was again passed through Sieve No. 40 mesh screen. This was the cured, coated MPH Polistirex-Matrix.

B. Methylphenidate ER Chewable Tablets

| Ingredients | quantity/batch (g) |
|---|---|
| Cured, Coated MPH Polistirex-Matrix from Example 2 Part A | 16576 |
| Uncoated MPH Polistirex from Example 2 Part A | 2534 |
| MPH HCl | 720 |
| Mannitol | 48810 |
| Xanthan gum | 480 |
| Crospovidone | 7200 |
| Microcrystalline Cellulose and Guar gum [Avicel ® FMC Biopolymer; 80:20 MCC to guar gum ratio by weight] | 14400 |
| Aspartame | 1440 |
| Citric acid | 960 |
| Flavor | 480 |
| Colorant | 48 |
| Talc | 1440 |
| Silicon dioxide | 192 |
| Magnesium Stearate | 720 |

Mannitol and Microcrystalline Cellulose and Guargum were screened through 20 mesh screen and loaded into the 'V' blender. Cured, coated MPH Polistirex—Matrix, Uncoated MPH Polistirex, MPH HCl, Xanthan gum, Crospovidone, Aspartame, Citric acid, Flavor, Talc, Silicon dioxide were screened through 40 mesh screen, Colorant was screened through 60 mesh and loaded into the 'V' blender and mixed for 10 minutes. Magnesium Stearate is screened through 40 mesh screen and loaded into the blender and mixed for additional 5 minutes. The resulting powder blend was compressed on a 36 station rotary tablet press using a 0.3310×0.7210 capsule shaped tooling to produce a capsule shaped compressed MPH extended release (ER) chewable tablet. The final weight of the compressed tablet was 800 mg.

| C. Non-functional Coating of MPH ER Chewable Tablet | |
|---|---|
| Ingredients | quantity/batch (g) |
| Opadry ® (polyvinylalcohol) | 4020 |
| Purified water | 36180 |

In a separate container Opadry® polymer was dispersed in 36180 gm of purified water and mixed for 45 minutes. The coating process was performed in a perforated coating pan by applying coating solution on to the compressed MPH ER Chewable Tablets that resulted in 3% weight gain.

Example 3

Methylphenidate ER Chewable Tablets Prepared Using a Cured Polyvinylacetate—Plasticizer Barrier Coating for Sustained Release Component In the below example the Finished product, MPH ERCT—40 mg contains 80% of the dose as Coated MPH Polistirex (Kollicoat® SR 30D), 10% of dose as Uncoated MPH Polistirex and 10% of the dose as MPH HCl.

| A. Coated Methylphenidate Polistirex | |
|---|---|
| Ingredients | Quantity |
| Uncoated MPH Polistirex | |
| Methylphenidate HCl | 15500 g |
| Sodium Polystyrene Sulfonate Amberlite ® IRP69 ion exchange resin [Rohm Haas] | 38450 g |
| Purified Water* | Qs* |
| Pre-Coated MPH Polistirex | |
| Uncoated MPH Polistirex | 30000 g |
| Povidone (Kollidon ® K30) | 2319 g |
| Purified water* | 10940 g |
| Purified Water* | Qs* |
| Coated MPH Polistirex | |
| Pre-coated MPH Polistirex-(Povidone) Matrix | 32000 g |
| Polyvinyl Acetate Dispersion** (Kollicoat ® SR30D, BASF) | 32300 g |
| Triacetin | 483 g |
| Purified Water* | 18100 g |

*Removed during processing
**30% w/w aqueous dispersion

A MPH—ion exchange resin complex (MPH Polistirex) was prepared by first adding 400 L of Purified Water in to the vessel and dissolving methylphenidate HCl by continuous mixing. Sodium Polystyrene Sulfonate ion exchange resin was dispersed with continuous mixing and the mixing was continued for 60 minutes. Water was removed by filtration process followed by rinsing twice using purified water. Wet MPH polistirex was then dried until moisture content was between 3-7%. Dried MPH polistirex was passed through a 40 mesh screen using the CO-MIL® brand mill. This was the Uncoated MPH Polistirex.

In a separate container Povidone was dissolved in 10940 gms of Purified Water (Povidone solution). Uncoated MPH Polistirex complex was treated with Povidone solution with continuous mixing to form a uniform mass which resulted in the formation of a matrix between the uncoated MPH polistirex and povidone. The wet mass containing the uncoated MPH polistirex—matrix was dried until the moisture content was between 15-25%. Semi-dried uncoated MPH polistirex—matrix was then milled using CO-MIL® brand mill fitted with a 40 mesh screen. Milled uncoated MPH polistirex—matrix was further dried until moisture content was between 3-7%. Dried material was passed through a CO-MIL fitted with 40 mesh screen. This was the Pre-Coated MPH Polistirex—matrix.

The Coated MPH Polistirex—Matrix was prepared as follows. The coating solution was prepared by mixing Triacetin, Purified Water and Polyvinyl Acetate dispersion in a separate container. The coating process was performed in a fluid bed processor equipped with Wurster column by applying coating solution on to Pre-coated MPH Polistirex—Matrix that resulted in 30% weight gain. The Coated MPH Polistirex—Matrix was placed in the hot air oven at 60° C. for 5 hours. The cured, coated MPH Polistirex—Matrix was again passed through number 40 mesh screen. This was the cured, coated MPH Polistirex—Matrix used for preparing the chewable tablet.

| B. Methylphenidate ER Chewable Tablets | |
|---|---|
| Ingredients | quantity/batch (g) |
| Cured, Coated Methylphenidate Polistirex-Matrix prepared according to Example 3 Part A | 59.19 |
| Uncoated Methylphenidate Polistirex prepared according to Example 3 Part A | 5.34 |
| Methylphenidate Hydrochloride | 1.5 |
| Mannitol | 149.97 |
| Xanthan gum | 1.5 |
| Crospovidone | 22.5 |
| Microcrystalline Cellulose and Guar gum [Avicel ® FMC Biopolymer] | 45 |
| Aspartame | 4.5 |
| Citric acid | 3 |
| Flavor | 1.5 |
| Colorant | 0.15 |
| Talc | 3 |
| Silicon dioxide | 0.6 |
| Magnesium Stearate | 2.25 |

Mannitol and Microcrystalline Cellulose and Guargum were screened through 20 mesh screen and loaded into the 'V' blender. Coated Methylphenidate Polistirex, Uncoated Methylphenidate Polistirex, Methylphenidate Hydrochloride, Xanthan gum, Crospovidone, Aspartame, Citric acid, Flavor, Talc, Silicon dioxide were screened through 40 mesh screen, Colorant was screened through 60 mesh and loaded into the 'V' blender and mixed for 10 minutes. Magnesium Stearate is screened through 40 mesh screen and loaded into the blender and mixed for additional 5 minutes. The powder blend was compressed on a 36 station rotary tablet press using 0.3310×0.7210 capsule shaped tooling. The final weight of the compressed tablet was 800 mg.

| C. Non-functional Coating of MPH ERCT | |
|---|---|
| Ingredients | quantity/batch (g) |
| Opadry ® (polyvinylalcohol) | 10 |
| Purified water | 90 |

In a separate container Opadry® polyvinylalcohol non-functional coating was dispersed in 90 gm of purified water and mixed for 45 minutes. The coating process was performed in a perforated coating pan by applying coating solution on to the compressed MPH ER Chewable Tablets that resulted in 3% weight gain.

The scored chewable tablet when split, is expected to show the extended release profile as is characteristic of the intact tablet in vitro. The following example shows the in vitro dissolution profiles of split versus whole tablet of the 20 mg and 30 mg methylphenidate ER chewable tablets.

Example 4

Methylphenidate Extended Release Chewable Tablet

A. Split Tablet Dissolution

The tablets used in this study are the same ingredients as described in Example 2 for a 40 mg tablet, with the exception of the non-functional cosmetic coating. In order to prepare the 20 mg tablet used in this study, the same three MPH components and the same excipients as identified in Example 2 were combined at ½ the weight percentages of each ingredient defined in Example 2. In order to prepare the 30 mg tablet used in this study, the same three MPH components and the same excipients as identified in Example 2 were combined at ¾ the weight percentages of each ingredient identified in Example 2.

The following in vitro dissolution assessment was performed using conventional USP testing on the whole (un-scored) or split tablets placed in 900 mL 0.4 M potassium phosphate buffer (KH$_2$PO$_4$) at 37±0.5° C. with a USP paddle speed of 75 rpm. This assessment was designed to show the in vitro dissolution rate over a twelve hour period.

| | % Dissolved | | | | | | |
|---|---|---|---|---|---|---|---|
| Form | 0.5 h | 1 h | 2 h | 3 h | 6 h | 8 h | 12 h |
| 20 mg, whole tablet | 46 | 55 | 66 | 72 | 84 | 88 | 92 |
| 20 mg Tablet Split in Half | 44 | 53 | 65 | 71 | 82 | 85 | 89 |
| 30 mg, whole tablet | 46 | 55 | 67 | 74 | 85 | 90 | 94 |
| 30 mg Tablet, Split in Half | 47 | 57 | 69 | 76 | 89 | 93 | 97 |

B. Comparative Dissolution Study

In another dissolution study, the 40 mg methylphenidate ER chewable tablet, prepared as described in Example 2, was compared to MPH ER chewable tablets with the sustained release component and only one of the two immediate release components. Thus, 40 mg tablet was prepared with the same excipients in Example 2, but having a combination of the coated MPH polistirex—matrix and only the faster release MPH immediate release component (racemic MPH HCl). The MPH HCl is present in double the weight amount described in Example 2 and the slower release uncoated MPH polistirex is absent. This is the 70/30 coated/MPH HCl tablet shown in the table below. The second comparative 40 mg tablet contains the same excipients as in Example 2, but in contrast to Example 2, the active components are a combination of the coated MPH polistirex—matrix and double the weight amount of the slower release MPH immediate release component (uncoated MPH polistirex); no MPH HCl is included in this formulation. This is the 70/30 coated/uncoated tablet shown in the table below.

Each of the three active components is prepared as described in Example 2. Each of the tablets are prepared as described in Example 2, with the exception of the weights of the immediate release components showing the comparative two-component tablets.

In order to enhance the ability to observe the onset of release within 60 minutes, another study to monitor first hour of dissolution every 10 minutes was used than that described in Example 4A for the split tablet dissolution. With the exception of the buffer strength, the in vitro dissolution assessment was performed as described in Part A above by placing the tablets in 900 mL of the buffer at 37±0.5° C. and using a USP paddle speed of 75 rpm.

| | % Dissolved | | | | |
|---|---|---|---|---|---|
| Form | 10 min | 20 min | 30 min | 45 min | 60 min |
| 70/30 (coated cured MPH polistirex-matrix/MPH HCl) | 30 | 31 | 32 | 33 | 35 |
| 70/15/15 (coated cured MPH polistirex-matrix/uncoated MPH polistirex/MPH HCl) Tablet of Example 2 | 25 | 28 | 30 | 32 | 33 |
| 70/30 (coated cured MPH polistirex-matrix/uncoated MPH polistirex) | 21 | 25 | 27 | 29 | 30 |

The initial dissolution profiles show the order of release rate as: coated/MPH HCl>coated/uncoated/MPH HCl>coated/uncoated. The inclusion of MPH HCl to replace a portion of uncoated showed increase in the initial release rate.

C. Compression Pressure Dissolution Study

The chewable tablets when compressed under the pressure of 8 to 23 kp, show no difference in the release profile of the methylphenidate ER chewable tablets. The dissolution study was performed as described in Example 4A. An example of the release rate of the 40 mg formula of Example 2 is listed in the following table. These tested hardness are not limitations on the chewable tablet, but are illustrative only.

| Methylphenidate ERCT, 40mg (70/15/15)-Hardness study % Dissolved | | | | | | | |
|---|---|---|---|---|---|---|---|
| 0.5 h | 1 h | 2 h | 3 h | 6 h | 8 h | 12 h | Comments |
| 47 | 56 | 67 | 74 | 86 | 89 | 92 | 8-10 kp, Low Hardness |
| 46 | 55 | 66 | 74 | 86 | 90 | 93 | 14-16 kp, Normal Hardness |
| 47 | 56 | 67 | 75 | 87 | 90 | 93 | 20-23 kp, High Hardness |

Example 5

Single Dose Pharmacokinetics of an Extended Release Methylphenidate Chewable Tablet A three-way cross-over pharmacokinetic study has been performed using (1) MPH ER chewable tablets prepared according to Example 2 of this specification (Test) dosed 40 mg at 0 hour under fasted condition (2) MPH ER chewable tablets prepared according to Example 2 of this specification (Test) dosed 40 mg under fed condition and (3) IR chewable tablets (reference) [Methylin® 10 mg chewable tablet; Shionogi Inc] dosed 20 mg at 0 and 6 hours under fasted condition.

|  | Calories (kcal) | Total fat (g) | Carbohydrate (g) | Protein (g) |
|---|---|---|---|---|
| 250 mL of whole milk | 160 | 8 | 12 | 8 |
| 2 slices of bacon | 89 | 7 | 0 | 6 |
| Total weight |  | 56 | 85 | 36 |
| Total calories (kcal) |  | 504 | 340 | 144 |
| Related caloric content |  | 50.6% | 34.1% | 14.4% |

The objective is to determine the relative bioavailability of MPH ER chewable tablets of the invention product versus reference and to also evaluate the food effect on the chewable tablets of the invention.

This is an open-label, single- and multi-dose, randomized, 3-period, 3-sequence, 3-treatment, crossover study, designed to evaluate the relative bioavailability of two formulations of methylphenidate HCl extended release chewable tablets, administered to healthy male and female subjects under fasting and fed conditions. Subjects were randomly assigned to one of the three dosing sequences ABC, BCA, and CAB. Concentrations of total (racemic) methylphenidate were measured from samples collected over a 24-hour interval after dosing in each period. Thirty-three (33) subjects were dosed in Period 1. All 33 subjects are included in the safety dataset. Thirty-two (32) subjects were dosed in Period 2. Thirty (30) subjects were dosed in Period 3. Thirty-one (31) subjects are included in the pharmacokinetic analysis and the statistical analyses. Subjects 10 (ABC) and 18 (CAB) completed only Period 1 of the study. These subjects were not included in the pharmacokinetic dataset. Subjects 29 (ABC) and 33 (ABC) completed Periods 1 and 2, receiving Treatments A and B. Both subjects are included in the pharmacokinetic dataset.

Pharmacokinetics:

The following pharmacokinetic parameters were estimated using a non-compartmental approach: $C_{max}$, $AUC_t$, $AUC_{inf}$; AUC0-0.5, AUC0-2, AUC0-3, AUC0-4, $T_{max}$, Kel, and $T_{half}$.

Safety:

An assessment of safety was based primarily on the frequency and severity of AEs. There was no formal evaluation of safety or tolerability.

Statistical Methods:

Descriptive statistics are estimated for the pharmacokinetic parameters in each treatment.

Analysis of variance (ANOVA) was performed on log-transformed $C_{max}$, $AUC_t$, $AUC_{inf}$, AUC0-0.5, AUC0-2, AUC0-3, AUC0-4 and on untransformed $T_{max}$, Kel and $T_{half}$ parameters. The significance of the sequence, period, treatment and subject-within-sequence effects was tested.

Using the same statistical model, the least-squares-means, the differences between the treatments least-squares-means and the corresponding standard errors of these differences were estimated for log-transformed $C_{max}$, $AUC_t$, $AUC_{inf}$, AUC0-0.5, AUC0-2, AUC0-3, AUC0-4 parameters. Based on these statistics, the ratios of the geometric means for treatments and the corresponding 90% confidence intervals were calculated for the following contrasts:

Treatment A versus Treatment C (relative bioavailability under fasting conditions)

Treatment B versus Treatment A (food effect for the test formulation) Summary-Conclusions:

Pharmacokinetic and Statistical Results of MPH ER Chewable Tablets 40 mg Versus Methylin™ 10 mg Chewable Tablets

| MPH | Geometric Mean | | Ratio (%) | 90% Confidence Limits | | Intra-Sub CV (%) |
|---|---|---|---|---|---|---|
|  | Test | Reference |  | Lower | Upper |  |
| $C_{max}$ (ng/mL) | 12.1 | 15.1 | 80.0 | 76.3 | 83.9 | 11 |
| $AUC_{(0-t)}$ (ng · h/mL) | 107.4 | 122.7 | 87.6 | 84.9 | 90.4 | 7 |
| $AUC_{(0-inf)}$ (ng · h/mL) | 113.6 | 127.5 | 89.1 | 86.6 | 91.7 | 7 |

These statistics were used to evaluate the performance of the test formulation in relation to the reference product and the test product as fed versus fasting.

Pharmacokinetic and Statistical Results of MPH ER Chewable Tablets 40 mg, Fed Versus Fasting Study

| MPH | Geometric Mean | | Ratio (%) | 90% Confidence Limits | | Intra-Sub CV (%) |
|---|---|---|---|---|---|---|
|  | Fed | Fasting |  | Lower | Upper |  |
| $C_{max}$ (ng/mL) | 12.6 | 12.1 | 104.1 | 99.4 | 108.9 | 11 |
| $AUC_{(0-t)}$ (ng · h/mL) | 129.6 | 107.5 | 120.6 | 117.0 | 124.3 | 7 |
| $AUC_{(0-inf)}$ (ng · h/mL) | 137.9 | 113.6 | 121.4 | 118.0 | 124.9 | 7 |

Treatment A: Methylphenidate HCl Extended Release 40 mg chewable tablets—Fasting Treatment B: Methylphenidate HCl Extended Release 40 mg chewable tablets—Fed Treatment C: Methylin™ 10 mg chewable tablets—Fasting Safety Results:

There were no deaths, Serious Adverse Events (SAEs), or other significant adverse events during the conduct of this study. None of the AEs had a significant impact on the safety of the subjects or on the integrity of the study results.

Conclusions:

All treatments under either fasted or fed conditions were well tolerated by all subjects in the study. Based on the results of the study, the test product has similar maximum and peak absorption characteristics when administered under fasting and fed conditions. There is no significant food effect on the test product.

Methylphenidate HCl 40 mg ER chewable tablets produce a mean peak concentration 20% lower than b.i.d. administration of 20 mg of the Methylin™ 10 mg product. The total exposure is similar starting at approximately 4 hours.

All patents, patent publications, and other publications listed in this specification, as well as prior U.S. patent application Ser. No. 17/070,824, filed Oct. 14, 2020, which is a continuation of U.S. patent application Ser. No. 17/113,856 filed Dec. 7, 2020, U.S. patent application Ser. No. 16/700,517, filed Dec. 2, 2019, U.S. patent application Ser. No. 16/033,352, filed Jul. 12, 2018, now U.S. Pat. No. 10,507,203, U.S. patent application Ser. No. 15/660,046, filed Jul. 26, 2017, now abandoned, which is a continuation of U.S. patent application Ser. No. 15/491,547, filed Apr. 19, 2017, now U.S. Pat. No. 9,844,545, U.S. patent application Ser. No. 15/200,625, filed Jul. 1, 2016, which is a continuation of U.S. patent application Ser. No. 15/009,468, filed Jan. 28, 2016 and U.S. patent application Ser. No. 15/009,480, filed Jan. 28, 2016, both of which are continuations of U.S. patent application Ser. No. 14/872,226, filed Oct. 1, 2015, now U.S. Pat. No. 9,295,642, which is a continuation of U.S. patent application Ser. No. 14/624,998, filed Feb. 18, 2015, now U.S. Pat. No. 9,180,100, which is a continuation of U.S. patent application Ser. No. 14/300,580, filed Jun. 10, 2014, now U.S. Pat. No. 8,999,386, prior International Patent Application No. PCT/US2013/054930, filed Aug. 14, 2013 and U.S. Provisional Patent Application Nos. 61/774,783, filed Mar. 8, 2013 and 61/683,513, filed Aug. 15, 2012, are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. A racemic methylphenidate chewable tablet, wherein the chewable tablet is a uniform solid dispersion comprising:
   (a) a water-insoluble, water-permeable, pH-independent barrier coated, racemic methylphenidate—cation exchange resin complex in an optional matrix, wherein the barrier coating comprises a water-insoluble barrier coating polymer and a plasticizer, which barrier coating is present in an amount of about 10% w/w to about 70% w/w % based on the weight of the precoated racemic methylphenidate—cation exchange resin complex—optional matrix, wherein the barrier coating is over the precoated racemic methylphenidate—cation exchange resin complex—optional matrix and provides a sustained release profile to the racemic methylphenidate in (a), and wherein when present the matrix comprises the racemic methylphenidate—cation exchange resin complex and further comprises a water-insoluble polymer or copolymer or a water-soluble polymer or copolymer; and
   (b) at least one immediate release racemic methylphenidate component which releases racemic methylphenidate in (b) in less than about 30 minutes as determined in an in vitro dissolution assay;
   wherein about 50% w/w to about 90% w/w of the racemic methylphenidate in the tablet is provided by (a);
   wherein said chewable tablet is capable of being divided and providing tablet portions which retain the release profile for the racemic methylphenidate in the undivided tablet following oral dosing.

2. The extended release racemic methylphenidate tablet according to claim 1, wherein the water-insoluble, water-permeable, pH-independent barrier coated, racemic methylphenidate—cation exchange resin complex—optional matrix does not comprise a delayed release pH-dependent enteric coating.

3. The extended release racemic methylphenidate tablet according to claim 1, wherein the chewable tablet does not comprise a pH-dependent enteric coating.

4. The extended release racemic methylphenidate tablet according to claim 1, wherein the barrier coating is about 15% to about 65% by weight, of the precoated racemic methylphenidate—cation exchange resin complex—optional matrix.

5. The extended release racemic methylphenidate tablet according to claim 1, wherein the plasticizer is 2% w/w to about 50% w/w of the barrier coating.

6. The extended release racemic methylphenidate tablet according to claim 1, wherein the plasticizer is 2.5% w/w to about 20% w/w of the barrier coating.

7. The extended release racemic methylphenidate tablet according to claim 6, wherein the plasticizer comprises triacetin.

8. The extended release racemic methylphenidate tablet according to claim 1, wherein the optional matrix is absent.

9. The racemic methylphenidate chewable tablet according to claim 1, wherein the sustained release racemic methylphenidate of (a) provides about 60% w/w to about 80% w/w of the racemic methylphenidate, based on the total amount of racemic methylphenidate in the chewable tablet.

10. The racemic methylphenidate chewable tablet according to claim 1, wherein the at least one immediate release component is a racemic methylphenidate—cation exchange resin complex—optional matrix.

11. The racemic methylphenidate chewable tablet according to claim 10, wherein the immediate release racemic methylphenidate—cation exchange resin complex comprises about 20% w/w to about 40% w/w of the total racemic methylphenidate in the chewable tablet.

12. The racemic methylphenidate chewable tablet according to claim 1, wherein the at least one immediate release component comprises uncomplexed racemic methylphenidate or a pharmaceutically acceptable salt thereof.

13. The racemic methylphenidate chewable tablet according claim 12, wherein the pharmaceutically acceptable salt is racemic methylphenidate HCl.

14. The racemic methylphenidate chewable tablet according to claim 8, wherein the composition comprises immediate release uncomplexed racemic methylphenidate or pharmaceutically acceptable salt in an amount of about 5% w/w to about 35% w/w of the total racemic methylphenidate in the chewable tablet.

15. The racemic methylphenidate chewable tablet according to claim 1, wherein the water insoluble, water-permeable, pH-independent barrier coating has a tensile strength in a range of about 150% to about 400%.

16. The racemic methylphenidate chewable tablet according to claim 1, wherein the water insoluble, water-permeable, pH-independent barrier coating comprises (a) a cured, water-permeable, non-ionic, pH-independent barrier coating comprising polyvinylacetate, a stabilizer, and a plasticizer, applied as an aqueous dispersion or (b) an ethylcellulose coating with a plasticizer.

17. The racemic methylphenidate chewable tablet according to claim 1, wherein the barrier coating over the racemic methylphenidate—cation exchange resin complex—optional matrix of (a) is a cured, water-insoluble, water-permeable, non-ionic, pH-independent barrier coating comprises about 70 to about 90% w/w polyvinylacetate, a stabilizer, and about 2 to about 10% w/w of a plasticizer.

18. The racemic methylphenidate chewable tablet according to claim 1, wherein the matrix is present and comprises polyvinylpyrolidone.

19. The chewable racemic methylphenidate tablet according to claim 1, wherein the matrix is present and comprises a water-insoluble polymer or co-polymer.

20. The racemic methylphenidate chewable tablet according to claim 1, wherein said tablet comprises the equivalent of 20 mg racemic methylphenidate HCl, the equivalent of 30 mg racemic methylphenidate HCl, or the equivalent of 40 mg racemic methylphenidate HCl.

21. A racemic methylphenidate chewable tablet, wherein the chewable tablet is a uniform solid dispersion comprising:
   (a) a water-insoluble, water-permeable, pH-independent barrier coated, racemic methylphenidate—cation exchange resin complex in an optional matrix, wherein the barrier coating comprises a water-insoluble barrier coating polymer and a plasticizer, which barrier coating is present in an amount of about 10% w/w to about 70% w/w % based on the weight of the precoated racemic methylphenidate—cation exchange resin complex—optional matrix, wherein the barrier coating is over the precoated racemic methylphenidate—cation exchange resin complex—optional matrix and provides a sustained release profile to the racemic methylphenidate in (a), and wherein when present the matrix comprises the racemic methylphenidate—cation exchange resin complex and further comprises a water-insoluble polymer or copolymer or a water-soluble polymer or copolymer;

(b) a first immediate release component which comprises an immediate release uncoated racemic methylphenidate—ion exchange resin complex, wherein about 5% w/w to about 20% w/w of the total racemic methylphenidate in the tablet is provided by (b); and (c) a second immediate release racemic methylphenidate component which comprises an uncomplexed racemic methylphenidate, wherein about 5% w/w to about 20% w/w of the total racemic methylphenidate in the tablet is provided by (c);

wherein said chewable tablet is capable of being divided and providing tablet portions which retain the release profile for the racemic methylphenidate in the undivided tablet following oral dosing.

22. The racemic methylphenidate chewable tablet according to claim 21, wherein about 60% w/w to about 80% w/w of the racemic methylphenidate in the tablet is provided by (a).

23. The racemic methylphenidate chewable tablet according to claim 21, wherein the first immediate release component (b) is about 15% w/w of the total racemic methylphenidate in the tablet and/or the second immediate release component (c) is about 15% w/w of the total racemic methylphenidate in the tablet.

24. The extended release racemic methylphenidate tablet according to claim 21, wherein the chewable tablet does not comprise a pH-dependent enteric coating.

25. The extended release racemic methylphenidate tablet according to claim 21, wherein the barrier coating is about 15% to about 65% by weight, of the precoated racemic methylphenidate—cation exchange resin complex—optional matrix.

26. The extended release racemic methylphenidate tablet according to claim 21, wherein the plasticizer is 2% w/w to about 50% w/w of the barrier coating.

27. The extended release racemic methylphenidate tablet according to claim 21, wherein the plasticizer is 2.5% w/w to about 20% w/w of the barrier coating.

28. The extended release racemic methylphenidate tablet according to claim 21, wherein the optional matrix is absent.

29. A method for treating a patient having Attention Deficit Hyperactivity Disorder and/or Attention Deficit Disorder, said method comprising orally delivering the racemic methylphenidate chewable tablet according to claim 2 to the patient, wherein the racemic methylphenidate in the tablet provides a clinically observable psychological and/or behavioral response in the patient for a sustained period post-ingestion by the patient.

30. A method for treating a patient having Attention Deficit Hyperactivity Disorder and/or Attention Deficit Disorder, said method comprising orally delivering the racemic methylphenidate chewable tablet according to claim 1 to the patient, wherein the racemic methylphenidate of (a) provides sustained release of the racemic methylphenidate and the at least one immediate release racemic methylphenidate of (b) further provides release of racemic methylphenidate in less than 20 minutes.

* * * * *

UNITED STATES PATENT AND TRADEMARK OFFICE
CERTIFICATE OF CORRECTION

PATENT NO. : 11,103,495 B2
APPLICATION NO. : 17/213744
DATED : August 31, 2021
INVENTOR(S) : Yu-Hsing Tu, Ashok Perumal and Kalyan Kathala Page 1 of 1

It is certified that error appears in the above-identified patent and that said Letters Patent is hereby corrected as shown below:

In the Claims

In Column 34, Claim 29, Line 21, the reference to "claim 2" is replaced with -- claim 1 --.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*